(12) United States Patent
Hanuka et al.

(10) Patent No.: US 8,998,862 B2
(45) Date of Patent: *Apr. 7, 2015

(54) OSTOMY CONTAINMENT DEVICE

(75) Inventors: David Hanuka, Ramat-Yishai (IL); Meir Or, Kfar Eshchar (IL)

(73) Assignee: B. Braun Medical SAS, Boulogne-Billancourt (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/384,343

(22) PCT Filed: Jul. 14, 2010

(86) PCT No.: PCT/IL2010/000565
§ 371 (c)(1),
(2), (4) Date: Jan. 17, 2012

(87) PCT Pub. No.: WO2011/007355
PCT Pub. Date: Jan. 20, 2011

(65) Prior Publication Data
US 2012/0136324 A1    May 31, 2012

Related U.S. Application Data

(60) Provisional application No. 61/225,546, filed on Jul. 14, 2009, provisional application No. 61/330,359, filed on May 2, 2010.

(51) Int. Cl.
*A61F 5/445* (2006.01)
*G01F 23/16* (2006.01)
*A61F 5/44* (2006.01)

(52) U.S. Cl.
CPC ............... *A61F 5/445* (2013.01); *A61F 5/4405* (2013.01); *A61F 2005/4455* (2013.01)

(58) Field of Classification Search
CPC ........ A61F 5/445; G01F 23/16; G01F 23/164
See application file for complete search history.

(56) References Cited

U.S. PATENT DOCUMENTS

| | | | |
|---|---|---|---|
| 2,243,529 A | 5/1941 | Grossman et al. |
| 2,341,984 A | 2/1944 | Graves |
| 2,510,766 A | 6/1950 | Surface |
| 2,544,579 A | 3/1951 | Ardner |

(Continued)

FOREIGN PATENT DOCUMENTS

| | | |
|---|---|---|
| CN | 1694661 | 11/2005 |
| EP | 2027835 | 2/2009 |

(Continued)

OTHER PUBLICATIONS

Written Opinion Dated Jun. 1, 2012 From the International Preliminary Examining Authority Re. Application No. PCT/IB2011/051938.

(Continued)

*Primary Examiner* — Tatyana Zalukaeva
*Assistant Examiner* — Sara Sass

(57) ABSTRACT

An artificial Ostomy containment device comprising an implantable intra-abdominal sleeve adapted to interfere with movement of a closure assembly positioned within the sleeve; and a closure assembly comprising a hollow stomal insert sized and shaped to conduct waste content from an intestinal portion in an abdominal cavity through said insert and out of a stoma, and a fixation element coupled to said stomal insert sized and positioned to interfere with said intra-abdominal sleeve.

27 Claims, 45 Drawing Sheets

(56) References Cited

U.S. PATENT DOCUMENTS

| | | |
|---|---|---|
| 2,639,710 A | 5/1953 | Fazio |
| 2,667,167 A | 1/1954 | Raiche |
| 2,971,510 A | 2/1961 | Berger |
| 3,398,744 A | 8/1968 | Hooper |
| 3,447,533 A | 6/1969 | Spicer |
| 3,718,141 A | 2/1973 | Goetz |
| 3,976,076 A | 8/1976 | Beach |
| 4,030,500 A | 6/1977 | Ronnquist |
| 4,121,589 A | 10/1978 | McDonnell |
| 4,170,231 A | 10/1979 | Collins |
| 4,183,357 A | 1/1980 | Bentley et al. |
| 4,209,010 A | 6/1980 | Ward et al. |
| 4,210,131 A | 7/1980 | Perlin |
| 4,232,672 A | 11/1980 | Steer et al. |
| 4,265,244 A | 5/1981 | Hill |
| 4,338,937 A | 7/1982 | Lerman |
| 4,344,434 A | 8/1982 | Robertson |
| 4,351,322 A | 9/1982 | Prager |
| 4,381,765 A | 5/1983 | Burton |
| 4,399,809 A | 8/1983 | Baro et al. |
| 4,421,124 A * | 12/1983 | Marshall ................ 600/491 |
| 4,462,510 A | 7/1984 | Steer et al. |
| 4,534,761 A | 8/1985 | Raible |
| 4,634,421 A | 1/1987 | Hegemann |
| 4,662,890 A | 5/1987 | Burton et al. |
| 4,721,508 A | 1/1988 | Burton |
| 4,786,283 A | 11/1988 | Andersson |
| 4,804,375 A | 2/1989 | Robertson |
| 4,810,250 A | 3/1989 | Ellenberg et al. |
| 4,854,316 A | 8/1989 | Davis |
| 4,863,447 A | 9/1989 | Smith |
| 4,941,869 A | 7/1990 | D'Amico |
| 4,950,223 A | 8/1990 | Silvanov |
| 4,981,465 A | 1/1991 | Ballan et al. |
| 5,004,464 A | 4/1991 | Leise, Jr. |
| 5,026,360 A | 6/1991 | Johnsen et al. |
| 5,045,052 A | 9/1991 | Sans |
| 5,108,430 A | 4/1992 | Ravo |
| 5,125,916 A | 6/1992 | Panebianco et al. |
| 5,135,519 A | 8/1992 | Helmer |
| 5,163,897 A | 11/1992 | Persky |
| 5,163,930 A | 11/1992 | Blum |
| 5,261,898 A | 11/1993 | Polin et al. |
| 5,269,774 A | 12/1993 | Gray |
| 5,372,594 A | 12/1994 | Colacello et al. |
| 5,401,264 A | 3/1995 | Leise, Jr. |
| 5,501,678 A | 3/1996 | Olsen |
| 5,549,588 A | 8/1996 | Johnsen |
| 5,569,216 A | 10/1996 | Kim |
| 5,658,266 A | 8/1997 | Colacello et al. |
| 5,683,372 A | 11/1997 | Colacello et al. |
| 5,771,590 A | 6/1998 | Colacello et al. |
| 5,785,677 A | 7/1998 | Auweiler |
| 5,947,942 A | 9/1999 | Galjour |
| 6,033,390 A | 3/2000 | Von Dyck |
| 6,050,982 A | 4/2000 | Wheeler |
| 6,329,465 B1 | 12/2001 | Takahashi et al. |
| 6,350,255 B1 | 2/2002 | Von Dyck |
| 6,357,445 B1 | 3/2002 | Shaw |
| 6,481,589 B2 | 11/2002 | Blomdahl et al. |
| 6,485,476 B1 | 11/2002 | Von Dyck et al. |
| 6,595,971 B1 | 7/2003 | Von Dyck et al. |
| 6,659,988 B1 | 12/2003 | Steer et al. |
| 6,689,111 B2 | 2/2004 | Mulhauser et al. |
| 6,695,825 B2 | 2/2004 | Castles |
| 6,723,079 B2 | 4/2004 | Cline |
| 6,963,772 B2 | 11/2005 | Bloom et al. |
| 7,001,367 B2 | 2/2006 | Arkinstall |
| 7,083,569 B2 | 8/2006 | Boulanger et al. |
| 7,087,041 B2 | 8/2006 | Von Dyck et al. |
| 7,250,040 B2 | 7/2007 | Andersen |
| 7,314,443 B2 | 1/2008 | Jordan et al. |
| 7,582,072 B2 | 9/2009 | McMichael |
| 7,670,289 B1 | 3/2010 | McCall |
| 7,857,796 B2 | 12/2010 | Cline et al. |
| 8,070,737 B2 | 12/2011 | Cline et al. |
| 8,092,437 B2 | 1/2012 | Cline |
| 8,100,875 B2 | 1/2012 | Cline et al. |
| 8,142,406 B2 | 3/2012 | Blum |
| 8,388,586 B2 | 3/2013 | Weig |
| 8,460,259 B2 | 6/2013 | Tsai |
| 2003/0150050 A1 | 8/2003 | Tanaka et al. |
| 2003/0199783 A1 | 10/2003 | Bloom et al. |
| 2003/0220621 A1 | 11/2003 | Arkinstall |
| 2004/0029467 A1 | 2/2004 | Lacroix |
| 2004/0073179 A1 | 4/2004 | Andersen |
| 2004/0122527 A1 | 6/2004 | Imran |
| 2004/0167376 A1 | 8/2004 | Peters et al. |
| 2004/0171999 A1 | 9/2004 | Andersen et al. |
| 2004/0181197 A1 * | 9/2004 | Cline .................. 604/337 |
| 2005/0027159 A1 | 2/2005 | Feng et al. |
| 2005/0054996 A1 | 3/2005 | Gregory |
| 2005/0065488 A1 | 3/2005 | Elliott |
| 2005/0104457 A1 | 5/2005 | Jordan et al. |
| 2006/0048283 A1 | 3/2006 | Sorensen |
| 2006/0206069 A1 | 9/2006 | Cline |
| 2006/0229596 A1 | 10/2006 | Weiser et al. |
| 2007/0049878 A1 | 3/2007 | Kim et al. |
| 2007/0142780 A1 | 6/2007 | Van Lue |
| 2007/0219532 A1 | 9/2007 | Karpowicz et al. |
| 2007/0276346 A1 | 11/2007 | Poulsen et al. |
| 2008/0033380 A1 | 2/2008 | Andersen |
| 2008/0091154 A1 | 4/2008 | Botten |
| 2008/0108862 A1 | 5/2008 | Jordan et al. |
| 2008/0135044 A1 | 6/2008 | Freitag et al. |
| 2008/0275410 A1 | 11/2008 | Burt |
| 2009/0043151 A1 | 2/2009 | Gobel |
| 2009/0216206 A1 * | 8/2009 | Nishtala et al. ............. 604/327 |
| 2009/0247969 A1 | 10/2009 | Nishtala et al. |
| 2010/0069859 A1 | 3/2010 | Weig |
| 2010/0174253 A1 | 7/2010 | Cline et al. |
| 2011/0015475 A1 | 1/2011 | Hanuka et al. |
| 2011/0040231 A1 * | 2/2011 | Gregory .................. 604/8 |
| 2011/0106032 A1 | 5/2011 | Kratky |
| 2013/0060212 A1 | 3/2013 | Hanuka et al. |
| 2013/0060213 A1 | 3/2013 | Hanuka et al. |
| 2013/0079736 A1 * | 3/2013 | Hanuka et al. ............. 604/318 |
| 2013/0079737 A1 | 3/2013 | Hanuka et al. |
| 2013/0079738 A1 | 3/2013 | Hanuka et al. |
| 2013/0116642 A1 | 5/2013 | Hanuka et al. |
| 2013/0304008 A1 | 11/2013 | Hanuka et al. |

FOREIGN PATENT DOCUMENTS

| | | |
|---|---|---|
| FR | 2870112 | 11/2005 |
| GB | 2094153 | 9/1982 |
| JP | 2006-314479 | 11/2006 |
| JP | 2008-507308 | 3/2008 |
| WO | WO 87/03192 | 6/1987 |
| WO | WO 90/07311 | 7/1990 |
| WO | WO 96/32904 | 10/1996 |
| WO | WO 99/43277 | 9/1999 |
| WO | WO 01/49224 | 7/2001 |
| WO | WO 02/058603 | 8/2002 |
| WO | WO 03/065945 | 8/2003 |
| WO | WO 03/071997 | 9/2003 |
| WO | WO 2006/010556 | 2/2006 |
| WO | WO 2008/048856 | 4/2008 |
| WO | WO 2008/103789 | 8/2008 |
| WO | WO 2008/141180 | 11/2008 |
| WO | WO 2009/083183 | 7/2009 |
| WO | WO 2009/155537 | 12/2009 |
| WO | WO 2011/007355 | 1/2011 |
| WO | WO 2011/138728 | 11/2011 |
| WO | WO 2011/138731 | 11/2011 |
| WO | WO 2013/022487 | 2/2013 |
| WO | WO 2013/168165 | 11/2013 |

OTHER PUBLICATIONS

International Preliminary Report on Patentability Dated Sep. 6, 2012 From the International Preliminary Examining Authority Re. Application No. PCT/IB2011/051938.

(56) References Cited

OTHER PUBLICATIONS

International Preliminary Report on Patentability Dated Nov. 15, 2012 From the International Bureau of WIPO Re. Application No. PCT/IB2011/051936.
Official Action Dated Mar. 5, 2013 From the US Patent and Trademark Office Re. U.S. Appl. No. 13/666,513.
Official Action Dated Mar. 25, 2013 From the US Patent and Trademark Office Re. U.S. Appl. No. 13/666,178.
Notification Concerning Informal Communications With the Applicant Dated May 3, 2012 From the International Searching Authority Re: Application No. PCT/IB2011/051938.
Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Official Action Dated May 9, 2013 From the US Patent and Trademark Office Re. U.S. Appl. No. 13/666,461.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
Restriction Official Action Dated Oct. 15, 2012 From the US Patent and Trademark Office Re. U.S. Appl. No. 12/835,838.
Official Action Dated Jan. 30, 2013 From the US Patent and Trademark Office Re. U.S. Appl. No. 12/835,838.
Communication Pursuant to Article 94(3) EPC Dated Feb. 11, 2013 From the European Patent Office Re. Application No. 10747082.5.
Communication Relating to the Results of the Partial International Search Dated Aug. 12, 2011 From the International Searching Authority Re. Application No. PCT/IB2011/051932.
Communication Relating to the Results of the Partial International Search Dated Aug. 16, 2011 From the International Searching Authority Re. Application No. PCT/IB2011/051933.
Communication Relating to the Results of the Partial International Search Dated Nov. 17, 2010 From the International Searching Authority Re. Application No. PCT/IL2010/000565.
Communication Relating to the Results of the Partial International Search Dated Aug. 18, 2011 From the International Searching Authority Re: Application No. PCT/IB2011/051938.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 From the International Searching Authority Re. Application No. PCT/IB2011/051932.
International Search Report and the Written Opinion Dated Aug. 18, 2011 From the International Searching Authority Re. Application No. PCT/IB2011/051936.
International Search Report and the Written Opinion Dated Oct. 19, 2011 From the International Searching Authority Re: Application No. PCT/IB2011/051938.
International Search Report and the Written Opinion Dated Feb. 28, 2011 From the International Searching Authority Re. Application No. PCT/IL2010/000565.
Invitation to Pay Additional Fees Dated Oct. 7, 2011 From the International Preliminary Examining Authority Re. Application No. PCT/IL2010/000565.
Response Dated May 30, 2011 to the Written Opinion of Feb. 28, 2011 From the International Searching Authority Re. Application No. PCT/IL2010/000565.
Applicant-Initiated Interview Summary Dated Jul. 25, 2013 From the US Patent and Trademark Office Re. U.S. Appl. No. 13/680,161.
Applicant-Initiated Interview Summary Dated Jul. 26, 2013 From the US Patent and Trademark Office Re. U.S. Appl. No. 13/666,513.
Applicant-Initiated Interview Summary Dated Jul. 26, 2013 From the US Patent and Trademark Office Re. U.S. Appl. No. 13/680,169.
Translation of Notification of Office Action Dated Jul. 30, 2013 From the State Intellectual Property Office of the People's Republic of China Re. Application No. 201080032032.X.
Official Action Dated Aug. 29, 2013 From the US Patent and Trademark Office Re. U.S. Appl. No. 12/835,838.
Official Action Dated Jul. 10, 2013 From the US Patent and Trademark Office Re. U.S. Appl. No. 13/680,169.
Official Action Dated Jul. 11, 2013 From the US Patent and Trademark Office Re. U.S. Appl. No. 13/680,161.
Applicant-Initiated Interview Summary Dated Apr. 14, 2014 From the US Patent and Trademark Office Re. U.S. Appl. No. 13/384,343.
Notice of Allowance Dated Apr. 29, 2014 From the US Patent and Trademark Office Re. U.S. Appl. No. 13/680,161.
Notification of Office Action Dated Apr. 18, 2014 From the State Intellectual Property Office of the People's Republic of China Re. Application No. 201080032032.X and Its Translation Into English.
Search Report Dated Apr. 18, 2014 From the State Intellectual Property Office of the People's Republic of China Re. Application No. 201080032032.X and Its Translation Into English.
Notice of Allowance Dated May 8, 2014 From the US Patent and Trademark Office Re. U.S. Appl. No. 13/666,461.
Notice of Reason for Rejection Dated Apr. 15, 2014 From the Japanese Patent Office Re. Application No. 2012-520149 and Its Translation Into English.
Communication Under Rule 71(3) EPC Dated May 19, 2014 From the European Patent Office Re. Application No. 10747082.5.
Notification of Office Action Dated May 6, 2014 From The State Intellectual Property Office of the People's Republic of China Re. Application No. 2011800331827 and its Translation into English.
Search Report Dated May 6, 2014 From the State Intellectual Property Office of the People's Republic of China Re. Application No. 2011800331827 and Its Translation Into English.
Communication Relating to the Results of the Partial International Search Dated Sep. 16, 2013 From the International Searching Authority Re. Application No. PCT/IL2013/050401.
Official Action Dated Nov. 7, 2013 From the US Patent and Trademark Office Re. U.S. Appl. No. 13/666,178.
Official Action Dated Nov. 7, 2013 From the US Patent and Trademark Office Re. U.S. Appl. No. 13/680,169.
Official Action Dated Nov. 13, 2013 From the US Patent and Trademark Office Re. U.S. Appl. No. 13/666,461.
Official Action Dated Oct. 16, 2013 From the US Patent and Trademark Office Re. U.S. Appl. No. 13/666,244.
Official Action Dated Oct. 16, 2013 From the US Patent and Trademark Office Re. U.S. Appl. No. 13/666,513.
Applicant-Initiated Interview Summary Dated Dec. 13, 2013 From the US Patent and Trademark Office Re. U.S. Appl. No. 13/666,244.
Applicant-Initiated Interview Summary Dated Dec. 13, 2013 From the US Patent and Trademark Office Re. U.S. Appl. No. 13/666,513.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
International Search Report and the Written Opinion Dated Dec. 20, 2013 From the International Searching Authority Re. Application No. PCT/IL2013/050401.
Official Action Dated Jan. 14, 2014 From the US Patent and Trademark Office Re. U.S. Appl. No. 13/680,161.
Summons to Attend Oral Proceedings Pursuant to Rule 115(1) EPC Dated Nov. 22, 2013 From the European Patent Office Re. Application No. 10747082.5.
Advisory Action Before the Filing of an Appeal Brief Dated Feb. 4, 2014 From the US Patent and Trademark Office Re. U.S. Appl. No. 12/835,838.

(56) References Cited

OTHER PUBLICATIONS

Notice of Allowance Dated Apr. 4, 2014 From the US Patent and Trademark Office Re. U.S. Appl. No. 13/680,169.
Notice of Allowance Dated Feb. 18, 2014 From the US Patent and Trademark Office Re. U.S. Appl. No. 13/666,513.
Notice of Allowance Dated Mar. 18, 2014 From the US Patent and Trademark Office Re. U.S. Appl. No. 13/666,178.
Communication Relating to the Results of the Partial International Search Dated Sep. 16, 2014 From the International Searching Authority Re. Application No. PCT/IL2014/050417.
Communication Relating to the Results of the Partial International Search Dated Sep. 16, 2014 From the International Searching Authority Re. Application No. PCT/IL2014/050416.
Notice of Allowance Dated Oct. 1, 2014 From the US Patent and Trademark Office Re. U.S. Appl. No. 12/835,838.
Notification of Office Action Dated May 27, 2014 From The State Intellectual Property Office of the People's Republic of China Re. Application No. 201180033162.X.
Official Action Dated Jul. 29, 2014 From the US Patent and Trademark Office Re. U.S. Appl. No. 13/666,244.

\* cited by examiner

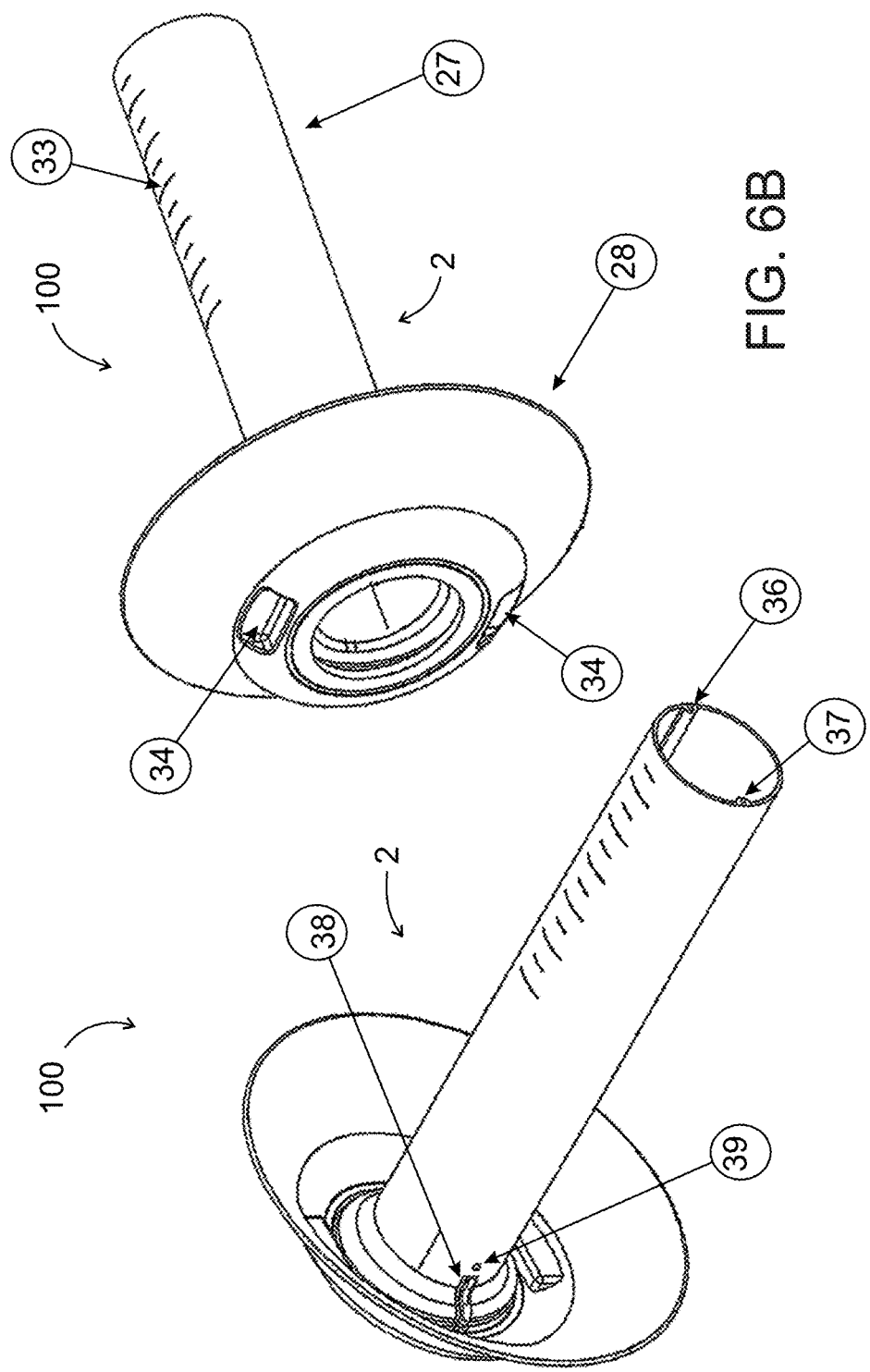

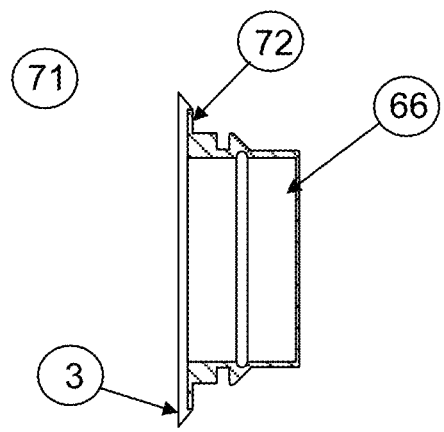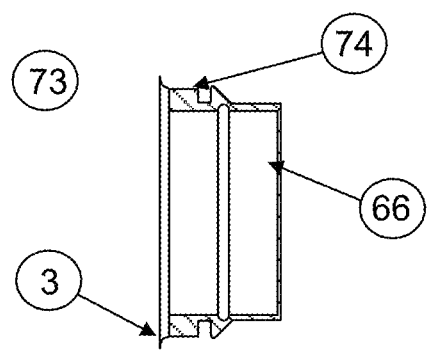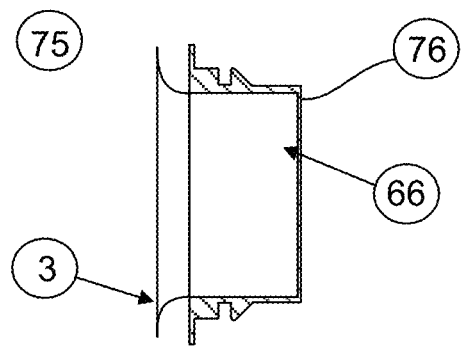
FIG. 9C

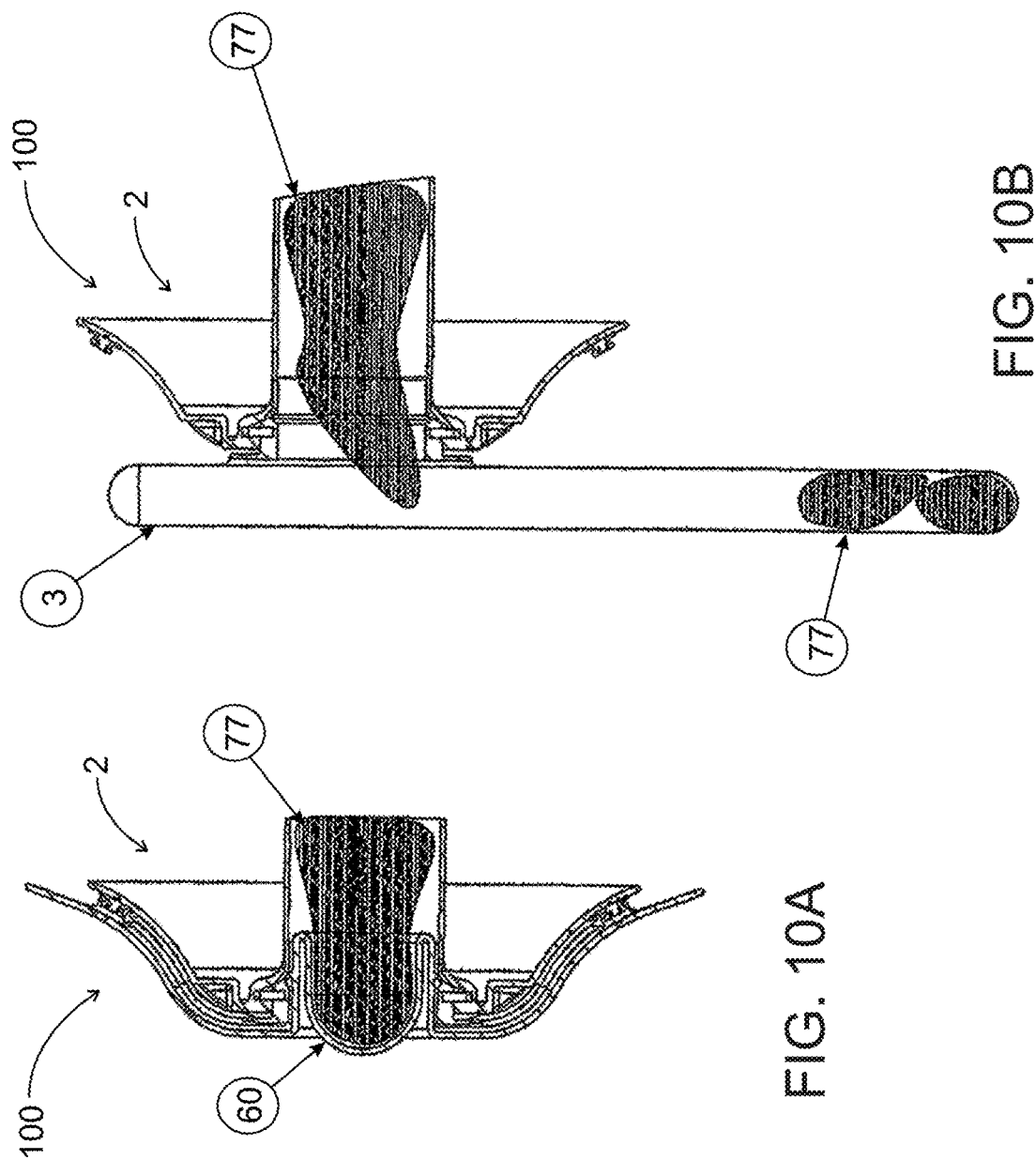

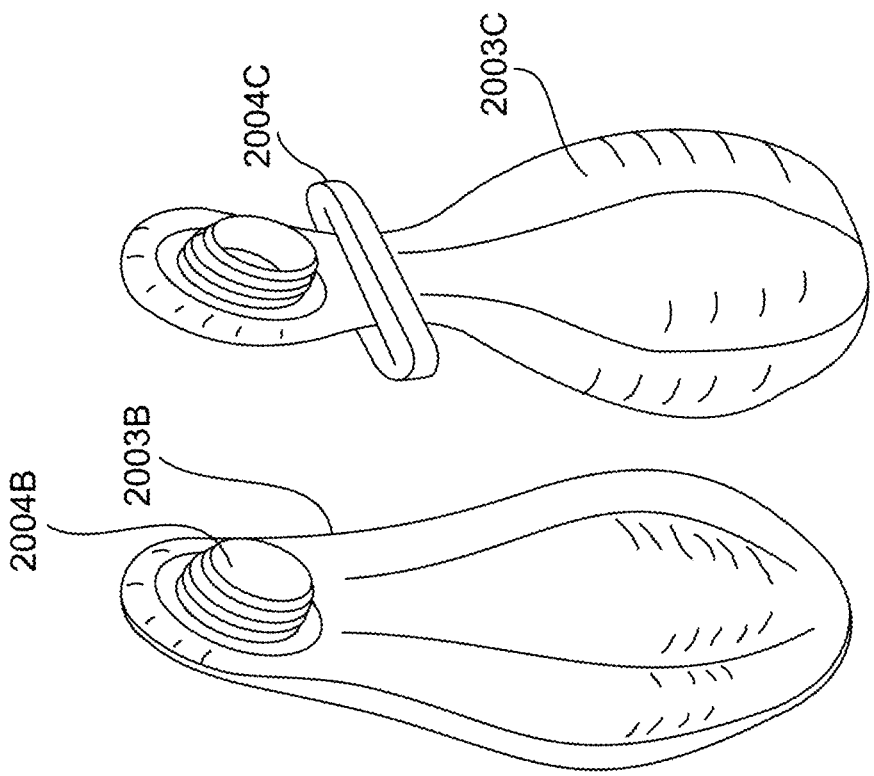
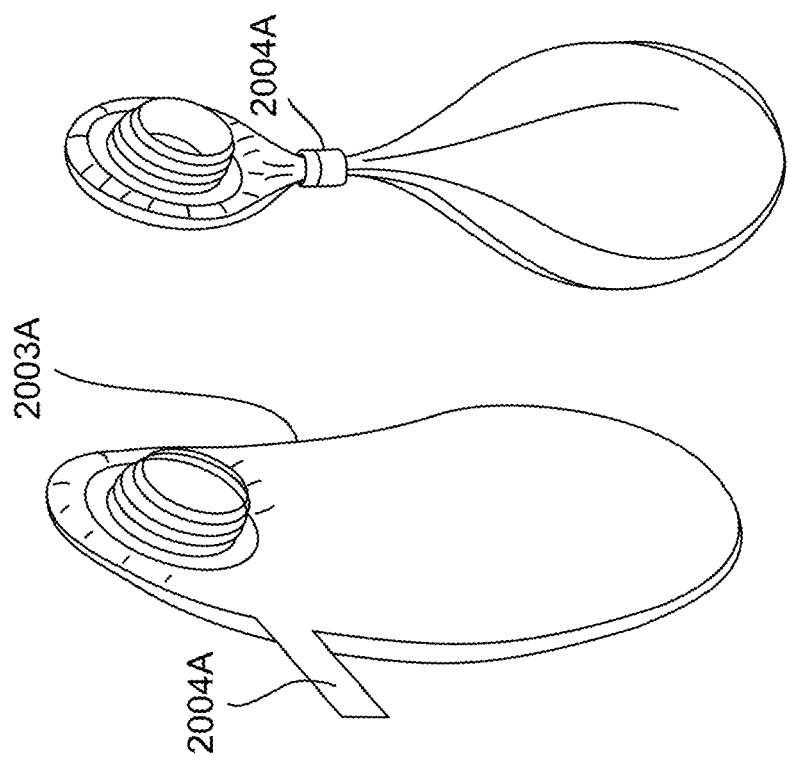
FIG. 20A  FIG. 20B  FIG. 20C

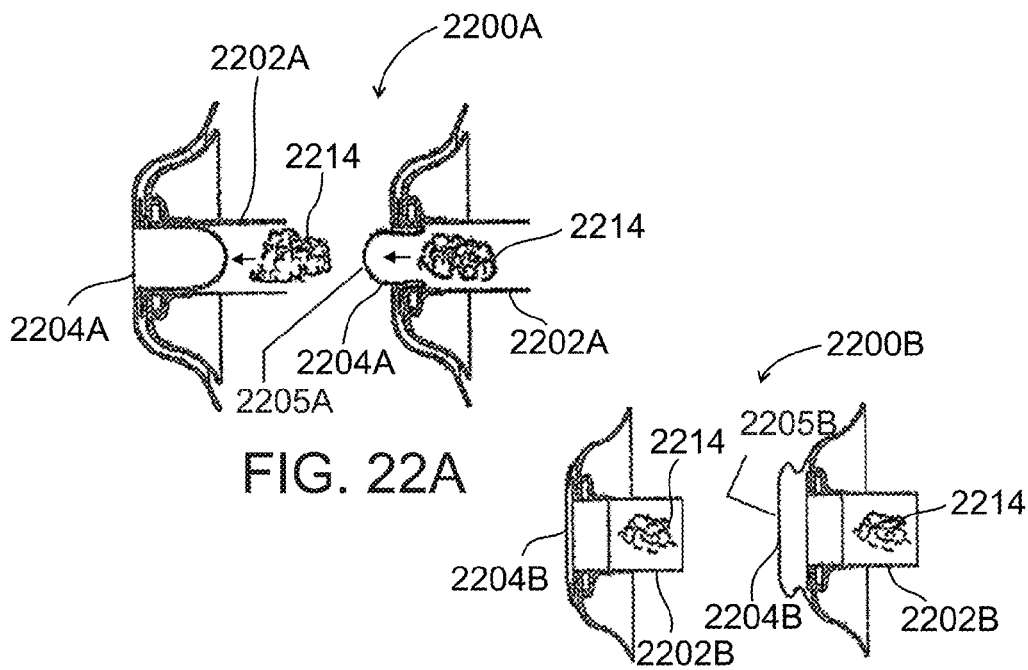
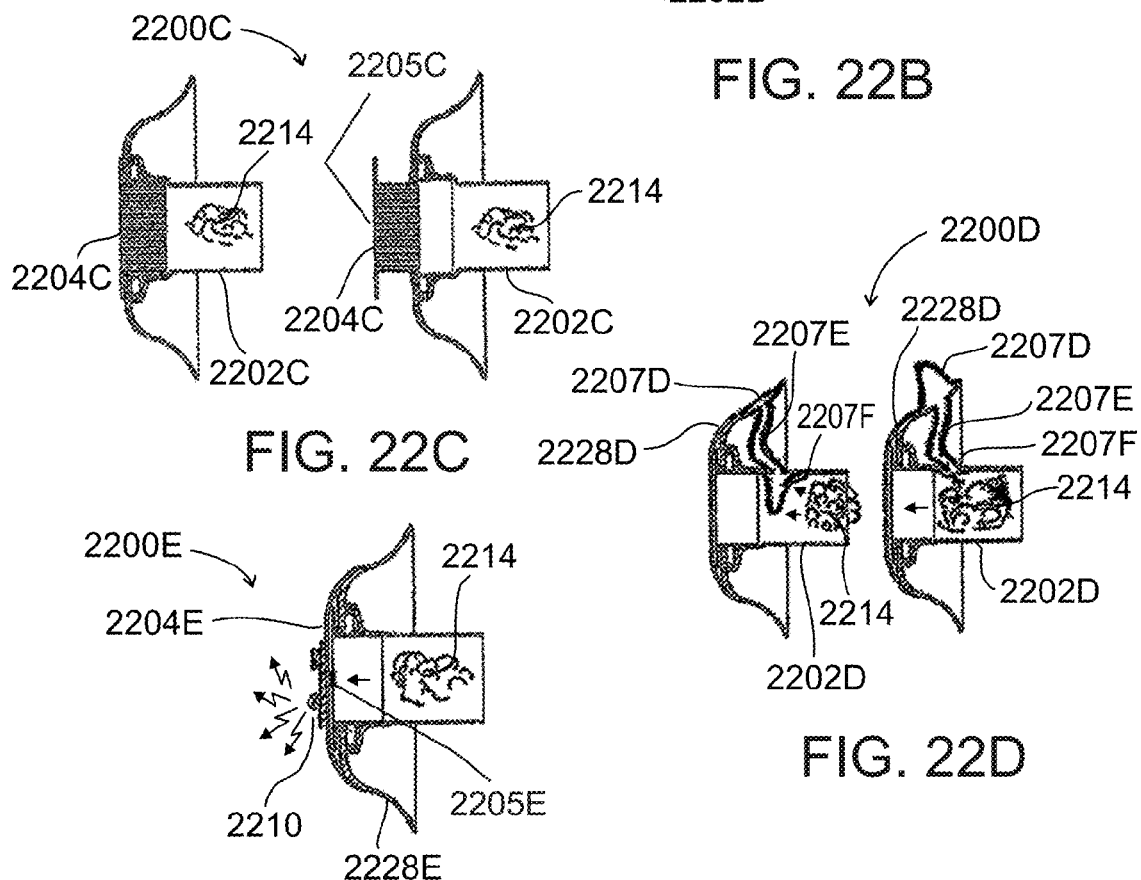

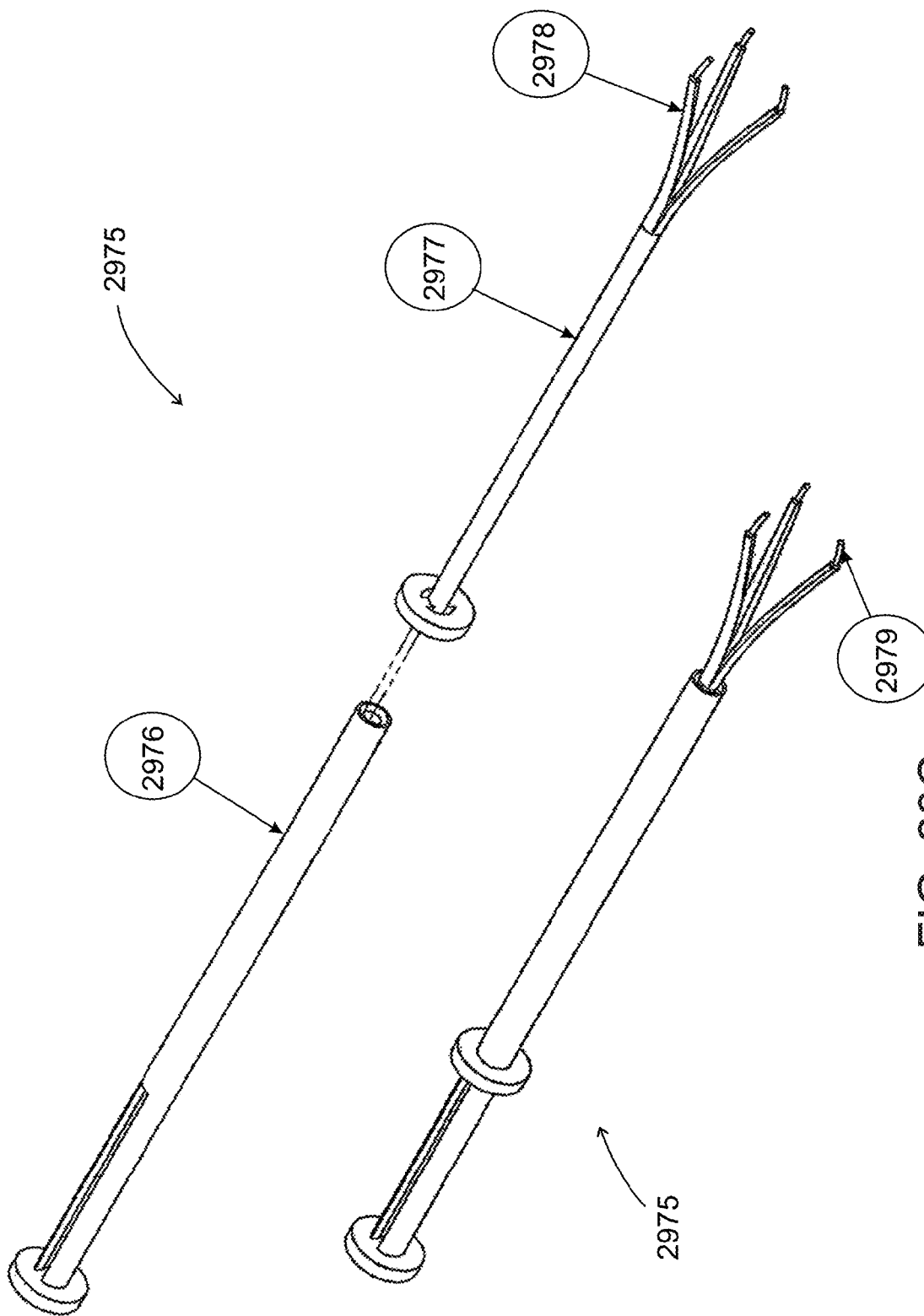

STEP 4
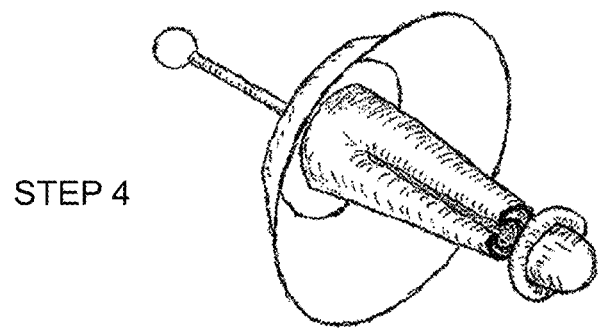
STEP 5
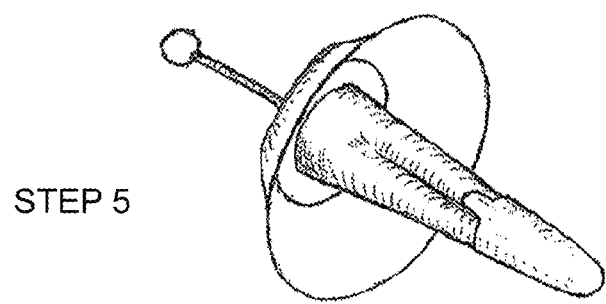
STEP 6
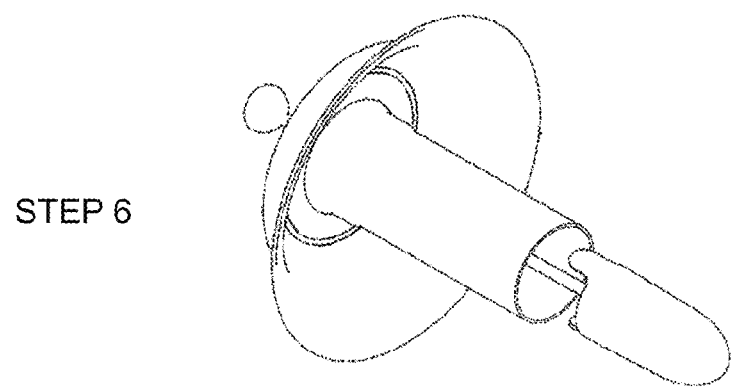
FIG. 29F

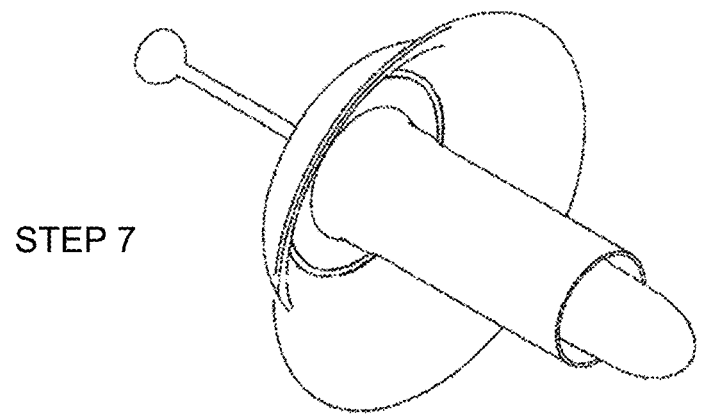
STEP 7
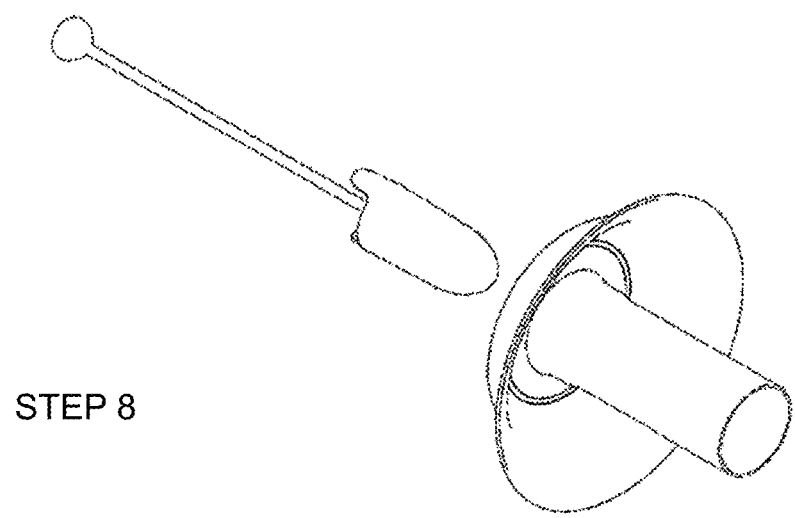
STEP 8
FIG. 29G

FIG. 30A          FIG. 30B
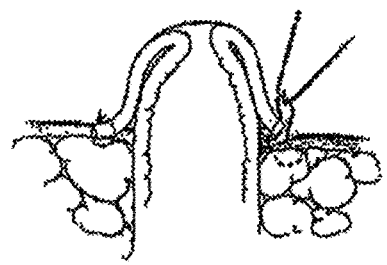
FIG. 30C          FIG. 30D
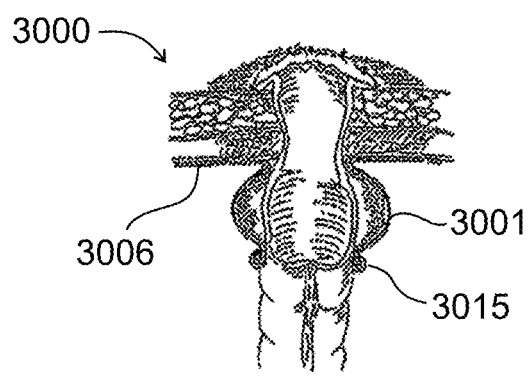
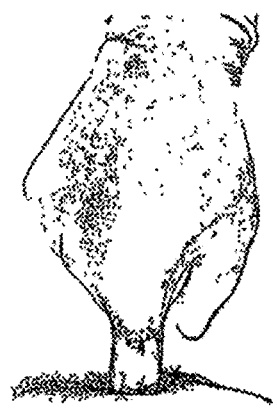
FIG. 30E          FIG. 30F

OSTOMY CONTAINMENT DEVICE

RELATED APPLICATIONS

This application is a National Phase of PCT Patent Application No. PCT/IL2010/000565 having international filing date of Jul. 14, 2010, which claims the benefit of priority of U.S. Provisional Patent Application Nos. 61/225,546 filed on Jul. 14, 2009, and 61/330,359 filed on May 2, 2010, the disclosures of which are incorporated herein by reference in their entirety. The contents of all of the above documents are incorporated by reference as if fully set forth herein.

FIELD AND BACKGROUND OF THE INVENTION

The present invention, in some embodiments thereof, relates to the field of prosthetic implants, and more particularly, to an Ostomy containment device for use following Ostomy cases such as Colostomy, Ileostomy or Urostomy, and fecal incontinence.

An Ostomy is a surgical procedure wherein an opening (stoma) is created in the body, for example, for the discharge of body wastes. Common types of ostomies are colostomy, ileostomy and urostomy. The colostomy is a surgical procedure involving forming a stoma, generally from an end or from the side of a healthy portion of the large intestine, by diverting the large intestine to the abdominal wall. The ileostomy is a surgical procedure involving forming a stoma, generally from an end or from the side of a healthy portion of the ileum in the small intestine, usually by diverting the small intestine to the abdominal wall (frequently in the groin area of the wall). The urostomy is a surgical procedure which diverts urine away from a diseased or defective bladder, and generally includes removing a section at the end of the small intestine (ileum) or at the beginning of the large intestine (cecum), and relocating the section as a conduit for urine to pass from the kidneys to the outside of the body through a stoma in the abdominal wall. In some cases, a stoma may be permanent, for example where it is no longer possible for the intestinal content to pass out via the anus (e.g. due to colon cancer, diverticulitis, trauma, inflammatory bowel disease, etc.). Optionally, the stoma may be temporary, for example following an operation on a section of the bowel (small intestine and/or large intestine) where the section may require a period of time for healing.

Following a stoma operation, an Ostomy containment system or its portion may be used to control the flow of body waste through the stoma. The Ostomy containment system may be a non-irrigation system which includes use of a pouch in which feces or urine is collected; or an irrigation system which includes means for washing out the bowel without the use of a pouch. In the non-irrigation system the pouch generally requires emptying or changing several times a day, depending on a frequency of bowel activity. In the irrigation system, a removable closure such as a gauze cap may be placed over the stoma, and irrigation is performed by inserting a catheter inside the stoma and flushing with water. This allows the body waste to flow out of the body into an irrigation sleeve or bag. Irrigation may generally be performed once a day, although the frequency may vary according to the person, location of the stoma, food intake, and health of the person. An alternative arrangement for an ostomy containment system includes implementation of an artificial sphincter, either implanted or externally attached to the stoma, by which the user can shut-off or enable the flow of body waste out of the stoma.

U.S. Pat. No. 5,197,984 discloses "A shut-off device particularly useful as an artificial sphincter for shutting-off the flow from a passage in a subject's body includes a conduit assembly attachable to the body with its inner end in alignment with the passage, a ring rotatably mounted in the outer end of the conduit assembly, and an elastomeric sleeve passing through the conduit assembly and ring, with the inner end of the sleeve attached to the inner end of the conduit assembly, and the outer end of the sleeve attached to the ring. The pliable sleeve is of a length such that the ring may be rotated with respect to the conduit assembly to twist the pliable sleeve from an untwisted open condition permitting the flow of the material from the body passage, to a twisted closed condition shutting-off the flow of the material."

U.S. Pat. No. 4,351,322 discloses "A stoma control device and method are disclosed. The device comprises, in combination, a support such as a ring for surgical implantation in the body beneath the abdominal wall and substantially around the emerging bowel of a stoma, the support being formed of a relatively soft material such as soft plastic and having an inner surface which tapers outwardly to present a relatively large supporting surface for the bowel, and a plug adapted to be received in the stoma and within the bowel for controlling the stoma, the plug including an inflatable balloon, the balloon, on inflation, presenting an outwardly tapered surface with a shape which complements the tapered inner surface of the support whereby during control of the stoma with the device a relatively large surface of the bowel may be greatly compressed between the plug and the support so as to minimize pressure and tissue destruction."

U.S. Pat. No. 4,204,282 discloses "An implantable artificial sphincter in the form of a sleeve for receiving and supporting therein the remaining terminal end of healthy bowel tissue. The sleeve is provided with multiple openings therethrough for the growth and passage of anchoring fibrous granulation tissue and the sleeve is provided with a removable closure which is position in the patient at the point were the anal sphincter was surgically removed thereby providing an artificial sphincter in near normal anatomical position."

U.S. Pat. No. 4,121,589 discloses "An Ostomy appliance comprises an attachment portion having an aperture therethrough adapted to register with an opening in the body of a patient and having adhesive on one face thereof adapted to secure the attachment portion to the body of the patient surrounding the opening, the attachment portion being provided on the opposite face thereof with structure for securing a cap member in sealing relationship thereto over the aperture; and a cap member comprising a generally concave body member of rigid or semi-rigid material, the body member containing absorbent material for absorbing drainage and/or discharge from the opening and being provided with structure engaging the attachment portion for securing said cap member to said attachment means. The appliance may further include an absorber member adapted to be inserted into the opening through the aperture in the attachment portion, the absorber member comprising a generally tubular absorption and storage member having inner and outer walls of fluid pervious material, the inner and outer walls being separated by absorbent material, and a flange at one end of the tubular member to retain the absorber member in position in the opening on securing the cap member to the attachment portion."

WO 96/32904 discloses "The problem which is solved by a prosthesis for bowel evacuation control at the incontinence of an artificial or natural anus in accordance with the invention is how to provide simple, safe and reliable control of bowel evacuation in artificial or natural incontinence, where under artificial incontinence colostomy, i.e. a surgically formed opening in the large intestine through the abdominal wall is understood, and under natural incontinence the incontinence of the anal sphincter is understood. The illustrated prosthesis inserted in a colostomy, i.e. a bowel (1) extended through the abdominal wall (2), consists of an inner ring (3) which continues into a pellicular tube (4) and this into a faceplate (5), and of a cover (8). In this embodiment the inner ring (3) is carried out as a ring made of pliable, organism-friendly material with a built-in reinforcement (9) providing a sufficient force for reexpansion of the ring (3) and preventing its deformation when being inserted into the bowel lumen. The inner ring (3) continues along its entire circumference into the tube (4) whose thin walls are made of a material with similar characteristics as the inner ring (3). The diameter of an unstretched tube (4) is a little smaller than the diameter of the inner ring (3). The length of the tube (4) in this embodiment is a little smaller than the thickness of the abdominal wall (2). At the end lying opposite to the inner ring (3) the tube (4) continues into a faceplate (5) which is preferably of circular form and made of firm material or dimensioned so that it is firm yet pliable. The plate (5) has an opening in the centre in which the cover (8) is inserted which prevents the feces from escaping."

Additional background art includes the following U.S. Pat. Nos. 4,766,845; 2,510,766; 2,544,579; 2,931,353; 3,447,533; 3,802,418; 4,0350,500; 4,192,785; 4,209,010; 4,981,465; 4,634,443; 4,551,862; 5,045,052; 5,569,216; 6,485,476; 7,087,041; 4,209,010; 4,210,132; 4,399,809; 6,033,390; 4,619,245; and 2,457,244.

SUMMARY OF THE INVENTION

According to an aspect of some embodiments of the present invention there is provided an artificial Ostomy containment device comprising an implantable intra-abdominal sleeve adapted to interfere with movement of a closure assembly positioned within the sleeve; and a closure assembly comprising a hollow stomal insert sized and shaped to conduct waste content from an intestinal portion in an abdominal cavity through the insert and out of a stoma, and a fixation element coupled to the stomal insert sized and positioned to interfere with the intra-abdominal sleeve.

In some exemplary embodiments, the fixation element is an inflatable balloon.

In some exemplary embodiments, the stomal insert comprises a lumen for conveying an expansion fluid to the inflatable balloon.

In some exemplary embodiments, the closure comprises an inflation valve for introducing the expansion fluid into the lumen.

In some exemplary embodiments, the fixation element is a pre-shaped elastically deformable element configured to be inserted into the cavity sleeve.

In some exemplary embodiments, the containment device comprises a stomal cover at a proximal end of the stomal insert sized and shaped to cover the stoma from outside the abdominal cavity.

In some exemplary embodiments, the stomal insert is further adapted to be removed from the sleeve and extracted from the stoma.

In some exemplary embodiments, a maximum compressive force $t_n$ exerted against the intestinal portion inside the sleeve cavity is described by the following mathematical relationship:

$$t_n = p \times R'^2_1 / (R_2^2 - R_3^2)$$

where p=an intestinal pressure at the distal neck of the sleeve, $t_n$=the compressive stress on the tissue, $R_2$=a maximum radius at an apex of the sleeve cavity wall, $R_3$=a minimum radius at the proximal neck of the sleeve, and $R'_1$=a maximum outer radius of the stomal insert.

In some exemplary embodiments, a maximum compressive stress force exerted against the intestinal portion inside the sleeve cavity is less than 250 mmHg.

In some exemplary embodiments, a maximum compressive stress force exerted against the intestinal portion inside the sleeve cavity is less than 50 mmHg.

In some exemplary embodiments, the containment device comprises a flexible flange for affixing the sleeve to a visceral wall of the abdominal cavity.

In some exemplary embodiments, the flexible flange is adapted to affix abdominal wall tissue peripherally surrounding the stoma.

In some exemplary embodiments, the containment device comprises a mechanism for communicating to a user a need for evacuation.

In some exemplary embodiments, the containment device comprises a safety mechanism for releasing bowel waste content when the colonic pressure reaches is equal to or greater than 125 mmHg for a period of time greater or equal to 5 seconds.

In some exemplary embodiments, the closure comprises a material of durometer ranging from 20-80 Shore A for allowing peristaltic propelling of the waste content.

In some exemplary embodiments, the sleeve comprises an axial slot for accommodating the mesentery.

In some exemplary embodiments, the containment device comprises a flange with an opening through which an intestinal portion in inserted.

In some exemplary embodiments, the containment device comprises a narrow flange with openings for anchoring the sleeve to an abdominal wall.

In some exemplary embodiments, the sleeve comprises openings for releasing gases trapped between the sleeve and the intestinal portion.

In some exemplary embodiments, the fixation element comprises a non-collapsible balloon.

In some exemplary embodiments, the containment device comprises an inflatable balloon inside the stomal insert for blocking a flow of the waste content.

In some exemplary embodiments, the fixation element comprises a broadening of the stomal insert.

According to an aspect of some embodiments of the present invention there is provided a method for preventing leakage from a stoma comprising inserting a closure assembly through the stoma into an intra-abdominal sleeve; interfering with the sleeve; and attaching a cap to a stomal cover covering the stoma.

In some exemplary embodiments, interfering with the sleeve comprises inflating a balloon.

In some exemplary embodiments, the method comprises inflating the balloon with an expansion fluid.

In some exemplary embodiments, the method comprises pouring the expansion fluid through an inflation valve.

According to an aspect of some embodiments of the present invention there is provided a flexible flange for attaching a proximal neck of a sleeve in an artificial Ostomy containment device to a visceral side of an abdominal wall, the flange comprising openings sized and shaped to allow the flange to adjust to a shape of the abdominal wall.

In some exemplary embodiments, the openings comprise slots.

In some exemplary embodiments, the flange comprises suture openings for suturing the flange to the abdominal wall.

In some exemplary embodiments, the flange comprises a circumferential flange rim for protecting the flange from tearing by the sutures.

In some exemplary embodiments, the flange comprises circumferential opening rims for protecting the flange from tearing by the sutures.

According to an aspect of some embodiments of the present invention there is provided a stomal insert comprising an irrigation lumen extending along a length of the insert, the lumen comprising a proximal opening sized and positioned to introduce irrigation fluid into the lumen and at least one opening sized and positioned to pass the fluid from the lumen into the intestinal portion.

In some exemplary embodiments, the stomal insert comprises a fluid administration valve sized and shaped to introduce the irrigation fluid into the lumen.

In some exemplary embodiments, the fluid administration valve is adapted to introduce medications and/or nutrients into the lumen.

In some exemplary embodiments, the stomal insert comprises a tube to connect the fluid administration valve to the irrigation lumen and passing through a stomal cover.

In some exemplary embodiments, the irrigation lumen is adapted to pass flatus from the intestinal portion to a flatus release valve.

In some exemplary embodiments, the lumen comprises a plurality of holes through which flatus passes from the intestine portion to the release valve.

According to an aspect of some embodiments of the present invention there is provided a stomal insert with a cover comprising a convex section to create a hollow void for maintaining a distance between the cover and a stoma.

In some exemplary embodiments, a shape of the cover is adjustable to cover variations in abdominal wall thickness.

In some exemplary embodiments, the shape of the stomal cover is invertible to allow access to the stoma.

According to an aspect of some embodiments of the present invention there is provided a stomal insert including a cap sized and shaped to sense a presence of waste content in the insert by protruding in a proximal direction out of the insert due to a pressure exerted by the waste content.

According to an aspect of some embodiments of the present invention there is provided a disposable bag for collecting waste content from an Ostomy containment device comprising a bag housing including a folded bag, the housing attached to a proximal end of a stomal insert in the containment device.

In some exemplary embodiments, the bag housing is replaceable.

In some exemplary embodiments, the bag housing is permanently affixed to the stomal insert.

According to an aspect of some embodiments of the present invention there is provided a medical kit for performing an Ostomy comprising an implantable intra-abdominal sleeve adapted to interfere with movement of a closure assembly positioned within the sleeve; and a closure assembly comprising a hollow stomal insert sized and shaped to conduct waste content from an intestinal portion in an abdominal cavity through the insert and out of a stoma; and a fixation element coupled to the stomal insert sized and positioned to interfere with the intra-abdominal sleeve.

In some exemplary embodiments, the medical kit comprises a laparoscope.

In some exemplary embodiments, the medical kit comprises a surgical knife.

In some exemplary embodiments, the medical kit comprises an introducer for inserting the closure through the stoma. Optionally, the introducer comprises a flexible envelope. Optionally, the envelope comprises a convex shaped distal end. Optionally, the envelope is adapted to be rolled. Optionally, the envelope comprises a biocompatible material. Optionally, the introducer further comprises a handle onto which said envelope is attached.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 6A and 6B schematically illustrate perspective views of a stomal insert and a stomal cover in the closure, all according to an embodiment of the present invention;

FIG. 9C schematically illustrates various modes of attachment of the bag to a housing, according to some embodiments of the invention;

FIGS. 20A-20C schematically illustrate methods of closing an exemplary waste content collection bag when removed from a closure following evacuation, according to some embodiments of the present invention;

FIGS. 22A-22E schematically illustrate exemplary mechanisms for notifying a user of a need to evacuate, according to some embodiments of the present invention;

FIGS. 29A-29G schematically illustrate exemplary methods of inserting a closure into a sleeve and an intestinal portion, including tools optionally used for carrying out the methods, according to some embodiments of the present invention;

FIGS. 30A-30F schematically illustrate exemplary steps in implantation of an exemplary sleeve during the performance of a new end-ostomy using open surgery, according to some embodiments of the present invention;

DESCRIPTION OF EMBODIMENTS OF THE INVENTION

Figure 1:
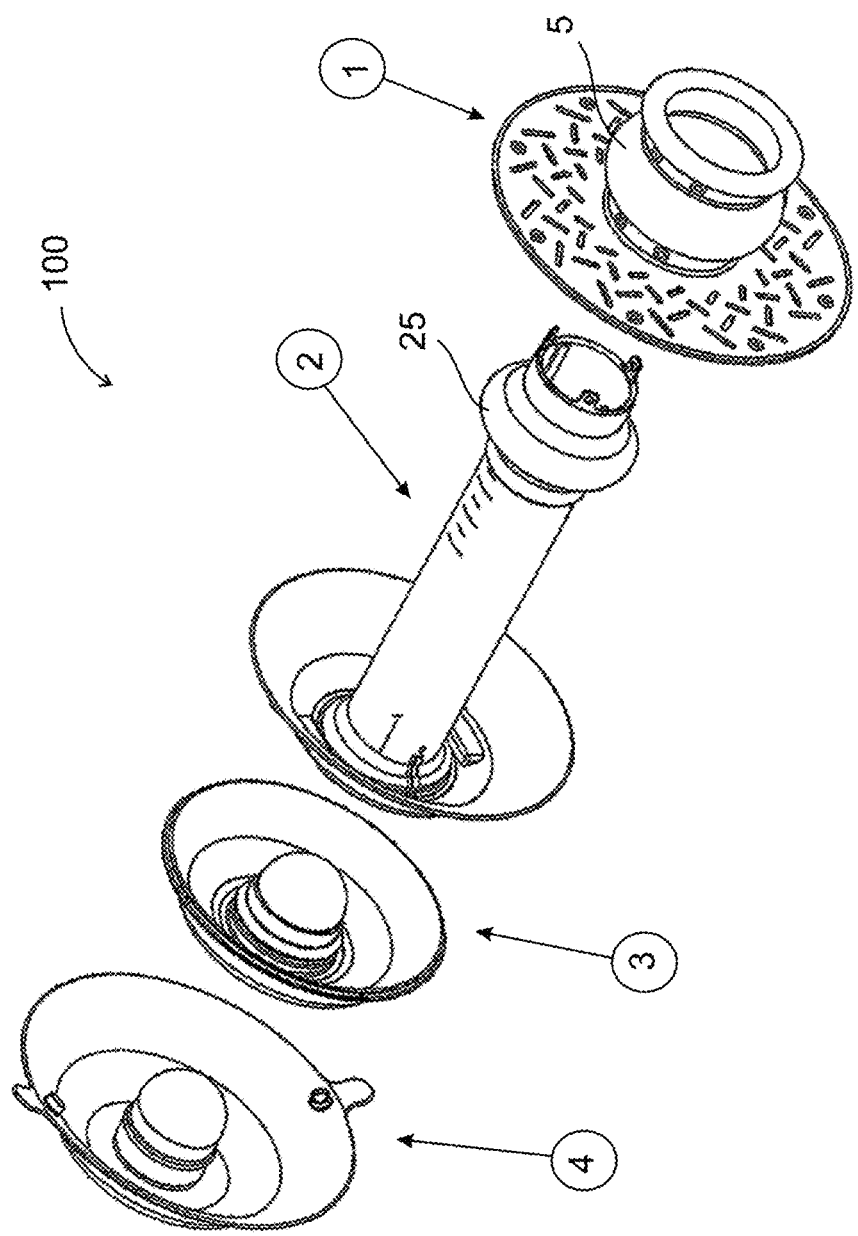
FIG. 1 schematically illustrates a perspective view of an exemplary Ostomy containment device, according to an embodiment of the present invention.

The present invention, in some embodiments thereof, relates to the field of prosthetic implants, and more particularly, to an Ostomy containment device for use following Ostomy cases such as Colostomy, Ileostomy or Urostomy, and fecal incontinence.

Numerous Ostomy containment systems are known in the art, many of which exhibit problems when used by a person (user). Using a non-irrigation systems in which a collection bag is attached to the stoma and the body waste is free to flow into the bag, is usually accompanied by several problems. These include, for example, leakage of body waste through the interface between the bag and the user, irritation of the user's skin as a result of the said leakage or due to repeated attachment and detachment processes between parts of the containment system and the user's skin, ballooning of the collection bag, and embarrassing sounds. Using an irrigation system is also characterized by typical problems, among which one can find the long duration required for the irrigation process, during which the user must stay in the bathroom, intestinal abrasion due to repeated insertion and withdrawal of the irrigation catheter, and the non-sealed closure of the stoma between irrigations which may allow for inadvertent discharge of body waste should a sudden bowel movement occur. Another problem is related to an insufficient attachment of the intestine/organ to the abdominal wall, allowing movement of the intestine/organ and which may result in a parastomal hernia, stomal prolapse, or stomal retraction. Ostomy containment systems which include a device that functions as an artificial sphincter suffer too from ample complications. One of the problems, for example, is related to a use of excessive compressive force on intestinal tissue by the sphincter which may cause compression-related clinical problems such as ischemia, necrosis, decubitus, fistulation and the like. Another problem is the leakage of body waste during installation and removal of the sphincter, which again may cause skin irritation to the user. Still another problem may be related to the containment device including a conduit for body waste flow made of a material which substantially prevents peristaltic propelling of feces (fecal content), possibly resulting in fecal content obstructing the containment device and intestinal blockage. One or more of the above mentioned problems may be solved by practicing one or more embodiments of the present invention as described below.

An aspect of some embodiments of the present invention relates to an artificial Ostomy containment device (hereinafter referred to as "the containment device" or "the device") for intra-abdominal implantation in a user and adapted to hermetically seal off an attached intestine/organ while controlling mechanical stresses on the intestine/organ. For convenience hereinafter, "intestine/organ" may be referred to as "intestine". Optionally, hermetic sealing of the intestine substantially prevents leakage of body wastes (bowel content) and flatus through the stoma. Optionally, control of mechanical stresses on the intestine substantially prevents compression-related intestinal problems. Optionally, the device is adapted to substantially prevent Ostomy problems associated with intestinal movement such as stomal prolapse, stomal retraction, and hernia. Additionally or alternatively, the device is adapted to allow introduction of fluids into the intestine for irrigation, drug administration, nutrimental feeding, and the like. Optionally, peristaltic propelling of fecal contents may be done through the device.

According to some embodiments of the present invention, a use of a soft, flexible, and/or stretchable material such as, for example silicon rubber, natural rubber, or other elastomeric and/or polymeric materials in the device substantially prevents abrasion damage to the intestine. Optionally, usage of said soft, flexible, and/or stretchable material enables peristaltic propelling of fecal matter through the device. Optionally, the material is a biocompatible material. Optionally, the material is of a durometer in a range 1-100 Shore A, for example, 1-10 Shore A, 10-30 Shore A, 30-50 Shore A, 50-80 Shore A, 80-100 Shore A. Optionally, different portions of the device include materials of different durometer, for example a first portion may include a durometer in the range of 10-30 Shore A, and a second portion in the range of 50-80 Shore A.

According to some embodiments of the present invention, the containment device includes a sleeve adapted to be implanted in the abdominal cavity and surgically attached to a visceral surface of the abdominal wall. Optionally, the sleeve is attached on the peritoneum (a visceral side of it). Optionally, the sleeve is attached between the peritoneum and the transversalis fascia. Additionally or alternatively, the sleeve is attached inside the abdominal wall. Optionally, the sleeve is attached under the rectus sheet. Optionally, the sleeve is positioned so that a center of an opening at a proximal neck is substantially aligned with a center of a stoma in the abdominal wall. Optionally, the proximal neck includes a rounded cross-section. As used herein, the term "proximal" refers to a direction out of the body away from a center of the abdomen, and the term "distal" refers to a direction into the body towards the center of the abdomen.

According to some embodiments of the present invention, the sleeve is adapted to accommodate a closure assembly which may be inserted through the proximal neck for conducting the waste contents from the intestine, through the sleeve, and through the stoma to the outside of the body. Optionally, the closure includes a tubular shape. Optionally, the closure includes a non-circular cross-section, for example an elliptical cross-section. Optionally, the closure, in addition to serving as an interface between the intestine and the user, is adapted to keep the stoma closed, connect to a disposable waste content collection bag, separate waste content from skin around the stoma, enable flatus release, cover the stoma while providing an aesthetic appearance, allow a relatively easy approach to the stoma site, enable propelling of waste content through natural peristalsis, and/or enable bowel irrigation, or any combination thereof.

According to some embodiments of the present invention, the closure includes a distal section with a fixation element for substantially preventing relative movement between the closure and the sleeve when the closure is inserted in the sleeve. Optionally, the fixation element affixes the closure to the sleeve. Optionally, the fixation element, which may be for example an inflatable balloon, occupies a volume in a cavity in the sleeve. Optionally, the balloon occupies the volume in the sleeve cavity when fully inflated. Additionally or alternatively, the balloon occupies the volume in the sleeve cavity when partially inflated. Optionally, the balloon affixes the closure to the sleeve by pressing against a proximal portion of a cavity wall in the sleeve cavity. Optionally, pressing against a proximal portion of the cavity wall substantially minimizes mechanical stress on an intestinal tissue lying between the cavity wall and the fixation element.

According to some embodiments of the present invention, a compressive stress exerted by the balloon pressing the intestinal tissue against the proximal portion of the cavity wall is equal to or less than a colonic pressure. Optionally, the fixation element includes a pre-shaped elastomer suitable to fit inside the sleeve cavity and affix the closure to the sleeve while exerting the compressive stress on the intestinal tissue. Optionally, the fixation element includes an umbrella-like mechanism suitable to fit inside the sleeve cavity and affix the closure to the sleeve while exerting the compressive stress on the intestinal tissue.

In some exemplary embodiments, a compressive stress exerted by the inflated balloon on the intestine inside the sleeve cavity could be described by the following mathematical equation:

$$t_n = p \times R'^2_1 / (R_2^2 - R_3^2)$$

where p=a colonic pressure at a distal opening to the cavity, $t_n$=the compressive stress on the tissue, $R_2$=a radius at an apex of the cavity wall, $R_3$=a radius at a proximal opening of the sleeve cavity, and $R'_1$=the radius of the external surface of the stomal insert at the distal opening of the sleeve cavity, when full of waste content. Optionally, the compressive stress is less than 50 mmHg, less than 100 mmHg, less than 150 mmHg, less than 200 mmHg, less than 225 mmHg, less than 250 mmHg.

According to some embodiments of the present invention, the closure is adapted to be inserted from outside the body through the stoma into the sleeve, until the balloon is positioned inside the sleeve cavity. Optionally, the balloon is inflated when positioned inside the cavity. Optionally, the balloon is inflated by injecting an expansion fluid through a lumen or a tubule in the closure. Optionally, a predetermined volume of expansion fluid is used for inflation, for example by measuring the amount in a syringe or other measuring device prior to inflation. Optionally, an inflation system for the balloon includes a pressure-relief valve for allowing excessive expansion fluid to escape out of the balloon when the balloon pressure reaches the desired value. Additionally or alternatively, the balloon is of a non-stretchable material so that over-inflation requires relatively great effort. Optionally, the non-stretchable balloon is introduced into the closure in a collapsed state and inflated using the expansion fluid. Optionally, a pressure sensor on the proximal portion of the cavity wall, or on the balloon, senses when the compression stress reaches a predetermined value and sends a signal for stopping inflation of the balloon. Optionally, the predetermined value is less than or equal to 20 mmHg, less than 15 mmHg, less than 10 mmHg, less than 5 mmHg, less than 1 mmHg. Optionally, the balloon may be deflated by extracting the expansion fluid, allowing for removal and/or replacement of the closure.

According to some embodiments of the present invention, the fixation element circumscribes at least a portion of a circumference of the distal section of the closure. Optionally, the fixation element is located in another section of the closure, for example a mid-section or a proximal section. Optionally, the closure includes two or more fixation elements, each fixation element adapted to be inserted into a different sleeve cavity (for example, two fixation elements are fixed into two separate sleeve cavities). Optionally, the two or more fixation elements may be similar or dissimilar. Optionally, the two or more fixation elements are joined together as one fixation element including multiple bulges. Optionally, a use of two or more fixation elements allows for the force exerted by the bowel content on the closure (colonic pressure) to be distributed over the proximal portion of each cavity wall in each sleeve cavity. Additionally or alternatively, using two or more fixation elements reduces mechanical stress on the intestinal tissue as the compressive stress on the intestinal tissue is spread over a greater area. Optionally, increasing a number of fixation elements increases a hermetic sealing between the closure and intestinal tissue, as described further on below. Optionally, alternating between a plurality of fixation elements so that only one element applies pressure at a time maintains the closure anchored to the sleeve while allowing the intestinal tissue in the area of the removed pressure to recover from the previously exerted pressure, substantially preventing pressure injuries such as ischemia and necrosis, among others.

According to some embodiments of the present invention, the balloon is fabricated integrally as part of the closure and located at the distal end of the closure. Optionally, the balloon is located in another section of the closure, for example a mid-section or a proximal section. Optionally, during the assembly process of the closure, the balloon is flipped in a proximal direction. Optionally, the balloon is adapted to substantially resist collapse, thus eliminating the need to use a support between the balloon and the closure. Additionally or alternatively, the balloon has a cross-sectional "U" profile, with thick-wall distal and proximal portions and a thin-wall middle portion. Optionally, the thick-wall distal and proximal portions are adapted to resist collapse. Optionally, a shape of the balloon is configured to match the proximal portion of the sleeve cavity so that the mechanical stress exerted on the intestine is evenly distributed. Additionally or alternatively, the balloon is adapted to be inflated by an expansion fluid.

According to some embodiments of the present invention, the balloon includes a toroid shape with convex shaped sides for reducing mechanical stress on the intestinal wall by distributing the stress over a greater area. Optionally, the balloon includes attachment rims which extend outwardly from the balloon and are adapted to be adhered to stomal insert. Alternatively, the attachment rims do not extend outwardly from the balloon substantially limiting mechanical stresses being applied by the rims to the intestinal wall as contact between the rims and the wall is prevented.

According to some embodiments of the present invention, the sleeve cavity is annular in shape and includes a proximal opening and a distal opening of the first radius $R_1$, and the cavity wall between the two openings with the apex of the larger second radius $R_2$. Optionally, $R_1$ conforms to an external diameter of an attached intestinal portion when fecal content or flatus is passing through.

According to some embodiments of the present invention, the sleeve includes an opening at a distal neck through which a portion of the intestine (tissue) may be inserted into the sleeve cavity and passed through the sleeve towards the stoma. Optionally, the distal neck has a round cross-section. Optionally, a hermetic seal is formed between the intestine and the closure distal to the inflated balloon in the distal neck of the sleeve. Said hermetic seal is formed by configuring the dimensions of the closure and the sleeve in a way such that the annular void between the closure distal to the inflated balloon and the distal neck of the sleeve accommodates the intestine (tissue). Optionally, the annular void is of a width less than or equal to 10 mm (between the closure and the sleeve), less than 7 mm, less than 5 mm, less than 2 mm. The intestine in the said configuration fills the said void while having no or merely little unoccupied cavities in between. Optionally, the unoccupied cavities are of a characteristic dimension less than or equal to 1 mm, less than 0.5 mm, less than 0.1 mm, less than 0.05 mm. The intestine in the said configuration fills the void also without having the intestine pressed between the said surfaces of the closure and the sleeve. Optionally, a pressure on the intestine pressed between the two surfaces is less than or equal to 20 mmHg, less than 15 mmHg, less than 10 mmHg, less than 5 mmHg, less than 1 mmHg. Optionally, minute cavities existing between the intestine and the surface of the closure distal to the inflated balloon, or that spontaneously form there due to momentary movements of the tissue and the surfaces relative to each other, are occupied by mucus secreted by the intestinal mucosa. Optionally, the mucous filling provides a hermetic sealing with regard to solid and liquid body waste (the intestinal mucus is known in the art to spontaneously form a sealing barrier between adjacent intestinal surfaces).

In some exemplary embodiments, the inflated balloon pressing on the intestinal tissue forms a second hermetic seal. Optionally, a hermetic seal is formed between the closure and the intestine proximal to the inflated balloon, in the frontal neck area of the sleeve, similarly to the hermetic sealing that is formed between the intestine and the closure distal to the inflated balloon in the distal neck of the sleeve. Additionally or alternatively, the hermetic seal substantially prevents leaking of waste content and/or flatus out of the body through the stoma.

According to some embodiments of the present invention, the proximal neck is shaped such that sleeve cavity is substantially distant from the abdominal wall, for example, in a range from 1-15 cm, for example, 1.5-13 cm, 2-10 cm, 3-7 cm, 4-5 cm. Optionally, maintaining a substantial distance between the proximal neck and the abdominal wall relieves mechanical stresses which may act on the intestinal wall in the region where the intestine enters the abdominal wall.

According to some embodiments of the present invention, the sleeve includes a flexible flange, optionally a hernia mesh, which is affixed to the abdominal wall around the stoma for substantially preventing a parastomal hernia. Optionally, the flange is adapted to bend in more than one axis simultaneously, for example by an inclusion of a plurality of openings in the flange. Additionally or alternatively, the openings are slots. Optionally, the flange is adapted to be surgically attached to the abdomen, for example, by means of sutures, tackers, and the like. Optionally, the sleeve may be surgically attached, for example by suturing, to the intestine. Additionally or alternatively, the intestine may be fixed relative to the sleeve by means of the pressing of the inflated balloon of the closure. Additionally or alternatively, attaching the sleeve to the intestine and the flange of the sleeve to the abdomen substantially prevents stomal prolapse and/or stomal retraction. According to some embodiments of the present invention, the sleeve may be adapted to accommodate the mesentery. Optionally, the sleeve may be adapted to be placed over an existing ostomy. Optionally, the sleeve may be adapted to transmit a signal to an external device responsive to sensing of a high pressure, for example, in case of evacuation. Optionally, the signal may be an electrical signal and/or a mechanical signal.

According to some embodiments of the present invention, the sleeve includes gas release openings for releasing gases that might otherwise be trapped between the sleeve and the intestine. Optionally, the sleeve includes a stiffened proximal neck so as to prevent possible widening of the proximal neck and possible relative movement between the closure and the sleeve.

According to some embodiments of the present invention, the sleeve is adapted for use in a "loop" or "double barrel" ostomy. Optionally, the sleeve includes a hole (opening) in the flange. Optionally, the hole is connected to a margin of the flange by a slit. Optionally, in "double barrel ostomy" the sleeve is placed around the functional intestine and proximally attached to the abdominal wall and distally to the functional intestine. Additionally or alternatively, a non-functional intestine ("the mucus fistula") is brought through a hole in the abdominal wall back into the abdominal cavity. Optionally, the slit is adapted to accommodate bringing the non-functional intestine through the hole in the abdominal wall. Optionally, a length of the proximal neck is adapted to allow adequate space for the non-functional intestine between the sleeve's cavity and the abdominal wall.

According to some embodiments of the present invention, the sleeve is adapted for use in a temporary Ostomy. Optionally, the sleeve includes a narrow flange (instead of a wide flange as previously disclosed for some embodiments) with holes (openings) for anchoring the sleeve to the abdominal wall. Optionally, anchoring is by means of sutures, tacks, staples, or any other suitable surgical attachment method, or any combination thereof. Additionally or alternatively, the sleeve is placed around the intestine and proximally attached to the abdominal wall and distally to the functional intestine. Optionally, when removing the Ostomy, the surgeon pulls the intestine along with the sleeve outside the abdominal cavity through a hole cut in the abdominal wall. Optionally, the sleeve is then removed from the intestine by dissecting the sleeve.

According to some embodiments of the present invention, the containment device includes a stomal cover for covering the stoma from outside the body. Optionally, the stomal cover may be included in the closure. Optionally, the stomal cover is adapted to adjust to the topology of the skin around the stoma and/or to variations in abdominal wall thickness. Optionally, a protruding distance of the stomal cover in the proximal direction is relatively reduced. Additionally or alternatively, the stomal cover separates the evacuated content from the skin around the stoma so as to substantially prevent skin irritation due to the contact between the waste content and the skin.

According to some embodiments of the present invention, the containment device is adapted to release flatus. Optionally, flatus release is controlled by the user. Optionally, flatus is released by means of a flatus release valve. Optionally, the flatus release button includes an actuation button for creating an opening through which flatus may escape. Optionally, a lumen is adapted to transport flatus from within the closure to the flatus release valve. Optionally, the lumen is an irrigation lumen. Optionally, the irrigation lumen includes multiple openings through which the flatus can enter the lumen. Additionally or alternatively, the valve is adapted to allow water or any other fluid to be injected into the irrigation lumen for clearing up an obstruction in the lumen, for example an obstruction due to bowel content. Optionally, the valve is adapted to allow fluid to flow out from the closure through the valve. Optionally, the lumen for flatus transport is different than the irrigation lumen. Additionally or alternatively, flatus is released by loosening a cover between a cap (described further on) and the stomal insert or the stomal cover.

According to some embodiments of the present invention, a disposable waste content collection bag may be foldedly attached to the device. Optionally, the collection bag is hermetically attached to the closure. Optionally, the disposable waste content collection bag is arranged outside the stomal cover. Optionally, the bag is placed within the stomal insert and foldedly arranged into layers in an axial direction. Optionally, the bag is foldedly arranged inside the stomal insert into layers in the transverse direction. Additionally or alternatively, the bag is arranged inside the stomal insert with no order. Optionally, the bag is pushed by the user into the stomal insert up to a full length of the bag or in a folded configuration. Additionally or alternatively, the bag is included in a bag housing. Optionally, the bag housing is conical in shape to allow for a greater volume of space in which the bag may be folded. Additionally or alternatively, the conical bag housing allows for easier insertion of the housing into the proximal end of the closure. Optionally, the closure includes a conical shaped proximal end adapted to receive the conical shaped conical cap. Optionally, a discharge content indicator and/or a safety release valve in case of excessive body waste pressure may be included in the device.

According to some embodiments of the present invention, the waste content collection bag is unfurled by the pushing of the bowel content. Optionally, a portion of the bag is left unfurled for pulling by the user. Optionally, a strap or cord is attached to the bag, either at a proximal or distal end, for the user to pull on for unfurling the bag.

According to some embodiments of the present invention, the waste content collection bag includes a strand for closing the bag prior to disposal. Optionally, the strand is adapted to tie the bag along an upper portion of the bag. Optionally, the bag may be closed by a cap. Additionally or alternatively, the cap is placed on the upper portion of the bag. Optionally, the bag is closed by means of a clasp, a string, a tie, or any other means known in the art for closing the bag.

According to some embodiments of the present invention, a cap adapted to be attached to the stomal cover is further adapted to cover the folded collection bag. Optionally, the cap covers the furled bags. Optionally, the cap includes a hard cap cover. Optionally, the cap cover includes a flexible film. Optionally, the cap cover includes any other material suitable to cover the folded and/or furled bag. Additionally or alternatively, the cap cover is located at a proximal end of the cap. Optionally, the cap cover is located at a distal end of the cap.

According to some embodiments of the present invention, the containment device is adapted to communicate to the user of a need for evacuation. Optionally, the user is made aware of the need by a mechanism attached to the closure which is pushed in an outward direction (away from the closure) by the intestinal pressure. Optionally, the device includes a cap equipped with a flexible portion adapted to protrude (bulge) outwards when exposed to axial pressure exerted by bowel content or flatus. Optionally, the flexible portion is concave shaped. Optionally, the device includes a folded flexible cap adapted to partially or wholly unfold due to the axial pressure so that a proximal end of the cap protrudes outwards. Additionally or alternatively, the device includes a cap with a telescopic cover adapted to protrude outwards (bulge) when exposed to the axial pressure. Optionally, the telescopic cover is adapted to be retracted into the cap and to remain in that state when there is no axial pressure. Optionally, the cover is flushed with the cap. Optionally, the cover fits into the cap. Additionally or alternatively, an O-ring or other non-adhesive sealing mechanism is used to form a seal between the cover and the cap.

In some exemplary embodiments, the closure includes an inner balloon interconnected to an externally located balloon such that, in an equilibrium state, the inner balloon is inflated and the outer balloon is deflated. Optionally, pressure exerted by bowel content or flatus pushes and deflates the inner balloon, causing the outer balloon to inflate and externally protrude from the closure.

In some exemplary embodiments, the cap is equipped with a pressure sensor and an alarm mechanism adapted to warn the user when the colonic pressure inside the closure reaches or exceeds a predetermined value (due to bowel content and/or flatus). Optionally, the pressure sensor and/or the alarm are electrically operated. Optionally, the sensor and/or the alarm are located on the closure. Optionally, the alarm is an audible alarm. Optionally, the alarm is a vibratory alarm. Optionally, the sensor and/or the alarm are powered by a battery.

According to some embodiments of the present invention, the containment device includes a mechanism for blocking a proximal end of the closure while the waste content collection bag is being detached. Optionally, the blocking mechanism is used for an ileostomy for blocking bowel content fluid generally flowing out of the stoma. Optionally, the closure includes an internal balloon connected to an inflation port, the balloon adapted to allow bowel content flow out the closure to the collection bag when deflated, and further adapted to block bowel content flow out to the bag when inflated. Optionally, the inflation port is externally located on the closure. Additionally or alternatively, a user can replace the collection bag upon balloon inflation and blocking of bowel content flow. Optionally, the closure includes an internal normally-closed one-way valve which blocks bowel content flow out the closure, the valve adapted to be opened when a bag with a cannula is attached to the closure and the inserted cannula opens the valve. Optionally, withdrawal of the bag cannula closes the valve. Optionally, the closure includes a plurality of one-way valves for optional additional blocking. Additionally or alternatively, the internal valve is formed by a section of the wall of the closure which is shaped such that the closure is normally closed (no waste content flow) and open (waste content flow) upon insertion of the bag cannula. Optionally, the wall is collapsible and is pushed open by the bag cannula. Optionally, an external elastic clamp is used to block (close) the closure while the bag cannula is not inserted, the clamp adapted to open when the bag cannula is inserted into the closure, opening the closure. Alternatively, the clamp is manually opened by the user. Optionally, the clamp is adapted to close the closure when the bag cannula is removed.

According to some embodiments of the present invention, the containment device includes a safety mechanism for allowing release of bowel waste content from inside the closure when the colonic pressure reaches a predetermined value over a predetermined period of time. Optionally, the safety mechanism is included in the cap. Optionally, bowel content flow is through the stomal cover and through a release cover in the cap. Optionally, the cap includes a pressure-sensitive mechanism for opening the release cover. Optionally, the cover is ejected to allow for waste content flow. Optionally, the cover is adapted to be retracted into the cap once the waste content has been expelled or the colonic pressure has decreased below the predetermined value. Optionally, the cap is ejected by the pressure-sensitive mechanism. Optionally, so as to exclude false alarms due to temporary colonic pressure pulses, the mechanism releases the waste content for a colonic pressure inside the closure equal to or greater than 125 mmHg for a period of time, greater than 5 seconds, greater than 15 seconds, greater than 30 seconds, greater than 60 seconds, greater than 90 seconds. Optionally, the colonic pressure is greater than or equal to 150 mmHg, greater than or equal to 200 mmHg, greater than or equal to 225 mmHg, greater than or equal to 250 mmHg. Additionally or alternatively, the pressure-sensitive mechanism may include a mechanical system such as a "dashpot and spring" mechanism commonly referred to as "Kelvin-Voigt body" wherein the time response of the mechanism is determined by a spring constant, a number and size of holes in a piston and a viscosity of a fluid in a cylinder. Optionally, the mechanical mechanism includes a "Standard Linear Solid" system combining two different materials, for example an elastic material for an outer shell and a viscoelastic material of a "Kelvin-Voigt" or "Maxwell" type for an inner core, with a time response of the system set by appropriate selection of the materials. Optionally, an electrical pressure-sensitive mechanism is used including an electrical actuator for releasing the cover, a processing unit receiving data from a pressure sensor and sending an actuation signal to the electrical actuator. Optionally, a time response of the electrical mechanism is set through software in the processing unit. Optionally, the time response is set through hardware in the electrical mechanism.

According to some embodiments of the present invention, the stomal cover and the stomal insert may be fabricated separately, and attached during assembly. Optionally, the stomal insert has a constant cross-sectional shape. Optionally, the stomal insert is extruded. Additionally or alternatively, the stomal cover is attached to the outer surface of the stomal insert by bonding, welding, or other means known in the art for joining silicon rubber, natural rubber, or other elastomeric and/or polymeric materials. Optionally, a capping film is attached to the stomal cover and to a proximal end of an inflation lumen, leaving a space between them to form a lumen for inflation fluid to flow in. Optionally, a second capping film is attached similarly at an alternative location on the stomal cover for forming a lumen for the irrigation fluid to flow in. Optionally, a shape of the capping film and the stomal cover is such that a bulge is formed between them, the bulge serving as a control balloon inflating upon increase in a lumen pressure. Optionally, a one-way valve is installed in the lumen to permit inflation retention of the pressure in the balloon. Optionally, a one-way valve is installed in the irrigation lumen.

According to some embodiments of the present invention, the closure and/or stomal cover is adapted for use with numerous containment devices and artificial sphincters known in the art. Optionally, the closure is used without a waste collection system (without waste collection bag) and includes a cap attached to the closure by any known means such as, for example a bulge and a recess. Optionally, a seal is used between the cap and the closure. Optionally, the closure includes a connector adapted to accommodate numerous type of ostomy bags known in the art. Optionally, during continence, the closure is blocked by the cap and the cap is removed by the user for evacuation, at which time the user attaches the collection bag to the connector. Optionally, the cap and bag may be adapted for use with a plurality of devices that are affixed in the stoma (or in the anal canal) and contains a hollow catheter-like (or tube-like) portion which is inserted into the intestine for allowing body waste flow. Examples of devices known in the art include those disclosed in U.S. Pat. Nos. 2,544,579, 3,802,418, 4,030,500, 4,121,589, 5,569,216, 6,485,476 B1, 4,204,282, 6,033,390, 5,197,984, and WO 96/32904. Optionally, the stomal cover, cap and bag may be adapted for use in artificial sphincters that surround the intestine and compress it, for example, commercially available device "Acticon Neosphincter" of A.M.S., and device disclosed in U.S. Pat. Nos. 4,399,809, 4,619,245, 4,551,862, 4,634,443.

According to some embodiments of the present invention, the closure is introduced through the stoma and into the intestine using an introducer for easing the insertion of the closure. Optionally, the introducer manipulates the closure so that a cross-section of the closure's distal end becomes dense and folded. Optionally, the distal end is manually folded by a user. Optionally, the introducer is a device similar to a tweezers. Additionally or alternatively, the tweezers are inserted into the closure from the closure's proximal end, and moved until their end reaches the closure's distal end. Optionally, the distal end of the closure is then folded and held by the tweezers so that the closure's distal end cross-section is reduced.

According to some embodiments, the introducer includes a handle with a flexible, envelope distally located, the envelope adapted to be rolled. Optionally, the envelope is adapted to be pulled in a distal direction and turned "inside-out". Optionally, the envelope is shaped for easy insertion through the closure and/or the stoma opening. Optionally, the envelope includes a convex shaped distal end which is first inserted through the closure and/or stoma. Additionally or alternatively, the envelope is bullet-shaped.

According to some embodiments of the present invention, the containment device is adapted to be used for a new end-ostomy. Optionally, the new end-ostomy includes open surgery or laparoscopic surgery. Optionally, the containment device is adapted to be used for an existing end-ostomy. Optionally, the existing end-ostomy includes open surgery or laparoscopic surgery. Additionally or alternatively, the containment device is adapted to be used for a new loop-ostomy or "double barrel"-ostomy. Optionally, any of the said ostomy types is temporary.

According to some embodiments of the present invention, the containment device does not include a sleeve. Optionally, the closure is inserted into the intestine and is anchored in place by the fixation device inside the intestine. Optionally, use of containment device is advantageous as open surgery is not required for inserting the sleeve. Optionally, laparoscopic surgery is not required for inserting the sleeve. Optionally, the device is suitable for use where an internal pouch is created, for example, as may be in the case of continent ostomy.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Referring now to the drawings, FIG. 1 schematically illustrates a perspective view of an exemplary artificial Ostomy containment device 100, according to an embodiment of the present invention. Containment device 100 is adapted to provide hermetic sealing so that there is substantially no leaking of waste content or flatus from the intestine through a stoma. Optionally, containment device 100 is adapted to substantially prevent compression-related clinical problems while controlling evacuation of waste contents. Optionally, containment device 100 is adapted to substantially prevent clinical problems which may be associated with intestinal movement such as stomal prolapse, stomal retraction, parastomal hernia, and the like.

Containment device 100 includes an implantable sleeve 1 which may be intra-abdominally implanted in the user around the intestine and surgically attached to a surface of the abdominal wall, a removable closure 2 for conducting waste contents from the intestine through the sleeve and to the outside of the body (through the stoma in the abdominal wall), a disposable collection bag 3 hermetically connected to a proximal end of the closure for collecting waste content, and a cap 4 for covering the bag which is optionally tightly folded when empty of waste content. Sleeve 1 is adapted to be implanted in the abdominal cavity, optionally in the area of the intestine, and is geometrically shaped such that closure 2 may be affixed within the sleeve so that accidental withdrawal of the closure may be substantially prevented. Closure 2 is adapted to be distally inserted into the stoma from outside the body and affixed inside a sleeve cavity 5 in sleeve 1 by means of a fixation element, for example inflatable balloon 25, positioned at a distal section of the closure. Insertion of closure 2 is generally done with inflatable balloon 25 in a deflated or partially deflated state, the balloon inflated when positioned inside cavity 5. Optionally, the fixation element may be a preshaped elastomer or may include an umbrella-like mechanism. Optionally, the fixation element includes a toroidal shape. Once inflated to a predetermined pressure closure 2 is affixed to sleeve 1 so that there is no relative movement between them, substantially preventing undesired intestinal movement. Removal of closure 2 from sleeve 1 and proximal extraction from the stoma may be done by deflating, optionally partially deflating, balloon 25.

According to some embodiments of the present invention, sleeve 1 and closure 2, and optionally cap 4, may include a soft, flexible, stretchable material such as for example silicon rubber, natural rubber, or other elastomeric and/or polymeric material, or any combination thereof, adapted to substantially prevent abrasions to the intestine or other internal bodily organs. Optionally, the soft, flexible, stretchable material is adapted to allow peristaltic propelling of fecal contents through sleeve 1 and/or closure 2 as the material expands and contracts as the fecal content passes through. Optionally, the material is biocompatible. Additionally or alternatively, the material is of a durometer in a range 1-100 Shore A, for example, 1-10 Shore A, 10-30 Shore A, 30-50 Shore A, 50-80 Shore A, 80-100 Shore A. Optionally, portions of sleeve 1 and/or closure 2, and optionally cap 4, may include materials of different durometer ranges. Optionally, the soft material in sleeve 1 allows the sleeve to be inserted into the abdominal cavity and affixed to the abdominal wall by laparoscopic methods.

According to some embodiments of the present invention, sleeve 1 may include rounded edges, optionally a curved contour, for example, a circular cross-section, so that compressive stresses on internal organs and tissues are distributed over large areas, reducing localized stress and preventing mechanical damage. Optionally, visceral surfaces of sleeve 1 are non-adherent with respect to soft tissues substantially preventing adherence of intestine and/or internal organs and tissues to the sleeve. Optionally, closure 2 may include a cylindrical or tubular shape (rounded cross-section). Additionally or alternatively, visceral surfaces of closure 2 may be non-adherent to soft tissues.

Figure 2B:
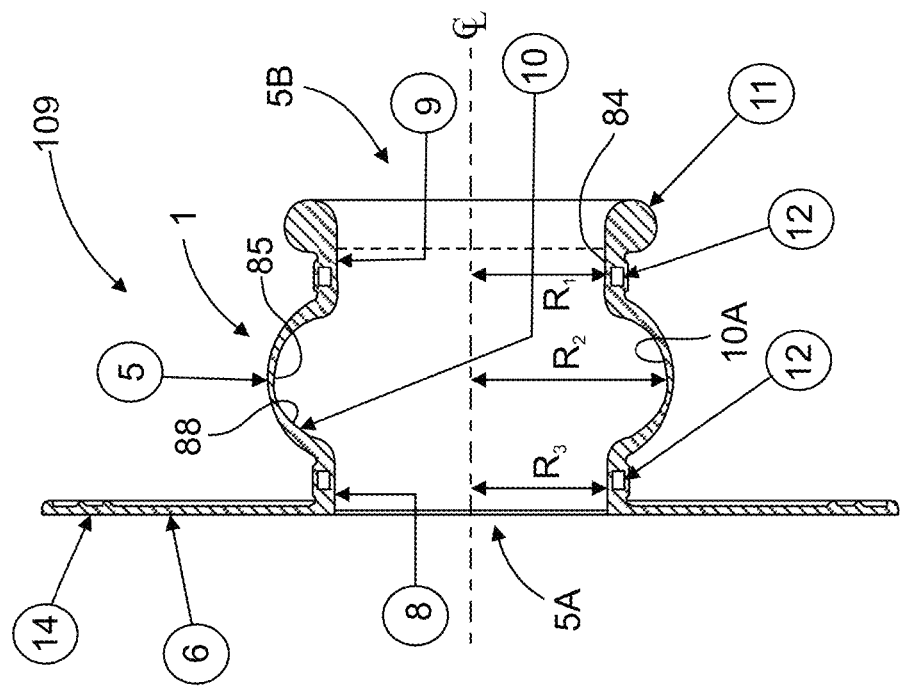
FIG. 2B schematically illustrates a sectional view of the sleeve, according to an embodiment of the present invention.
Figure 2A:
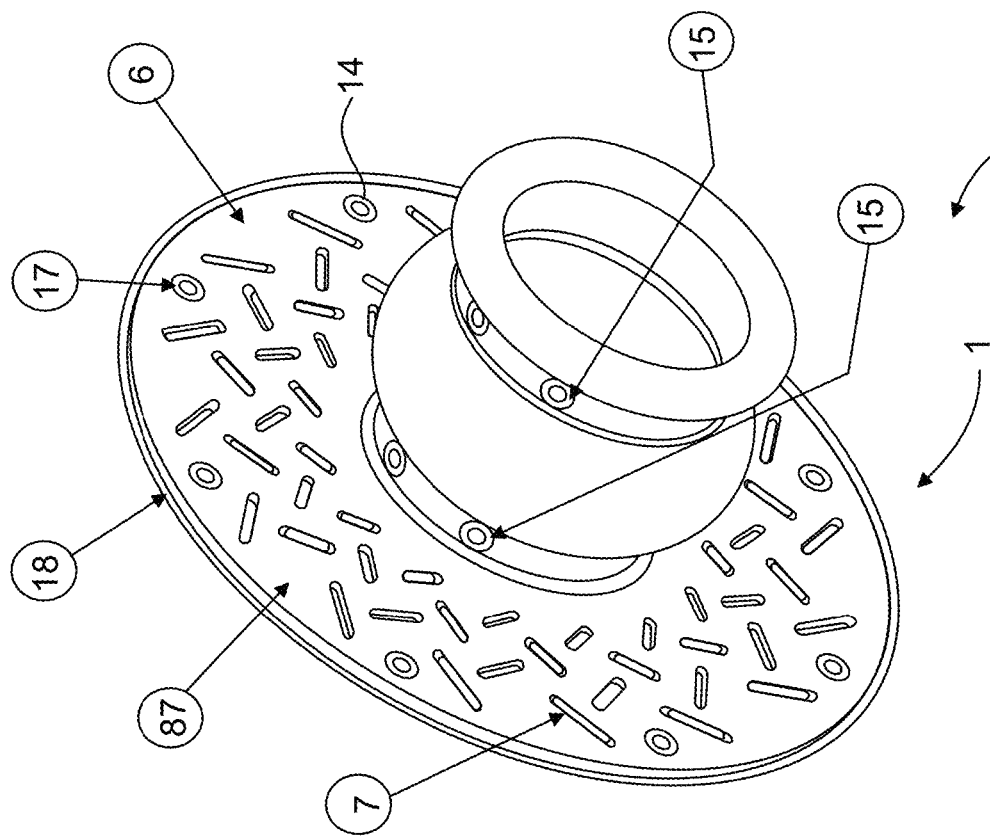
FIG. 2A schematically illustrates a detailed perspective view of the sleeve of FIG. 1, according to an embodiment of the present invention.
Figure 2C:
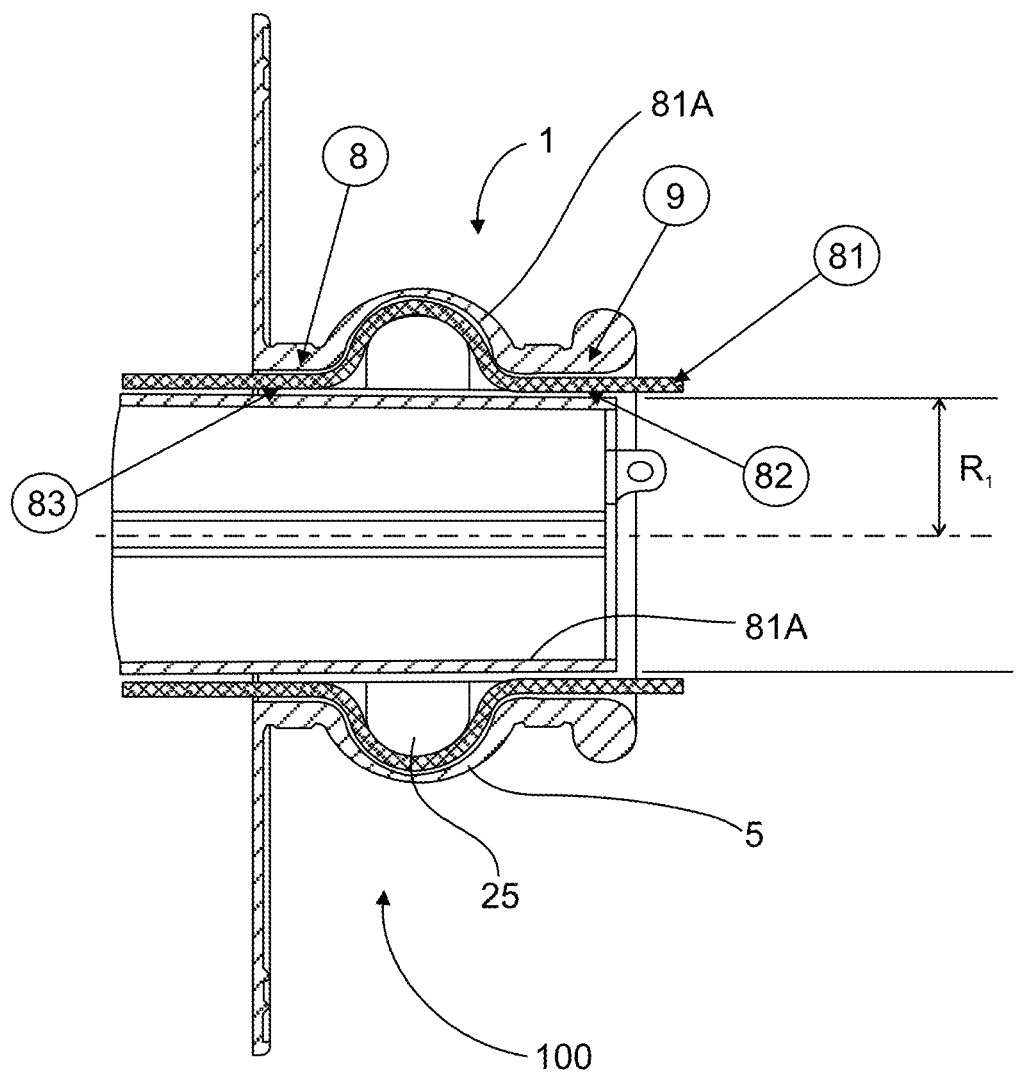
FIG. 2C schematically illustrates a sectional view of the sleeve with a distal section of a closure including a balloon inflated inside a sleeve cavity, according to an embodiment of the present invention.

Reference is now also made to FIG. 2A which schematically illustrates a detailed perspective view of sleeve 1, FIG. 2B which schematically illustrates a sectional view of the sleeve, and to FIG. 2C which schematically illustrates a sectional view of the sleeve with a distal section of closure 2 including balloon 25 inflated inside sleeve cavity 5, all according to an embodiment of the present invention. Sleeve 1 includes a proximal neck 8 which includes an opening 5A through which closure 2 is inserted into the sleeve; a distal neck 9 which includes an opening 5B through which an intestinal portion 81 is inserted and passes through the sleeve exiting through the proximal end for attachment to the stoma (optionally outside the body to the skin around the stoma); and sleeve cavity 5 between the proximal neck and distal neck for affixing the closure relative to the sleeve and for providing hermetic sealing. Optionally, openings 5A and 5B are circular. Optionally, sleeve 1 is attached to the visceral side of the abdominal wall such that a center of opening 5A is substantially aligned with a center of the stoma.

In some embodiments, proximal neck 8 is shaped such that sleeve cavity 5 is substantially distant from the abdominal wall, for example, in a range from 1-15 cm, for example, 1-13 cm, 2-10 cm, 3-7 cm, 4-5 cm. Optionally, maintaining a substantial distance between proximal neck 8 and the abdominal wall relieves mechanical stresses which may act on the intestinal wall in the region where the intestine enters the abdominal wall.

According to some embodiments of the present invention, distal neck 9 is cylindrically shaped and includes a cross-sectional radius $R_1$ (which may optionally be a radius of opening 5B). Optionally, $R_1$ may conform to a radius of the outer surface of a cross section of intestinal portion 81 entering sleeve 1 through distal neck 9, when full of waste content. Optionally, a rim 11 of distal neck 9 at opening 5B is rounded so as to substantially prevent concentrated stress on the intestine during body movements. Optionally, proximal neck 8 is cylindrically shaped. Additionally or alternatively, proximal neck 8 includes a cross-sectional radius similar to $R_1$ (which may optionally be a radius of opening 5A). Optionally, proximal neck 8 may include a radius $R_3$ different than $R_1$.

According to some embodiments of the present invention, sleeve cavity 5 is annular in shape and includes a cavity wall 10A which extends from an edge (a distal opening in the cavity) of distal neck 9 to an edge of proximal neck 8 (a proximal opening in the cavity). An apex 85 on cavity wall 10A is of a radius $R_2$. Optionally, $R_2$ may include an expanded radius of an outer surface of a cross section of intestinal portion 81 passing through sleeve 1 when fitted over inflated balloon 25. Optionally, $R_2$ is a maximum radius of sleeve cavity 5 and may conform to a maximum radius to which intestinal portion 81 may be cross-sectionally expanded by inflatable balloon 25 without causing damage to the portion. Optionally, cavity wall 10A may include a thin material (low durometer) adapted to allow cavity 5 to elastically expand in case of over-inflation of balloon 25, which may reduce a probability of mechanical damage to intestinal portion 81.

According to some embodiments of the present invention, closure 2 is positioned in sleeve 1 such that inflatable balloon 25 is inside sleeve cavity 5; a first section 83 in the closure, on a proximal side of the balloon, is positioned opposing proximal neck 8 in the sleeve; and a second section 82 in the closure, on a distal side of the balloon, is positioned opposing distal neck 9. Proximal neck 8 and distal neck 9 may have an axial length in a range from 2 mm-30 mm, for example 2-10 mm, 10-20 mm, 20-30 mm. Optionally, these axial lengths may include a safe area under which inflation of balloon 25 may result in an immediate pressure rise in an inflation lumen. Optionally, inflation of balloon 25 in an improper position, that is, when at least a portion of the balloon is positioned opposing proximal neck 8 or distal neck 9, is substantially prevented. Optionally, proper inflation is allowed when balloon 25 is wholly placed inside cavity 5.

In a typical application, intestinal portion 81 extends through sleeve 1 and is attached to the stoma. When closure 2 (with balloon 25 deflated or partially inflated) is inserted into sleeve 1 and positioned as previously described, first section 83 pushes an external wall of intestinal portion 81 against an internal wall of proximal neck 8, and second section 82 pushes the external wall of the intestinal portion against an internal wall of distal neck 9. This results in a hermetic sealing between an internal wall of intestinal section 81 and an external surface of closure 2. Optionally, first section 83 is cylindrically shaped. Optionally, second section 82 is cylindrically shaped. Optionally, second section 82 includes an external surface cross-sectional radius $R'_1$. Additionally, a hermetic seal is formed between intestinal portion 81 and closure 2 by inflating of balloon 25 which exerts a compressive force against a proximal section 10 of cavity wall 10A, optionally sealing off a waste content leakage path to the stoma. Furthermore, closure 2 is locked in position by a compressive force exerted on cavity wall 10 by balloon 25. The compressive stress exerted by balloon 25 on intestinal portion 81 may be determined by the following mathematical equation:

$$t_n = p \times R'^2_1 / (R_2^2 - R_3^2)$$

where p=intestinal pressure at the distal opening to the cavity (at opening 5B), $t_n$=the compressive stress on the tissue. Optionally, $R_2$=the maximum radius at the apex of the cavity wall, $R_3$ the minimum radius at proximal opening 5A to the sleeve cavity, and $R'_1$=the maximum radius of the external surface of section 82 of closure 2 at the opening 5B to the sleeve cavity, for determining a maximum compressive force which may be exerted on intestinal portion 81. Optionally, $R'_1$, $R_2$ and $R_3$ are selected so that the compressive stress does not cause any mechanical damage to the intestinal tissue between balloon 25 and proximal section 10 of cavity wall 10A. Additionally or alternatively, the compressive stress is less than 50 mmHg, less than 100 mmHg, less than 150 mmHg, less than 200 mmHg, less than 225 mmHg, less than 250 mmHg.

Figure 2D:
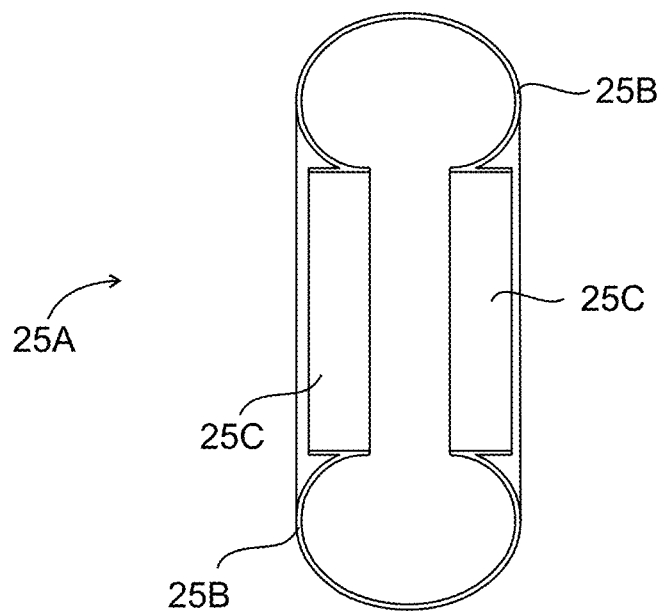
FIGS. 2D and 2E schematically illustrate cross-sectional views of exemplary fixation elements, according to some embodiments of the present invention.
Figure 2E:
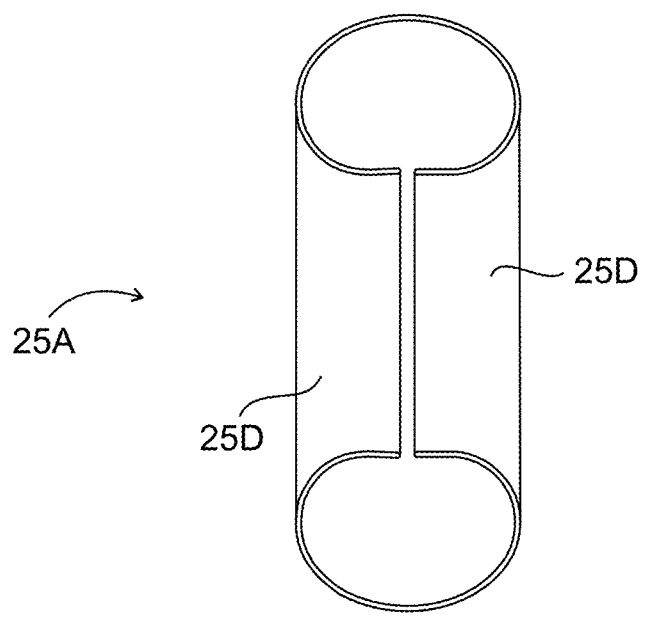

Reference is now made to FIGS. 2D and 2E which schematically illustrate cross-sectional views of a fixation element 25A, according to some embodiments of the present invention. Optionally, fixation element 25A is similar to that shown in FIG. 1 at 25, and may include an inflatable device such as a balloon.

In some embodiments, balloon 25A includes a toroid shape with convex shaped sides 25B as shown. Optionally, inclusion of convex shaped sides 25B in balloon 25A reduces mechanical stress on the intestinal wall by distributing the stress over a greater area. Optionally, balloon 25A includes attachment rims 25C which extend outwardly from the balloon and are adapted to be adhered to stomal insert 27. Alternatively, balloon 25A includes attachment rims 25D which do not extend outwardly from the balloon. Optionally, use of attachment rims 25D substantially limits mechanical stresses being applied by the rims to the intestinal wall as contact between the rims and the wall is prevented.

According to some embodiments of the present invention, cavity 5 may include a pressure sensor 88 adapted to transmit a signal, which may be a mechanical signal or an electrical signal, to an external device indicative of high pressure in the cavity. Optionally, the signal is an indication of a need for evacuation (of waste content). Optionally, pressure sensor 88 may be placed at one or more different locations in sleeve 1.

According to some embodiments of the invention, sleeve 1 includes a flexible flange 6, optionally a hernia mesh, adapted to be surgically attached to the abdominal wall around the stoma for substantially preventing a parastomal hernia. Flange 6 radially extends from a perimeter of opening 5A (in proximal neck 8) and includes openings 14 for attaching the flange to the abdominal wall by means of sutures. A flange rim 18 extends along a circumference of flange 6 to substantially protect the flange from possible tearing by the suturing thread, and possible releasing of sleeve 1 from the abdominal wall. Optionally, the sutures are protected by opening rims 17 encircling openings 14. Flange 6 may include slots 7 oriented in different directions which provide the flange with a flexibility to bend in more than one axis simultaneously. Additionally or alternatively, flange areas 87 between slots 7 may be used for inserting tackers, staples, and/or other suitable means for attaching flange 6 to the abdominal wall.

According to some embodiments of the present invention, suture openings 12 are included in proximal neck 8 and/or distal neck 9 for attaching sleeve 1 to intestine 81 by means of sutures. Optionally, a suture opening rim 15 encircles suture opening 12 for protecting sleeve 1 from possible tearing by the suturing thread, and possibly releasing of the sleeve from the intestinal tissue.

Figure 3B:
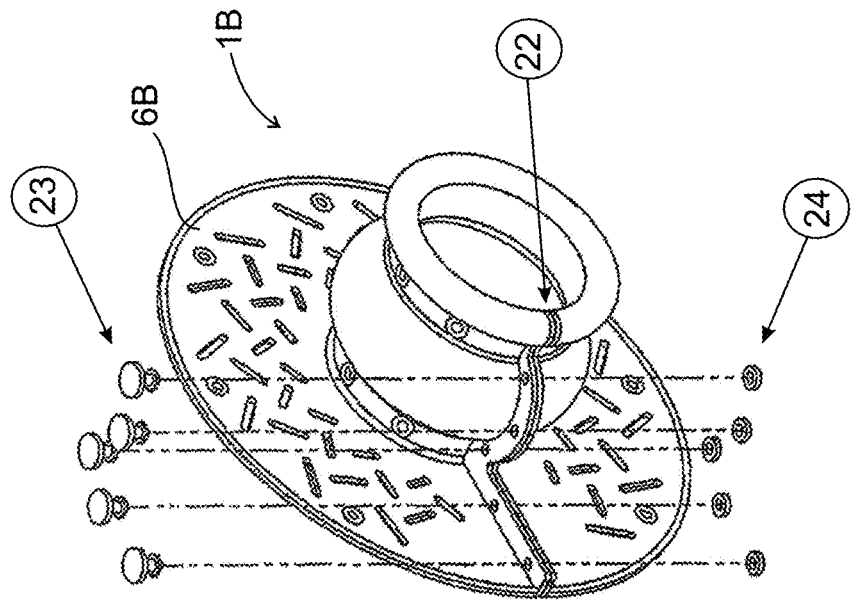
FIG. 3B schematically illustrates a perspective view of an exemplary sleeve adapted to be placed over an existing Ostomy, according to some embodiments of the present invention.
Figure 3A:
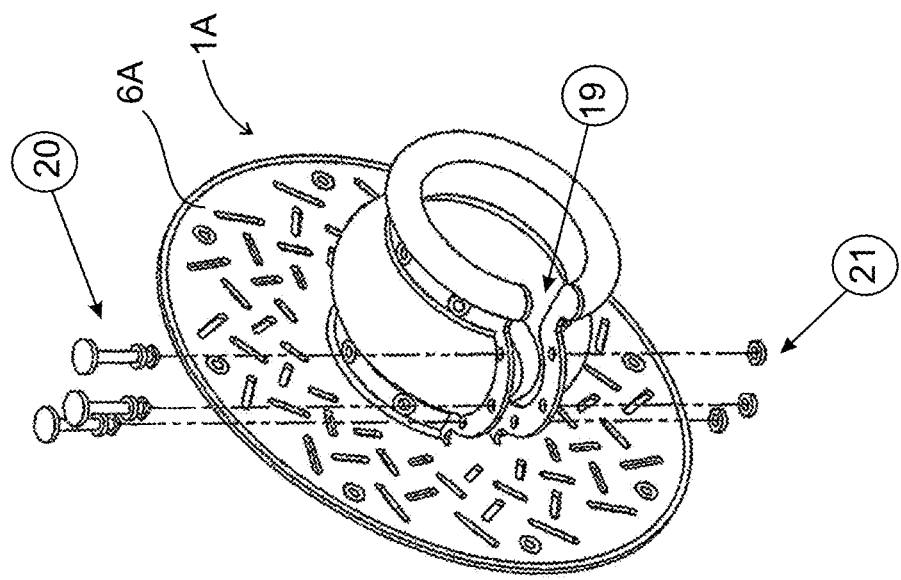
FIG. 3A schematically illustrates a perspective view of an exemplary sleeve adapted to accommodate a portion of a mesentery, according to some embodiments of the present invention.

Reference is now also made to FIG. 3A which schematically illustrates a perspective view of an exemplary sleeve 1A adapted to accommodate a portion of the mesentery, according to some embodiments of the present invention. Sleeve 1A may be similar to sleeve 1 in FIGS. 2A-2C with a difference that proximal neck 8, sleeve cavity 5, and distal neck 9, include an axial slot 19 of a width suitable to accommodate the mesentery (the axial slot extends a length of the sleeve to flange 6A which may be similar to flange 6 in FIG. 2A). The mesentery may be inserted in slot 19 and attached to sleeve 1 by male fasteners 20 which penetrate the mesentery from a first side and exit through a second side where they are received by female fasteners 21. Optionally, other suitable surgical attachment means (for example sutures) may be used as fasteners. A width of slot 19 may be varied according to geometry of the inflation balloon and sleeve 1A. Optionally, the width of slot 19 is uniform along the slot. Additionally, the width of slot 19 is of a substantially exact value.

Reference is now also made to FIG. 3B which schematically illustrates a perspective view of an exemplary sleeve 1B adapted to be placed over an existing ostomy, according to some embodiments of the present invention. Sleeve 1B may be similar to sleeve 1 in FIGS. 2A-2C with a difference that the sleeve includes a slit 22 which extends along a length of the sleeve, including a flange 6B, for opening the sleeve and placing over the existing Ostomy. Flange 6B is adapted to be attached to the visceral side of the abdominal wall, and may be similar to flange 6 shown in FIG. 2A except for slit 22. Once placed over the existing Ostomy, sleeve 1B may be closed by closing slit 22 with male fasteners 23 and female fastener 24. Optionally, slit 22 may be closed by any suitable surgical attachment means, for example, sutures, clips, wires, ties and the like, or any combination thereof.

Figure 4:
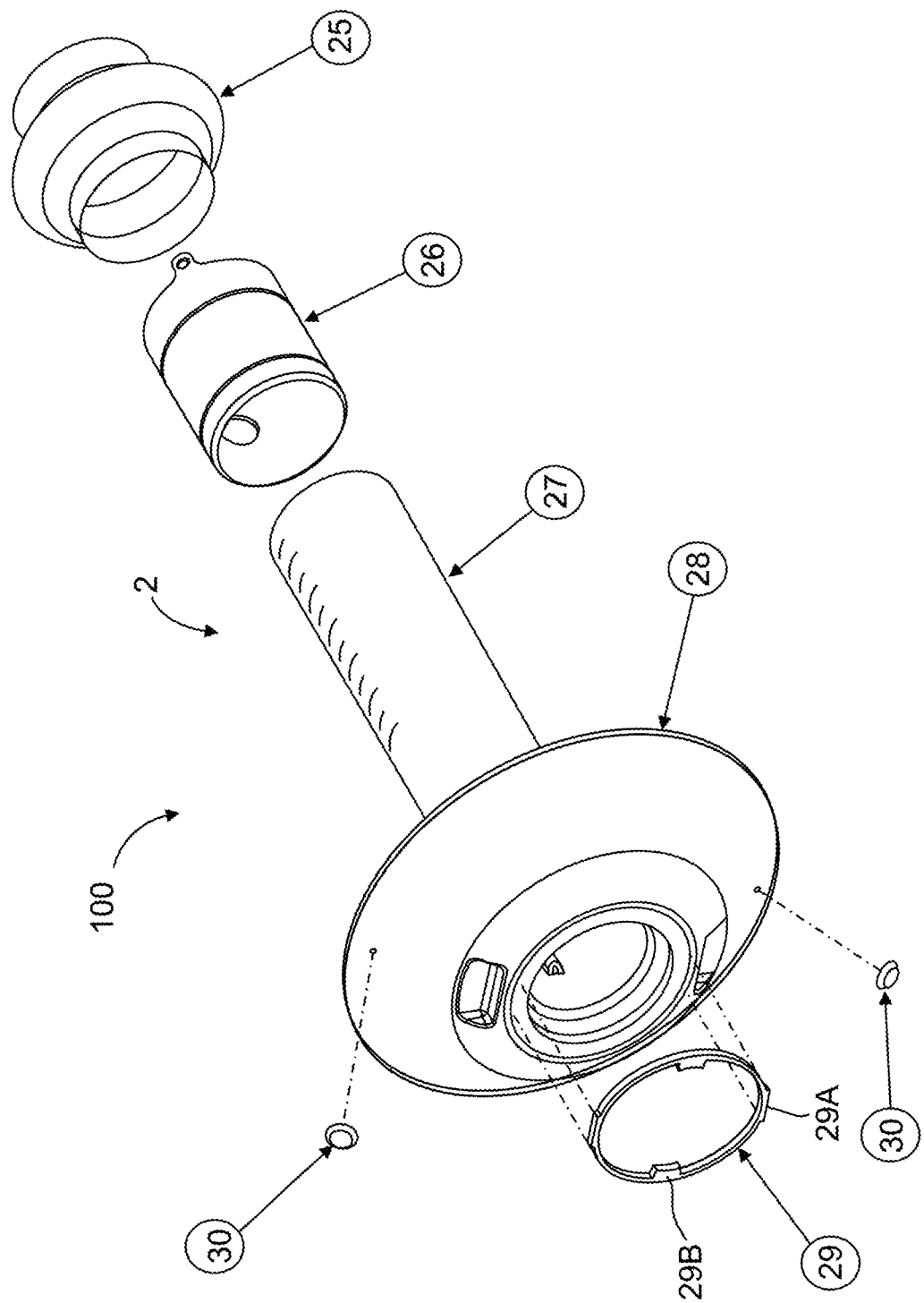
FIGS. 4 and 5 schematically illustrate isometric, partially exploded, views of the closure, according to an embodiment of the present invention.
Figure 5:
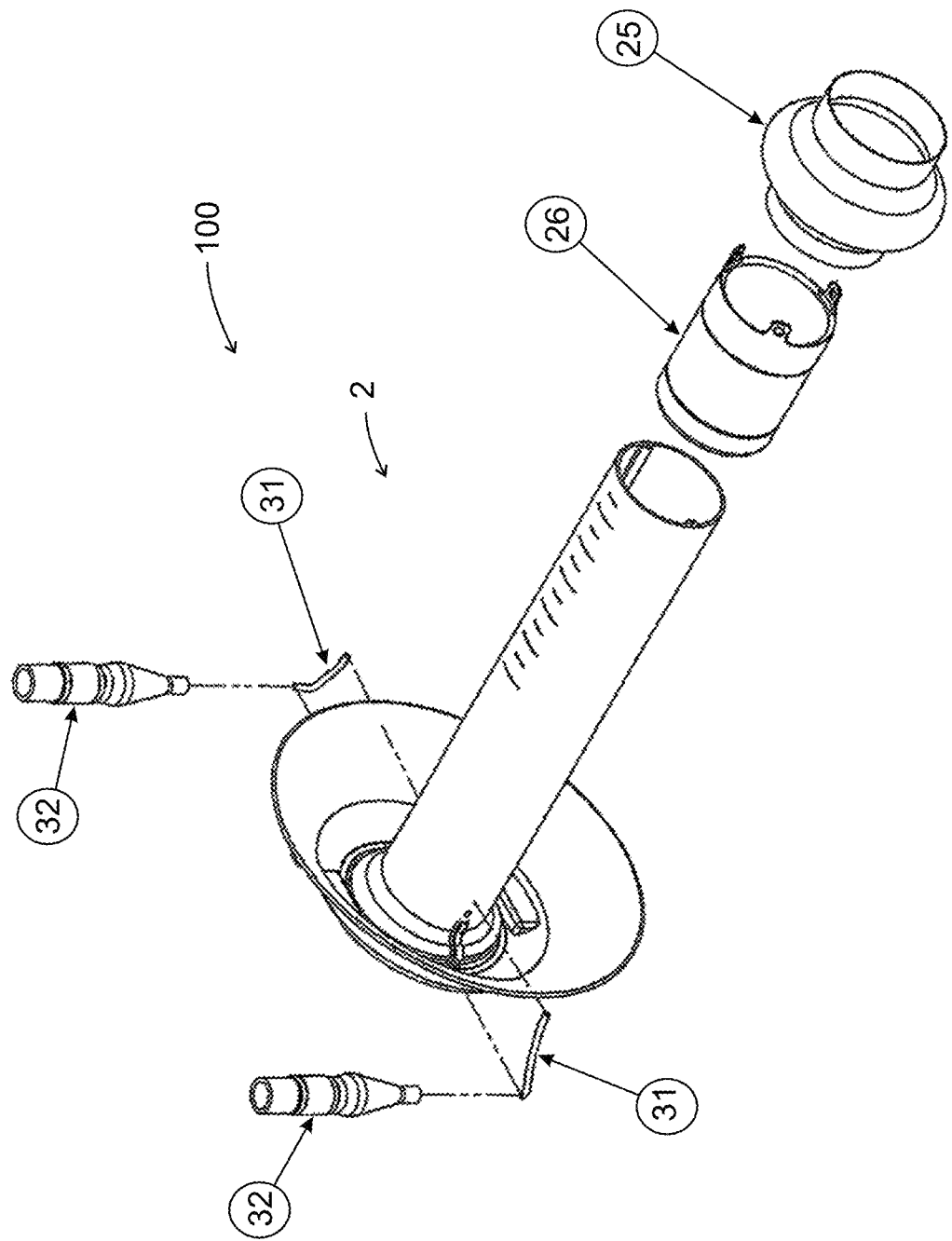

Reference is now also made to FIGS. 4-5 which schematically illustrate isometric, partially exploded, views of closure 2, and to FIGS. 6A and 6B which schematically illustrate perspective views of a stomal insert and a stomal cover in the closure, all according to an embodiment of the present invention. Closure 2 includes a stomal insert 27 which is inserted through the stoma into sleeve 1, and a stomal cover 28 which forms a part of a proximal section of the closure and covers the stoma on the outside of the body protecting the stoma from abrasion and providing an aesthetic view. Optionally, stomal cover 28 may include pressing points 34 for holding closure 2 when guiding stomal insert 27 into the stoma and into sleeve 1. Optionally, pressing points 34 are used for pressing on bag fastening mechanism 29 for releasing disposable collection bag 3 from closure 2. Optionally, stomal insert 27 and stomal cover 28 include two separate parts which are joined together by attachment mechanisms such as mechanical fasteners, interlocking mechanisms (for example, screwed together), adhesives, and the like. Optionally, stomal insert 27 and stomal cover 28 are a single integral component (manufactured in one piece).

Stomal insert 27 may be tubular in shape and includes inflatable balloon 25 at a distal section of the insert (and closure 2), the balloon adapted to provide a hermetic seal in sleeve cavity 5 when inflated. Optionally, balloon 25 is located in another section of stomal insert 27, for example in a middle section or a proximal section of the insert (and closure 2). Balloon 25 may circumscribe a cross-sectional circumference of stomal insert 27. Optionally, balloon 25 may circumscribe a portion of the cross-sectional circumference.

Inflating (and deflating) of balloon 25 may be done by injecting (removing) expansion fluid into (from) the balloon. Stomal insert 27 includes a hollow lumen or tubule 36 which extends the length of the insert to balloon 25 and is adapted to convey the expansion fluid in and out of the balloon. An inflation valve 32 may be connected to lumen 36 by means of a flexible, non-collapsible and/or kink-resistant first tube 31, the inflation valve attached to first tube 31 through stomal cover 28. Optionally, a first guide conduit 38 is used to guide first tube 31 through stomal cover 28 to a first opening 39 for connecting with lumen 36. Inflation valve 32 may be permanently attached to first tube 31, or temporarily attached when needed, and may be positioned outside stomal cover 28, optionally between the skin and the stomal cover. Deflating of balloon 25 is generally done when stomal insert 27 is to be removed from sleeve 1, for example when closure 2 is to be replaced, cleaned, maintained, during surgical procedures, and the like.

Stomal insert 27 optionally includes a second lumen 37 which extends the length of the insert and is adapted to convey fluids for irrigation of the intestine. Optionally, the fluid may be for nutrimental feeding, drug administration, and the like. Optionally, second lumen 37 serves as a conduit for flatus from the intestine to a flatus-releasing mechanism located outside the stoma (for example on the stomal cover). Optionally, the flatus-releasing mechanism includes a same valve 32 used to introduce irrigation fluids into the intestine. Optionally, a use of second lumen 37 for both irrigation and flatus release enables the user to inject fluid into the lumen for unblocking the lumen when blocked by bowel content. Optionally, second lumen 37 includes a plurality of openings within stomal insert 27, all connecting second lumen 37 with the lumen of stomal insert 27. A second tube 31 connects a second fluid administration valve 32 through which the fluid is administered into tube 37. Optionally, a second guide conduit 38 is used to guide second tube 31 through stomal cover 38 to a second opening 39 for connecting with lumen 37. Valves 32 may be differentiated from one another, for example by a different color or some other coding scheme, or by using a different connector in each valve.

Figure 6C:
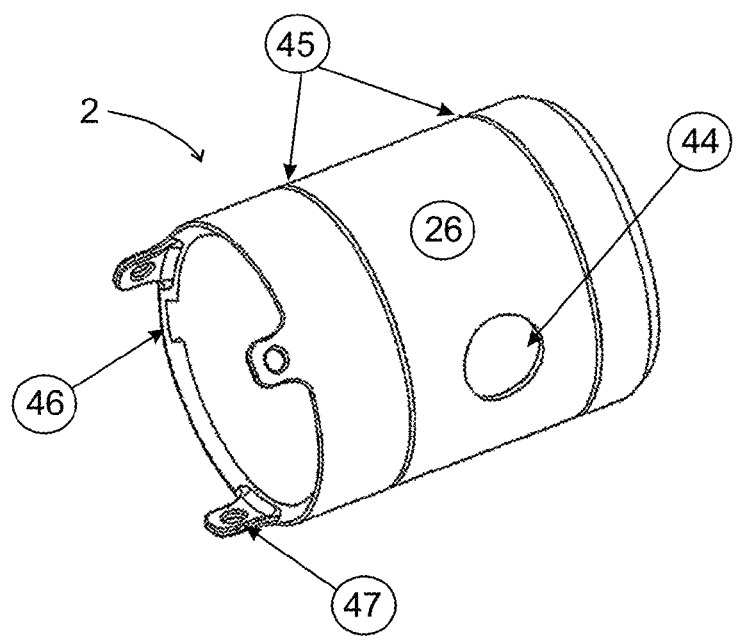
FIG. 6C schematically illustrates an isometric view of an exemplary support for a stomal insert, according to an embodiment of the present invention.

According to some embodiments of the present invention, the distal portion of stomal insert 27 where balloon 25 is positioned may be reinforced so as to prevent collapse of the stomal insert when the balloon is inflated, thereby allowing an open passage for the waste content to flow through. Optionally, reinforcement is provided by mounting at the distal section (at the location of balloon 25) a support 26, for example a bushing, of a material with greater rigidity than that of stomal insert 27. Reference is also made to FIG. 6C which schematically illustrates an isometric view of an exemplary support 26 for stomal insert 27, according to an embodiment of the present invention. Support 26 includes a balloon inflation hole (opening) 44 through which the expansion fluid flows into and out of balloon 25; notches 45 or optional markings for proper placement of the balloon on the support; an outlet 46 for fluid irrigation of the intestine; and fixation points 47 to which pins of an introducer tool may be affixed for relatively easy insertion and removal of closure 2 by compacting a cross-sectional diameter of the closure (see FIG. 29C). Optionally, the rigidity of support 26 may allow for the distal section (including the bushing) of stomal insert 27 to be compacted in size (for example by crumpling, twisting, and the like, with balloon 25 deflated) for relatively easy insertion of the insert through the stoma and into sleeve 1. Optionally, support 26 may be integrally included in stomal insert 27. Optionally, reinforcement may be provided by increasing a wall thickness of stomal insert 27 at the distal section. Optionally, reinforcement may be provided by including reinforcement rings or ribs in the walls of stomal insert 27 at the distal section where balloon 25 is located.

Figure 7A:
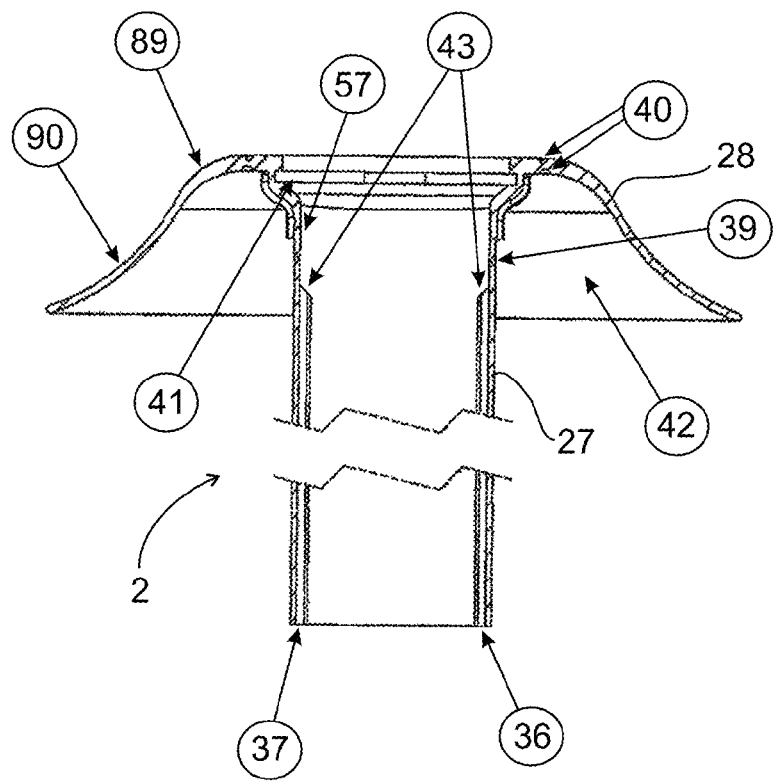
FIG. 7A schematically illustrates a cross-sectional view of the stomal cover and the stomal insert in the closure, according to an embodiment of the present invention.
Figure 7B:
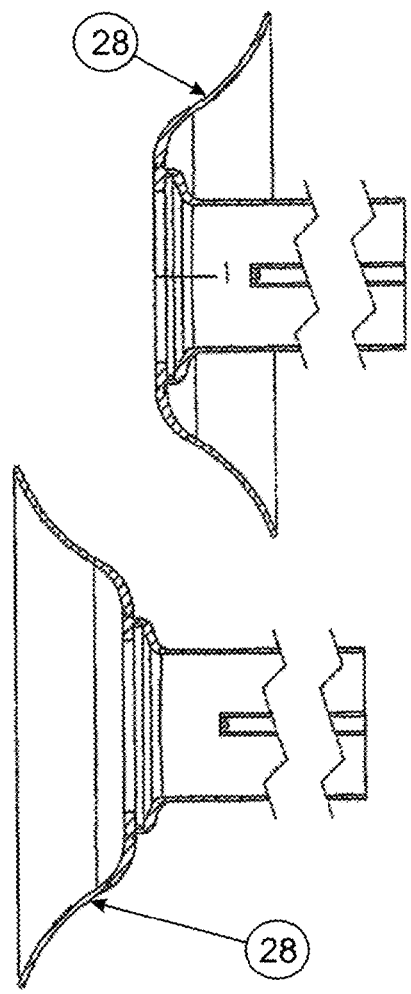
FIG. 7B schematically illustrates cross-sectional views of the stomal cover in a folded position for covering a stoma, and inverted for exposing the stoma, according to an embodiment of the present invention.
Figure 8:
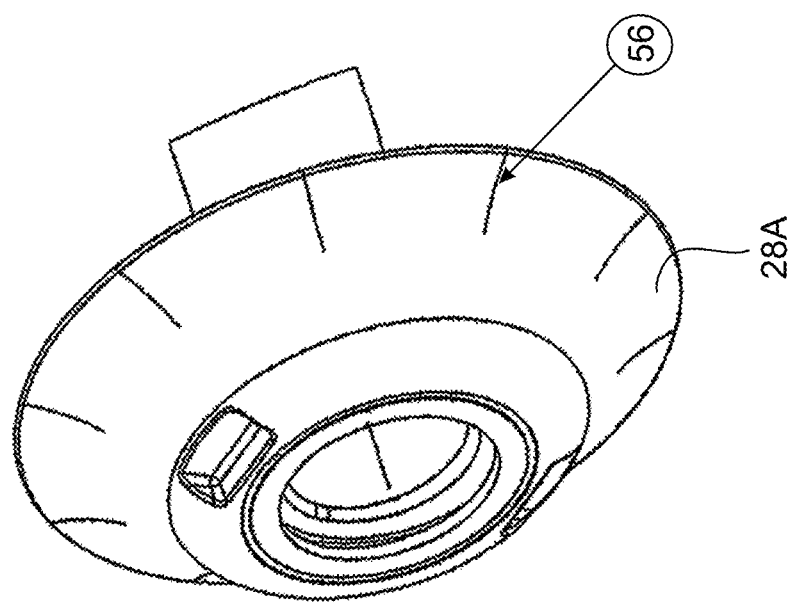
FIG. 8 schematically illustrates an isometric view of an exemplary stomal cover, according to some embodiments of the present invention.

Reference is now also made to FIG. 7A which schematically illustrates a cross-sectional view of stomal cover 28 and stomal insert 27 in closure 2, and to FIG. 7B which schematically illustrates cross-sectional views of the stomal cover in a folded position for covering a stoma, and inverted for exposing the stoma, according to an embodiment of the present invention. Stomal cover 28 may include a cap shape for maintaining a distance from the stoma including a convex section 89 adapted to create a hollow void 42 which provides this distance. Near a circumference (rim) of stomal cover 28, the stomal cover optionally includes a concave section 90 for enabling fine adjustment of the cover according to the topology of the skin and/or for adapting the stomal cover to variations in abdominal wall thickness, thereby allowing a substantially reduced distance to be maintained from the stoma. Optionally, adjustability of stomal cover 28 to the skin also prevents skin abrasion by the stomal cover and hence enhances the user's comfort. Optionally, stomal cover 28 may include wall recesses 40 which allow the cover to be inverted for allowing access to the stoma (see FIG. 7B). Shown in the figures are openings 43 to lumens 36 and 37 through which the expansion fluid and the irrigation fluid, respectively, enter the lumens from first and second tubes 31, respectively. Reference is now also made to FIG. 8 which schematically illustrates an isometric view of an exemplary stomal cover 28A, according to some embodiments of the present invention. Stomal cover 28A may be similar to stomal cover 28 in FIG. 7A with a difference that stomal cover 28A includes slits 56 which provide the cover with greater flexibility for improved attachment of the cover due to variations in the flatness of the skin around the stoma and/or variations in abdominal wall thickness.

Figure 9B:
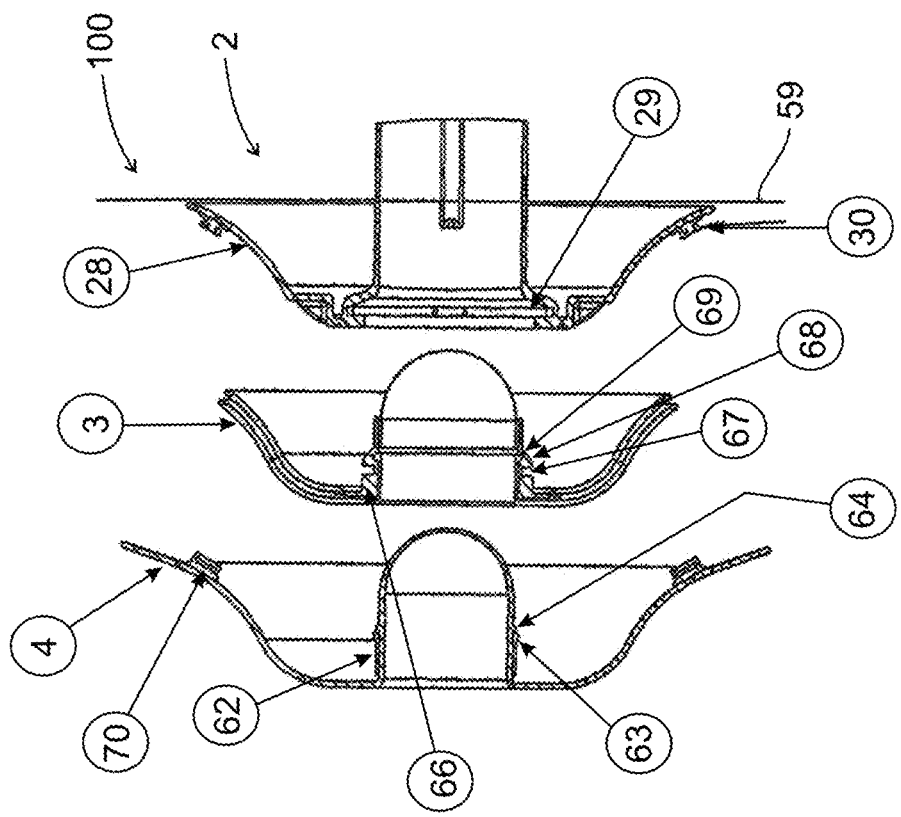
FIG. 9B schematically illustrates a partially exploded view of FIG. 9A, according to an embodiment of the present invention.
Figure 9A:
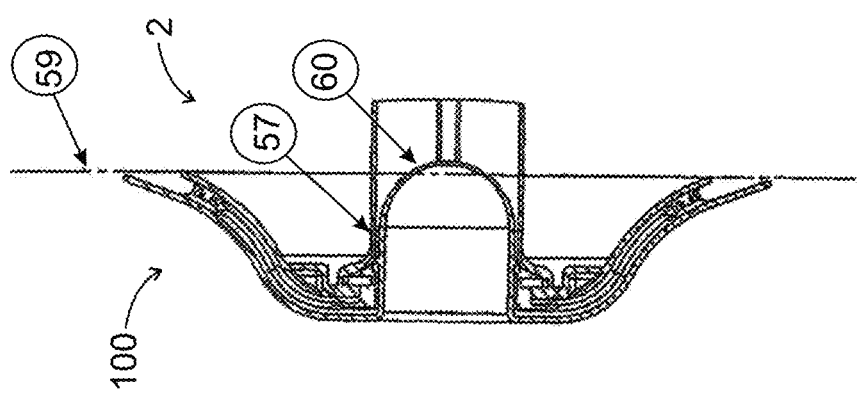
FIG. 9A schematically illustrates a cross-sectional view of a proximal end of the closure with a disposable collecting bag in a folded configuration attached to the stomal insert and covered by a cap, according to an embodiment of the present invention.

Reference is now also made to FIG. 9A which schematically illustrates a cross-sectional view of a proximal end of closure 2 with disposable collection bag 3 in a folded configuration attached to stomal insert 27 and covered by cap 4, and to FIG. 9B which schematically illustrates a partially exploded view of FIG. 9A, according to an embodiment of the present invention.

Figure 7C:
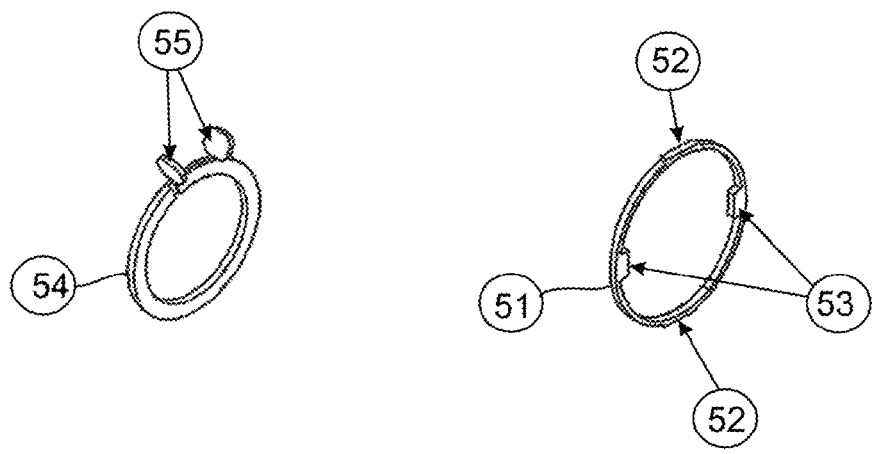
FIG. 7C schematically illustrates isometric views of exemplary bag fastening rings, in accordance with some embodiments of the present invention.

According to some embodiments of the present invention, stomal insert 27 includes a sealing area 57 in proximity to a proximal end of the insert for hermetically attaching disposable collection bag to the insert (for preventing leakage of waste content through stomal cover 28). Collection bag 3 is attached to stomal insert 27 by a fastening mechanism 29, which may be for example a round bag fastening ring, which includes ring slot protrusions 29A adapted to be inserted into a fastening ring slot 41 near the proximal end of the insert (for example, located at an edge of the stomal insert with stomal cover 28). Fastening ring 29 may be inserted by applying pressure to the ring (for example, by pressing with fingers) and guiding ring slot protrusions 29A in to ring slot 41. Optionally, fastening mechanism 29 may be screwed into sealing area 57. Optionally, fastening mechanism may be attached to sealing area 57 using a removable or a non-removable adhesive. Optionally, any other means for hermetically securing bag 3 to stomal insert 27 may be used. Bag fastening ring 29 may additionally include a bag fixation protrusion 29B unto which bag 3 are affixed. Optionally, to remove bag 3, the user presses pressing points 34 towards each other. Additionally or alternatively, protrusions 29A are pressed towards each other. Optionally, bag fixation protrusions 29B are pushed outwards, away from each other, and out of ring slot 67. Optionally, bag housing 66 can be withdrawn from sealing area 57. Reference is also made to FIG. 7C which schematically illustrates isometric views of other exemplary bag fastening rings, in accordance with some embodiments of the present invention. Bag fastening ring 51 may be similar to fastening ring 29 but may be oval shaped. Bag fastening ring 54 is a spiral shaped ring and includes knobs 55 for applying pressure to the ring for insertion into fastening ring slot 41. Optionally, an inner circumference of ring 54 seats in ring slot 67 affixing bag housing 66. To remove the bag, optionally, the user presses knobs 55 towards each other. Optionally, the overall perimeter of ring 54 increases so that an inner circumference of ring 54 is ejected from ring slot 67, and bag housing 66 may then be withdrawn.

In the figures, stomal cover 28 is shown outside the body and abutting abdominal wall 59. Optionally, the cover includes male fasteners 30 for attaching to female fasteners 70 on cap 4 securing the cap to stomal cover 28 and thereby to closure 2. Male fasteners 30 and female fasteners 70 may include a snap-button mechanism, a hook-loop fastener, an adhesive fastener, clips, or any other mechanism suitable for securing cap 4 to stomal cover 28.

According to some embodiments of the present invention, disposable collection bag 3 is arranged in the folded configuration and is attached to a bag housing 66 adapted to be received by stomal insert 27. Optionally, bag housing 66 may be a bushing. Optionally, bag housing 66 may be a rigid structure. Bag housing 66 may include a ring slot 67 adapted to be affixed to bag fixation protrusions 29B in bag fastening ring 29, a fixation rim 68 forming a rim for the ring slot and optionally shaped for guiding housing 66 into sealing area 57, and a cap fixation slot 69 adapted to receive a cap fixation protrusion 63 in cap 4 for locking between the cap and bag 3.

Reference is also now made to FIG. 9C which schematically illustrates various modes of attachment of bag 3 to housing 66, according to some embodiments of the invention. At 71, a rim at the opening of bag 3 is attached to housing 66 at welding area 72 by welding. Optionally, the rim is attached to housing 66 by bonding. Optionally, other attachment means suitable for joining two surfaces may be used. At 73, the rim at the opening of bag 3 is removably attached to a proximal end 74 of bag housing 66. At 75, the rim at the opening of bag 3 is removably attached to a distal end 76 of bag housing 66.

According to some embodiments of the present invention, cap 4 includes a cap housing 62 adapted to provide a rigid structure to the flexible cap and adapted to slidably fit into bag housing 66. When fitted inside bag housing 66 cap fixation protrusion 63 may latch unto cap fixation slot 69 in the bag housing. Cap 4 optionally includes a cap rim 64 for proper positioning of cap housing 62 onto cap 4. Optionally, cap rim 64 is included in cap housing 62, and fits into a corresponding slot in cap 4. Cap 4 may include a bell-shaped extension 60 which includes a thin-walled flexible sensation area for indicating a presence of waste content in stomal insert 27. Optionally, bell-shaped extension 60 is adapted to be pushed out in a proximal direction when exposed to pressure from the waste content (extension 60 is pushed outwards by the waste content). Additionally or alternatively, bell-shaped extension 60 is included as part of closure 2. Optionally, other methods for detecting waste content presence may be used, which may include electrical sensing as previously described, or mechanical sensing other than that described herein.

Figure 9D:
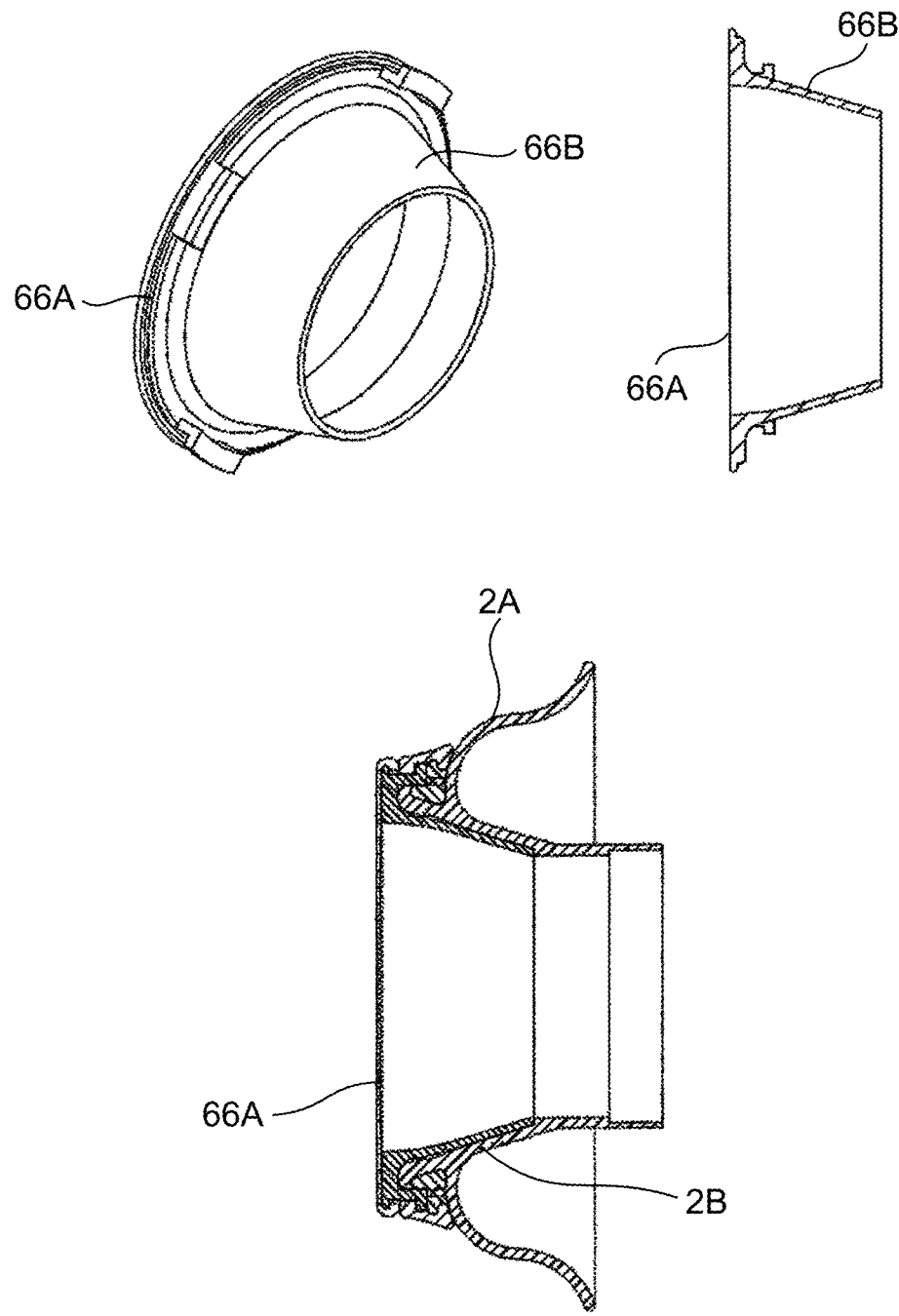
FIG. 9D schematically illustrates an exemplary waste content bag housing, according to some embodiments of the present invention FIGS. 10A and 10B schematically illustrate cross-sectional views of the closure prior to deployment of the bag during an evacuation process, and following deployment of the bag during the evacuation process, respectively, all according to some embodiments of the present invention.

Reference is now also made to FIG. 9D which schematically illustrates an exemplary bag housing 66A, according to some embodiments of the present invention. Optionally, bag housing 66A is similar to that shown in FIG. 9B at 66, with the difference that bag housing 66A is conically shaped and includes sloping walls 66B. Optionally, use of sloping walls in conical bag housing 66A provides for an increased volume for storing bag 3 compared to use of non-sloping walls as in bag housing 66. Optionally, use of sloping walls in conical bag housing 66A provides for easier insertion of bag housing 66A into in the proximal end of closure 2A. Optionally, conical bag housing 66A can be used with a closure 2A which includes sloping walls 2B at the proximal end for properly receiving the bag housing when inserted. Optionally, closure 2A is similar to closure 2 with the difference that closure 2A includes sloping walls 2B. Optionally, conical bag housing 66A is attached to closure 2A using a twist-and-lock mechanism, a snap-lock mechanism, or other type of attachment mechanisms which may include any of those previously disclosed, or any combination thereof.

Reference is now also made to FIGS. 10A and 10B which schematically illustrate cross-sectional views of closure 2 prior to deployment of bag 3 during an evacuation process, and following deployment of the bag during the evacuation process, respectively, all according to some embodiments of the present invention. Extension 60 in cap 4 is pushed out by pressure exerted by a waste content 77 inside stomal insert 27. The user feels (or sees) extension 60 pushed outwards and proceeds to remove cap 4. Once cap 4 is removed, waste content 77 pushes on bag 3 deploying the bag and the waste content may fall into the bag.

Figure 11:
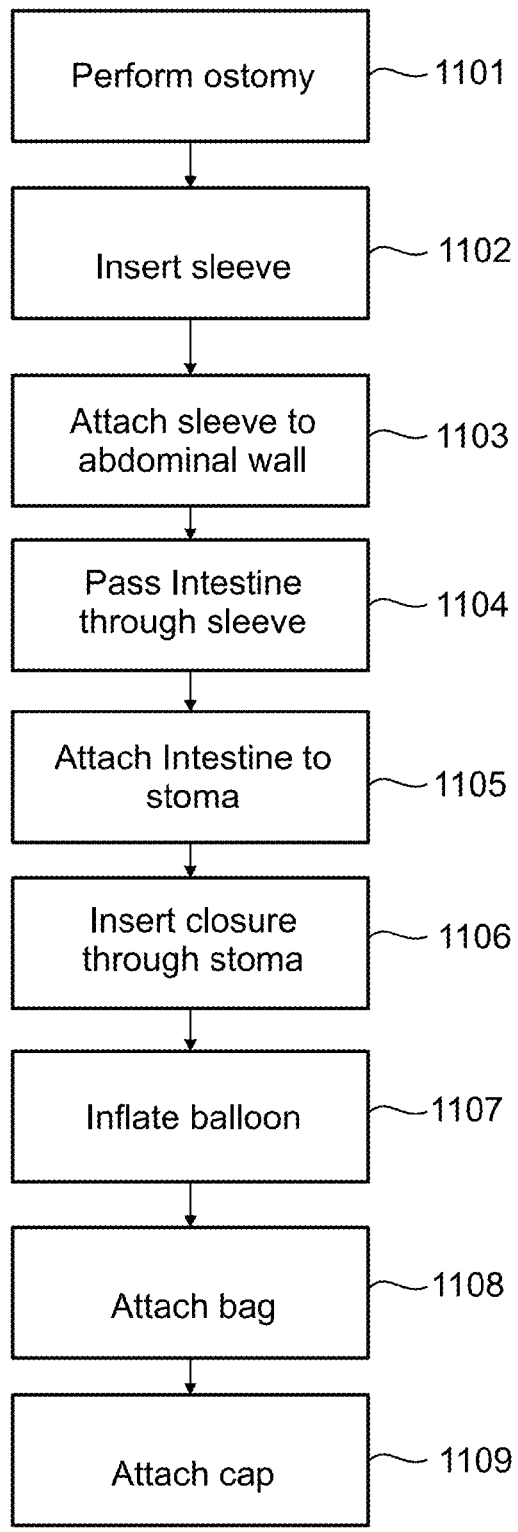
FIG. 11 illustrates a flow chart of a method for providing body waste continence using the Ostomy containment device, according to an embodiment of the present invention.

Reference is now made to FIG. 11 which illustrates a flow chart of a method for providing body waste continence for a person with an end-ostomy using artificial Ostomy containment device 100, according to an embodiment of the present invention. The method illustrated and described herein is not intended to be limiting in any way, and an ordinary person skilled in the art may find that there are numerous other ways of implementing the method.

Optionally at 1101, a surgeon performs an Ostomy on a patient and removes a portion of the intestine leaving the healthy intestine. Optionally, the Ostomy may be a colostomy, an ileostomy, or a urostomy.

Optionally at 1102, the surgeon measures, using methods known in the art, a perimeter and/or a diameter of the end of the healthy intestine. Optionally, the surgeon selects sleeve 1 of proper diameter and introduces the sleeve into the abdominal cavity of the patient undergoing the Ostomy.

Optionally at 1103, the surgeon attaches sleeve 1 to the visceral side of the abdominal wall. Optionally, the surgeon may attach sleeve 1 to the visceral side of the peritoneum, or to the exterior side of the peritoneum, or in between the abdominal fascia, or in any other location known in the art as proper for attaching a hernia mesh. Optionally, a center of opening 5A in proximal neck 8 is aligned with a center of the stoma. The attachment may include the use of sutures through suture openings 17 in flange 6. Optionally, the surgeon may use tackers, staples or any other suitable means of attachment, inserted through flange areas 87.

Optionally at 1104, the surgeon passes intestinal portion 81 through sleeve 1 by inserting the intestinal portion through opening 5B in distal neck 9, through sleeve cavity 5, and exiting through opening 5A in proximal neck 8.

Optionally at 1105, the surgeon attaches intestinal portion 81 to the stoma (optionally, to the skin around the stoma on the outside of the body of the patient).

Optionally at 1106, the surgeon measures a thickness of the abdominal wall. Optionally, the surgeon measures a required length of closure 2 required using markings 33 on stomal insert 27 as reference and cuts the insert to the required length. Optionally, other means of measuring known in the art may be used, for example a measuring tape, a stoma measuring device, and the like. Optionally, the cut is along a marking 33, or between two markings. Optionally, the surgeon then attaches support 26 to stomal insert 27, followed by attachment of deflated balloon 25. Assembled closure 2 is inserted by the surgeon through the stoma and into sleeve 1. Additionally or alternatively, closure 2 arrives from factory fully assembled, including support 26, and in different lengths. Optionally, the surgeon measures the thickness of the abdominal wall, and selects closure 2 of an appropriate length. Optionally at 1107, the surgeon adjusts a position of closure 2 such that balloon 25 is inside sleeve cavity 5. Optionally, the surgeon may remove closure 2 from the stoma and sleeve 1 to further reduce a length of stomal insert 27. Once properly positioned, the surgeon may inflate balloon 25 by introducing an expansion fluid through valve 32 which flows through lumen 36 into the balloon. Closure 2 is now affixed to sleeve 1 and there is substantially no relative movement between them. Additionally, closure 2 is hermetically attached to intestine portion 81 substantially preventing leakage of waste content and/or flatus. Optionally, if the surgeon wishes that during a healing period of the stoma no forces would be applied to the intestine, then steps 1107 through 1109 may be conducted on a later stage.

Optionally at 1108, bag 3 is attached to closure 2 by inserting bag housing 66 into sealing area 57 in stomal insert 27. Bag fastening ring 29 is then attached to ring slot 41 in stomal insert 27, locking bag 3 and bag housing 66 in place, and providing a hermetic seal for transferring waste content from the insert to the bag without leakage. Optionally, bag fastening ring 29 is assembled onto closure 2 in factory.

Optionally at 1109, cap 4 is attached to stomal cover 28 by mating female fasteners 70 on the cap with male fasteners 35 on the stomal cover. Cap housing 62 is slidingly inserted in bag housing 66 and bag fixation protrusion 63 latches unto bag fixation slot 69 in the bag housing. Extension 60 projects in a distal direction for sensing pressure from waste content in stomal insert 27.

Figure 12:
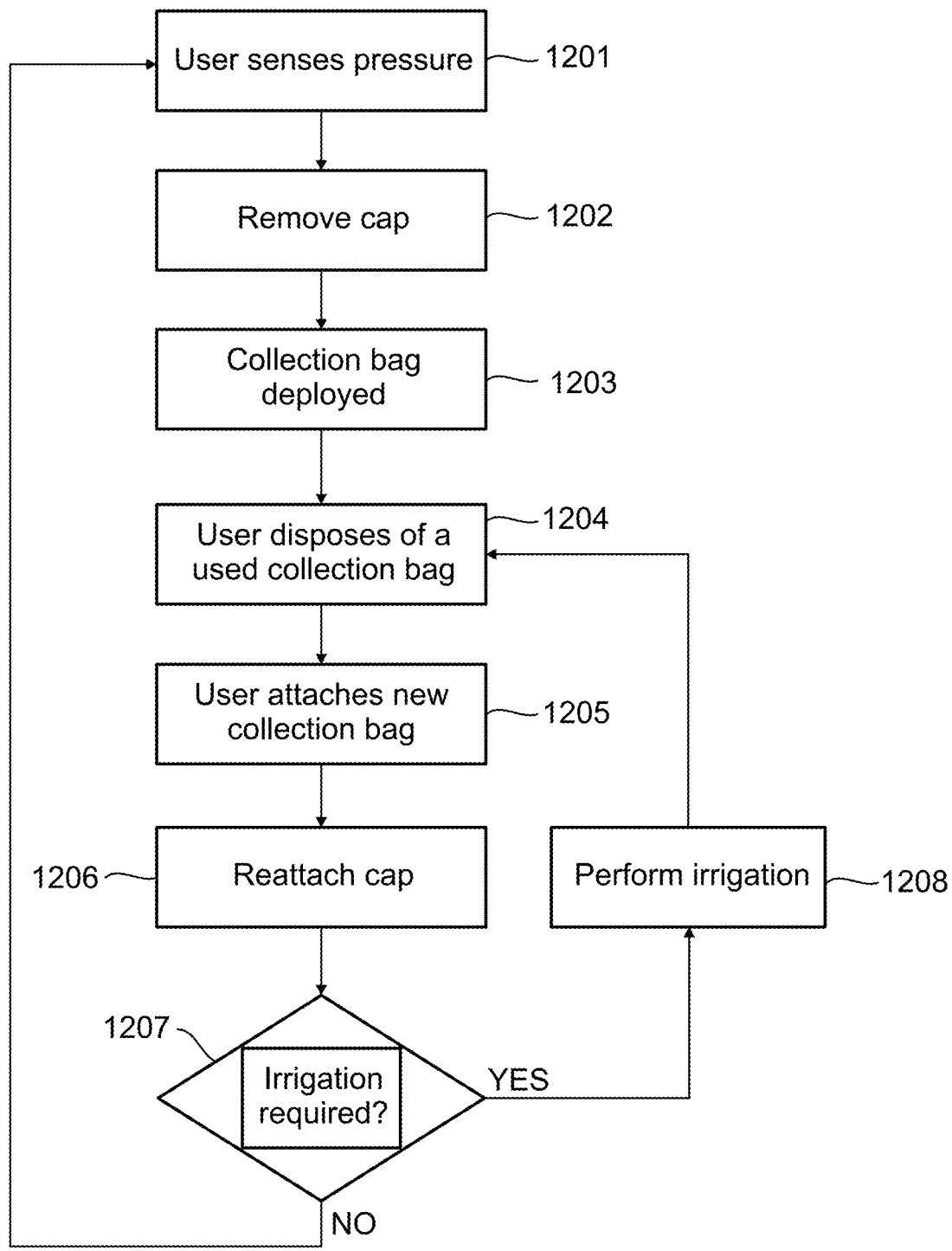
FIG. 12 illustrates a flow chart of a method for using the Ostomy containment device, according to an embodiment of the present invention.

Reference is now made to FIG. 12 which illustrates a flow chart of a method for using artificial Ostomy containment device 100, according to an embodiment of the present invention. The method illustrated and described herein is not intended to be limiting in any way, and an ordinary person skilled in the art may find that there are numerous other ways of implementing the method.

Optionally at 1201, the user, during the course of the day, senses pressure from waste content which requires evacuation. Optionally, the pressure is sensed through extension 60 which is forced by the waste content to protrude from cap 4 in a proximal direction. Optionally, the pressure is sensed by an electrical signal or a mechanical signal received from sensor 88.

Optionally at 1202, the user removes cap 4.

Optionally at 1203 folded bag 3 is deployed allowing the waste content to flow into the bag. Optionally, the user deploys bag 3 using a strap or cord that is attached to the bag, or any other method suitable for deployment of the bag.

Optionally at 1204, a user having finished evacuation replaces disposable collection bag 3 which includes the waste content. The user optionally releases bag housing 66 from bag fastening ring 29 by removing fixation protrusions 29B in the fastening ring from ring slot 67 in the bag housing. The user then disposes of the used collection bag.

Optionally at 1205, the user attaches a new folded bag 3 together with its housing 66 to stomal insert 27. The user attaches housing 66 in new bag 3 to bag fastening ring 29 by inserting fixation protrusions 29B in the fastening ring to ring slot 67 in the bag housing.

Optionally at 1206, the user reattaches cap 4 to stomal cover 28 by inserting cap housing 62 into bag housing 66 and attaching male fasteners 30 on the stomal cover to female fasteners 70 on the cap.

Optionally at 1207, the user, during the course of the day, may require irrigation. If irrigation is required continue to 1208. If irrigation is not required, go to 1201.

Optionally at 1208, the user connects an irrigation fluid source to fluid administration valve 32. Optionally, Irrigation may require the removal of bag 3 and installation of a different bag of higher capacity (due to the volume of the irrigation fluid which also has to be collected). The user removes cap 4 deploying bag 3 and opens the valve. Irrigation fluid flows through lumen 37 in closure 2 into intestine 81, washing out the intestine. The washed out waste content flows into bag 3. Optionally, the user may introduce the irrigation fluid and allow the fluid to remain inside the bowel for some time, and only then remove cap 4 for allowing bowel content flush out. Once finished irrigating, go to 1201.

Figure 13A:
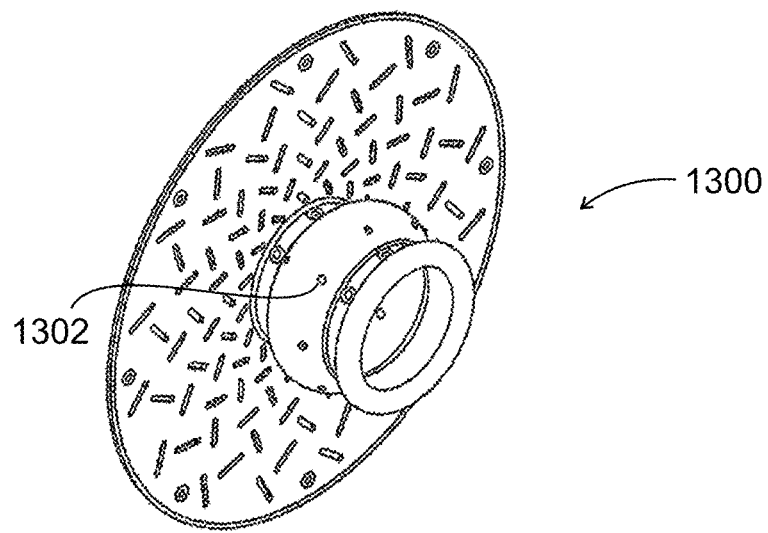
FIGS. 13A-13D schematically illustrate exemplary sleeves, according to some embodiments of the present invention.

Reference is now made to FIG. 13A which schematically illustrates an exemplary sleeve 1300, according to some embodiments of the present invention. Optionally, sleeve 1300 includes gas release openings 1302 for releasing gases which may otherwise be entrapped between the sleeve and a closure. Openings 1302 may include a circular shape; a non-circular shape, for example elliptical or rectangular; or any combination thereof. Sleeve 1300 may be similar to that shown in FIG. 2A at 100 with a variation that sleeve 1300 includes openings 1302. Optionally, sleeve 1300 may be similar to other embodiments disclosed herein this disclosure with the mentioned variation(s).

Figure 13B:
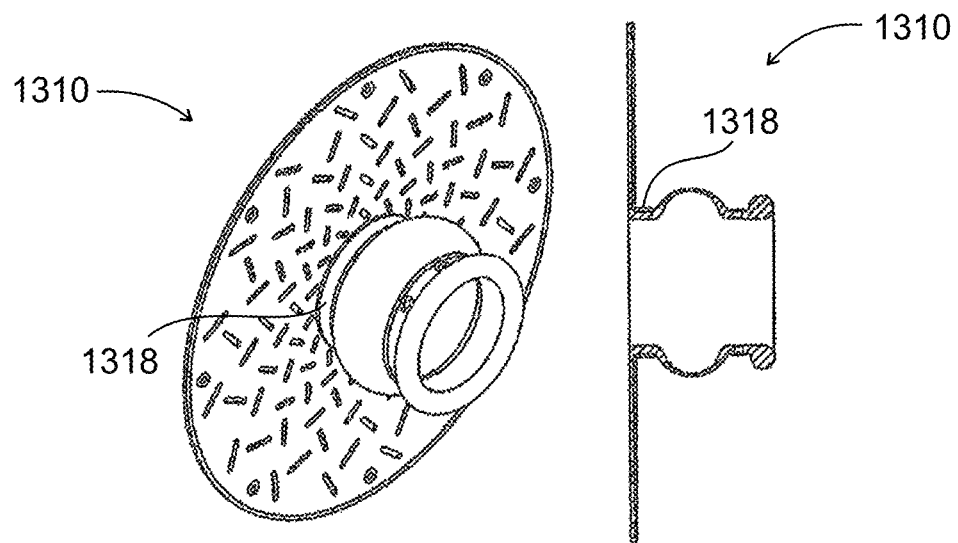

Reference is now made to FIG. 13B which schematically illustrates an exemplary sleeve 1310, according to some embodiments of the present invention. Optionally, sleeve 1310 includes a stiffened proximal neck 1318 adapted to substantially prevent the neck from widening. Widening of proximal neck 1318 may result in relative movement between a closure and sleeve 1310. Optionally, proximal neck 1318 includes a stiffener surrounding at least a portion of the perimeter of the neck. Optionally, proximal neck 1318 is hardened (the neck material is hardened). Sleeve 1310 may be similar to that shown in FIG. 2A at 100 with a variation that sleeve 1310 includes stiffened proximal neck 1318. Optionally, sleeve 1310 may be similar to other embodiment disclosed herein this disclosure with the mentioned variation(s).

Figure 13C:
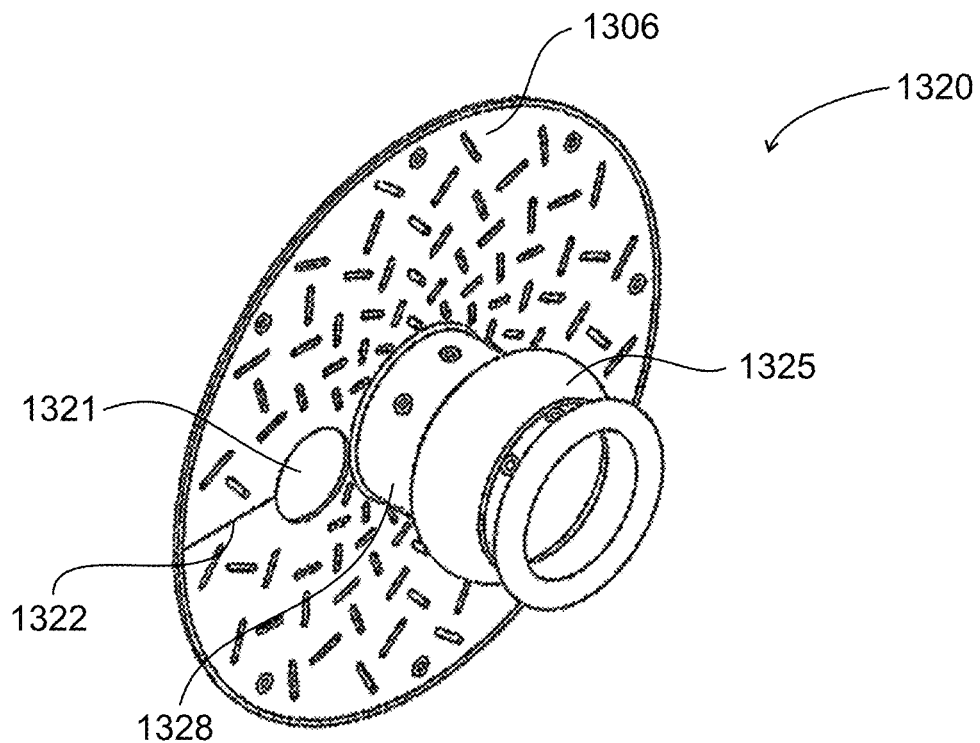

Reference is now made to FIG. 13C which schematically illustrates an exemplary sleeve 1320, according to some embodiments of the present invention. Optionally, sleeve 1320 is adapted to be used for "loop" or "double barrel" ostomy. Optionally, sleeve 1320 includes an opening 1321 through which a non-functional intestine is inserted, and a slot 1322 extending from an edge of a flange 1306 to the opening. Optionally, slot 1322 is adapted to allow flexing of flange 1306 for insertion of the non-functional intestine through opening 1321.

In some embodiments, sleeve 1320 includes a long proximal neck 1328. Optionally, long proximal neck 1328 is adapted to allow adequate space between the non-functional intestine and a sleeve cavity 1325.

Sleeve 1320 may be similar to that shown in FIG. 2A at 100, optionally to other embodiments disclosed herein this disclosure, with the mentioned variation(s).

Figure 13D:
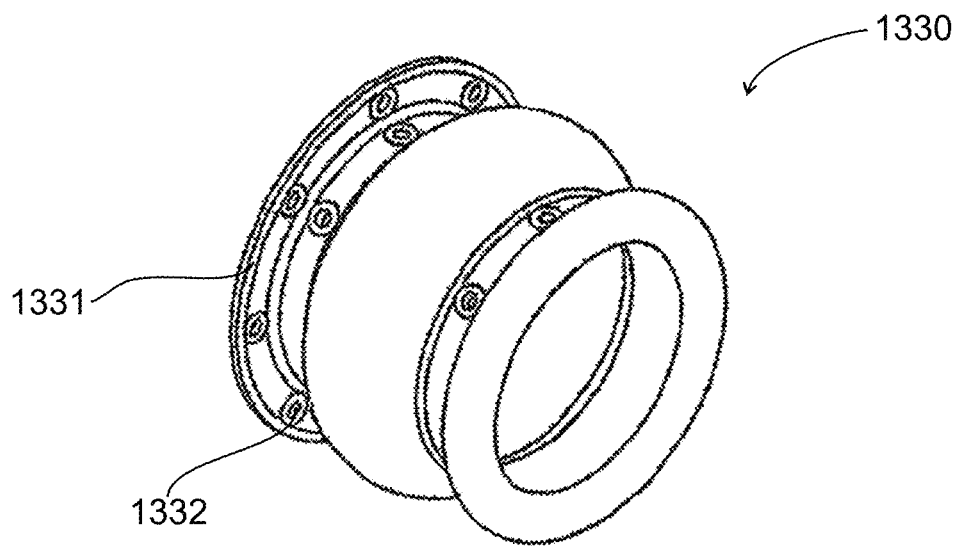

Reference is now made to FIG. 13D which schematically illustrates an exemplary sleeve 1330, according to some embodiments of the present invention. Optionally, sleeve 1330 is adapted to be used for temporary ostomies and includes a relatively narrow flange 1331 with openings 1332 for attaching the flange to a surface of the abdominal wall. Optionally, narrow flange 1331 is attached by introducing sutures through openings 1332, anchoring sleeve 1330 to the abdominal wall. Optionally, sleeve 1330 may be anchored through narrow flange 1331 using tacks, staples, or any other surgical means of attachment.

Sleeve 1330 may be similar to that shown in FIG. 2A at 100, optionally to other embodiments disclosed herein this disclosure, with the mentioned variation(s).

Figure 14A:
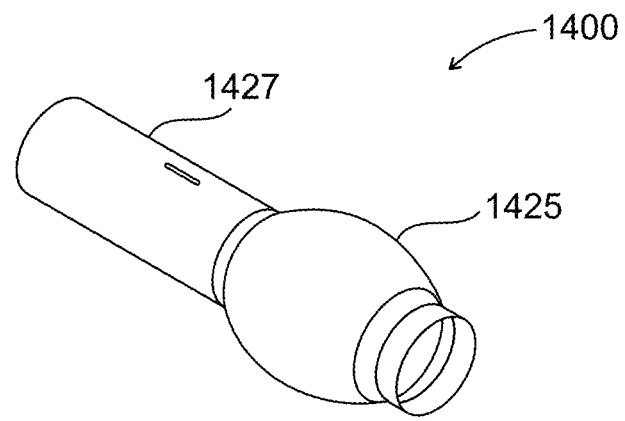
FIGS. 14A-14C schematically illustrate an exemplary closure; according to some embodiments of the present invention.
Figure 14B:
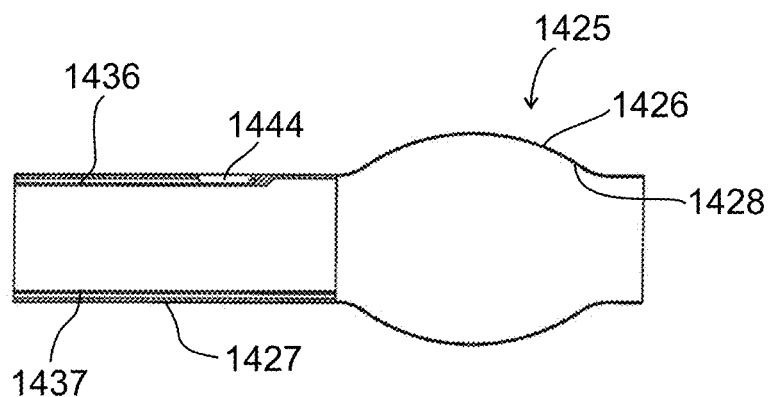
Figure 14C:
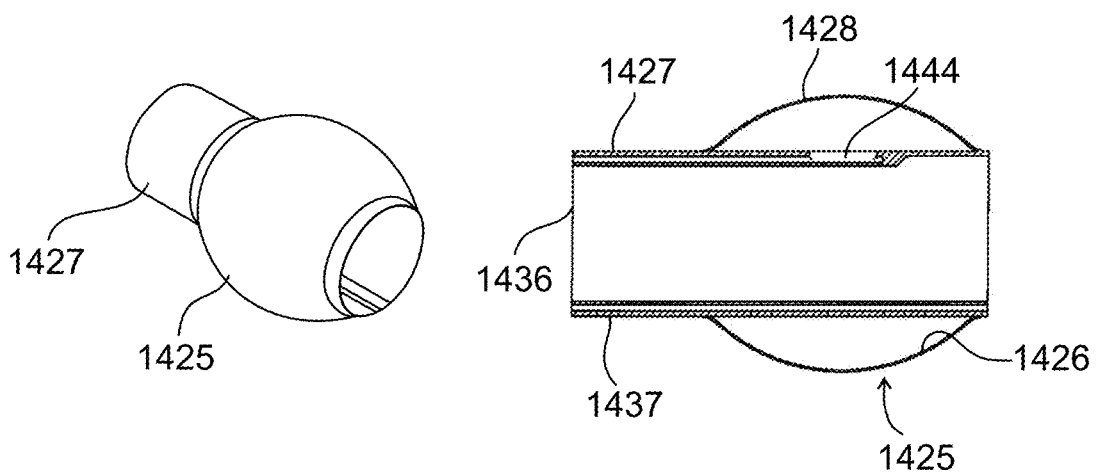

Reference is now made to FIGS. 14A-14C which schematically illustrate an exemplary closure 1400, according to some embodiments of the present invention. Optionally, closure 1400 includes a balloon 1425 located on a distal end of a stomal insert 1427. Optionally, balloon 1425 is integrally built as part of stomal closure 1427. Additionally or alternatively, balloon 1425 is adapted to be "flipped" over in a proximal direction so that an external surface 1426 of the balloon prior to flipping is an internal surface following the flipping, and an internal surface 1428 prior to flipping is an external surface following the flipping. FIGS. 14A and 14B show closure 1400 with balloon 1425 prior to flipping. FIG. 14C shows closure 1400 with balloon 1425 following flipping. Optionally, balloon 1425 flips over to cover a balloon inflation hole (opening) 1444 through which an expansion fluid flows out from inflation lumen 1436 into the "flipped" balloon. Closure 1400 additionally includes an irrigation lumen 1437 extending along a portion of a length of stomal insert 1427. Optionally, irrigation lumen 1437 is adapted to transport flatus from inside closure 1400 to outside the closure.

In some embodiments, closure 1400, including stomal insert 1427, balloon 1425, inflation opening 1444, inflation lumen 1436, and irrigation lumen 1437, may be similar to that shown in other embodiments disclosed herein this disclosure, with the variations mentioned.

Figure 15A:
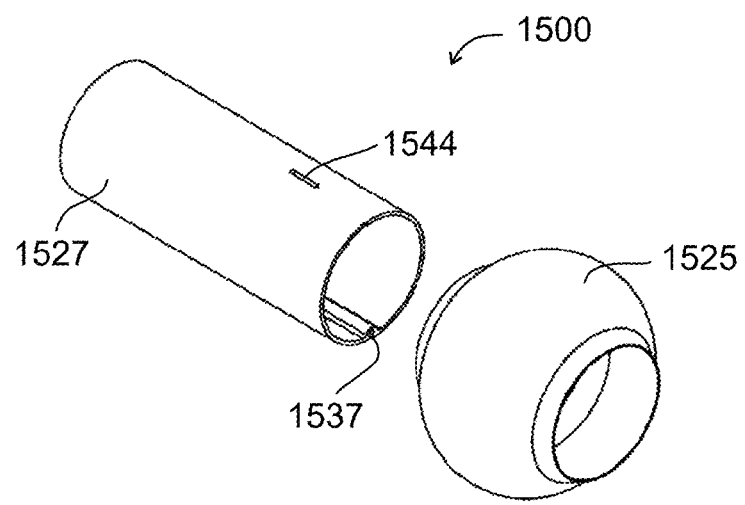
FIG. 15A-15B schematically illustrate an exemplary closure including a balloon resistant to collapse, according to some embodiments of the present invention.
Figure 15B:
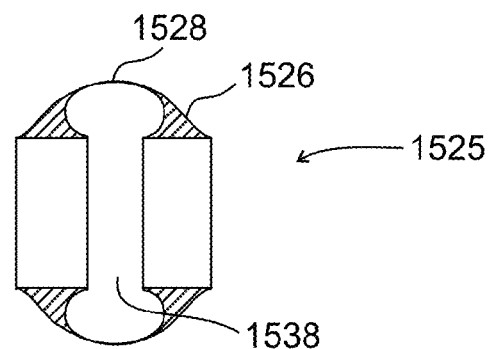

Reference is now made to FIG. 15A-15B which schematically illustrate an exemplary closure 1500 including a balloon 1525 resistant to collapse, according to some embodiments of the present invention. Optionally, balloon 1525 is attached to a distal end of a stomal insert 1527. Optionally, the balloon is located in another section of the stomal insert, for example a mid-section or a proximal section. Optionally, balloon 1525 includes a cross-sectional "U" profile including a relatively thick proximal portion 1529, a relatively thick distal portion 1530, and a relatively thin middle portion 1528. Optionally, proximal portion 1529 and distal portion 1530 support that portion of stomal insert 1527 which is located under balloon 1525 against collapse. Additionally or alternatively, a shape of proximal portion 1529 is configured to seat against a proximal portion of a sleeve cavity wall. Optionally, expansion fluid flows through an inflation lumen in stomal insert 1527, and through inflation opening 1544 into cavity 1538 in balloon 1525 for expanding the balloon. Closure 1500 additionally includes an irrigation lumen 1537 extending along a portion of a length of stomal insert 1527. Optionally, irrigation lumen 1537 is adapted to transport flatus from inside closure 1500 to outside the closure.

In some embodiments, closure 1500, including stomal insert 1527, balloon 1525, inflation opening 1544, inflation lumen 1536, and irrigation lumen 1537, may be similar to that shown in other embodiments disclosed herein this disclosure, with the variations mentioned.

Figure 15C:
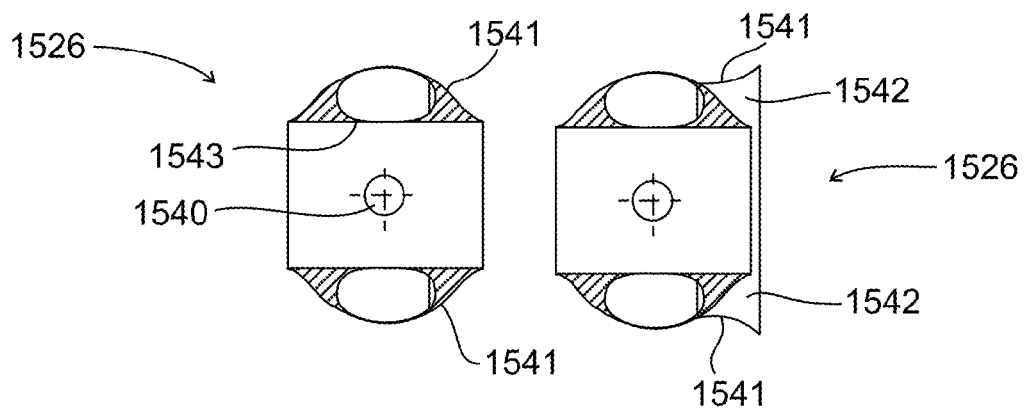
FIG. 15C schematically illustrates an exemplary non-collapsible balloon, according to some embodiments of the present invention.

Reference is now made to FIG. 15C which schematically illustrates an exemplary non-collapsible balloon 1526, according to some embodiments of the present invention. Optionally, balloon 1526 is adapted to be attached to a distal end of stomal insert 1527 shown in FIG. 15A. Optionally, balloon 1526 is similar to balloon 1525 shown in FIGS. 15A and 15B with a variation that balloon 1526 has a continuous bottom 1543. Optionally, expansion fluid flows through a hole 1540 for inflating balloon 1526 (instead of cavity 1538 in balloon 1525). Optionally, balloon 1526 includes an opening 1542 on a side 1541 (may be the proximal or distal side). Additionally or alternatively, opening 1541 is closed using attachment methods known in the art, for example by bonding, during assembly.

Figure 16A:
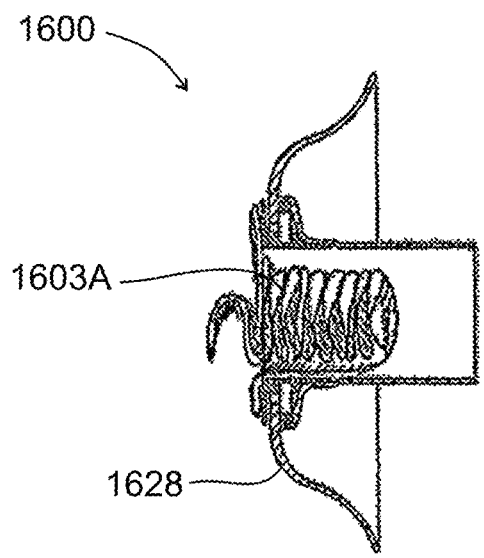
FIGS. 16A-16C schematically illustrate exemplary mechanisms for allowing a user to unfurl a waste content collection bag from within a closure, according to some embodiments of the present invention.
Figure 16B:
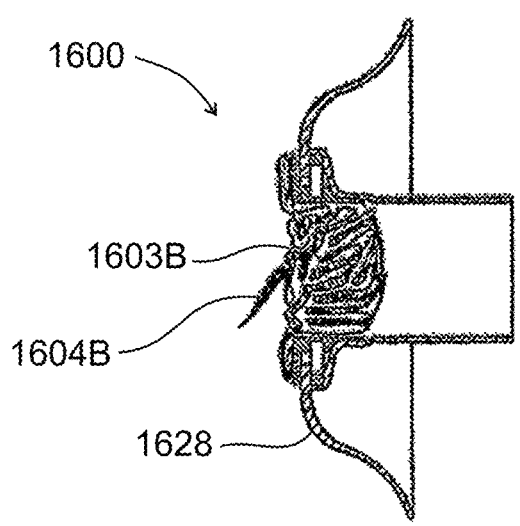
Figure 16C:
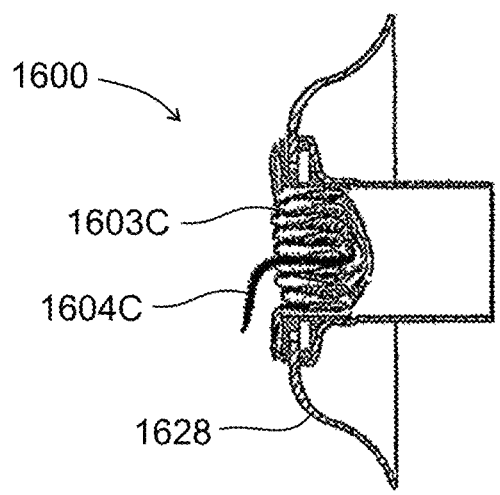

Reference is now made to FIGS. 16A-16C which schematically illustrate alternate exemplary mechanisms for allowing a user to unfurl a waste content collection bag from within a closure 1600, according to some embodiments of the present invention. In FIG. 16A, the user optionally unfurls a bag 1603A by pulling on a bag portion in stomal cover 1628. Optionally, the bag portion is arranged to protrude from stomal cover 1628 for easy access by the user. In FIG. 16B, the user optionally unfurls a bag 1603B by pulling on a strap or cord 1604B in stomal cover 1628 attached to a proximal end of the bag. Optionally, strap 1604B is arranged to protrude from stomal cover 1628 for easy access by the user. In FIG. 16C, the user optionally unfurls a bag 1603C by pulling on a strap or cord 1604C in stomal cover 1628 attached to a proximal end of the bag. Optionally, strap 1604C is arranged to protrude from stomal cover 1628 for easy access by the user. Optionally, closure 1600, stomal cover 1628, and bag 1603A-1603C, may be similar to those shown in other embodiments disclosed herein this disclosure, with the variations mentioned.

Reference is now made to FIGS. 17A-17F which schematically illustrate alternate methods for storing a waste content collection bag in a stomal cover 1728 included in a closure 1700, according to some embodiments of the present invention.

Figure 17A:
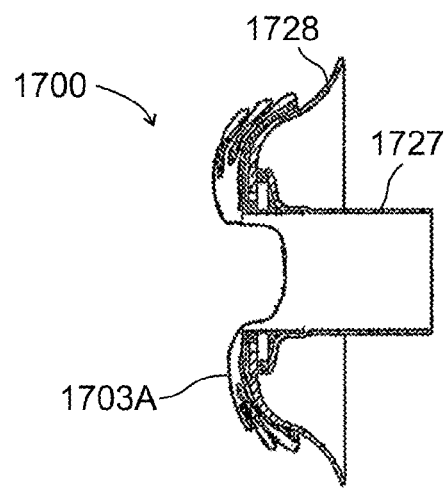
FIGS. 17A-17F schematically illustrate methods for storing a waste content collection bag in an exemplary stomal cover included in a closure, according to some embodiments of the present invention.

In FIG. 17A, optionally a bag 1703A is folded on top of stomal cover 1728 at a proximal end of stomal insert 1727. Optionally, bag 1703A is relatively densely packed onto stomal cover 1728. Optionally, bag 1703A is held in place by a cap (not shown) adapted to fit over stomal cover 1728.

Figure 17D:
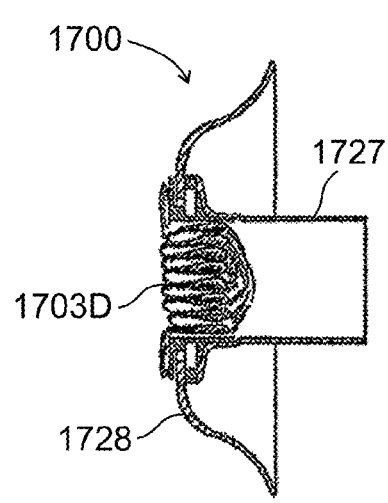
Figure 17B:
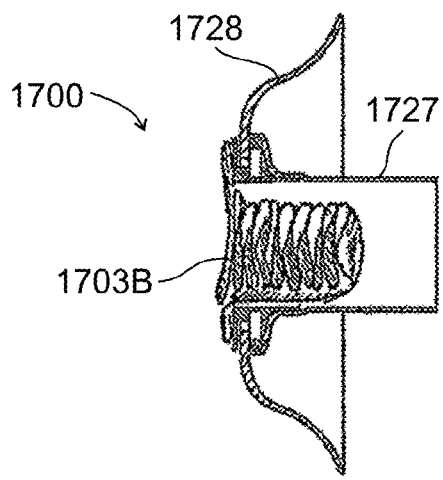

In FIG. 17B, optionally a bag 1703B is furled in a transversal direction inside stomal cover 1728 and the proximal end of stomal insert 1727.

Figure 17E:
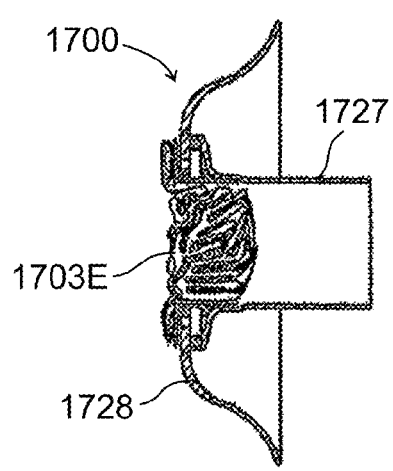
Figure 17C:
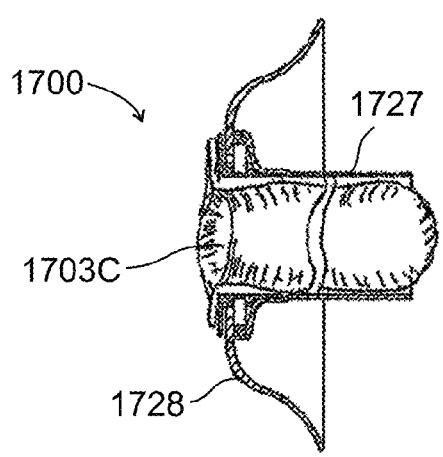

In FIG. 17C, optionally a bag 1703C is inserted to its full length inside stomal cover 1728 and stomal insert 1727.

In FIG. 17D, optionally a bag 1703D is furled in an axial direction inside stomal cover 1728 and the proximal end of stomal insert 1727.

In FIG. 17E, optionally a bag 1703E is furled in no particular order inside stomal cover 1728 and the proximal end of stomal insert 1727.

Figure 17F:
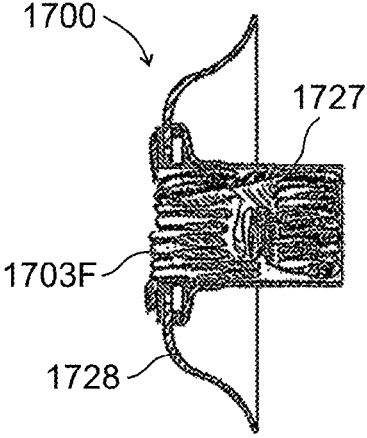

In FIG. 17F, optionally a bag 1703F is furled partially in a transversal direction and partially in an axial direction inside stomal cover 1728 and the proximal end of stomal insert 1727.

In some embodiments, closure 1700, stomal cover 1728, stomal insert 1727, and bag 1703A-1703F may be similar to those shown in other embodiments disclosed herein this disclosure, with the variations mentioned.

Figure 18A:
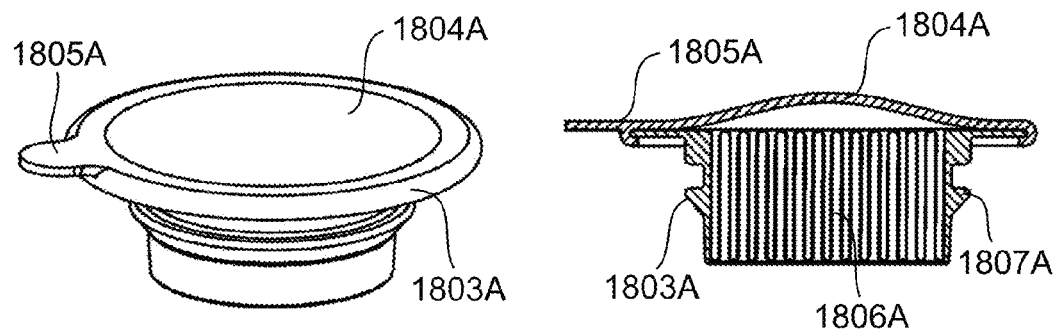
FIGS. 18A and 18B schematically illustrate exemplary caps, respectively, according to some embodiments of the present invention.
Figure 18B:
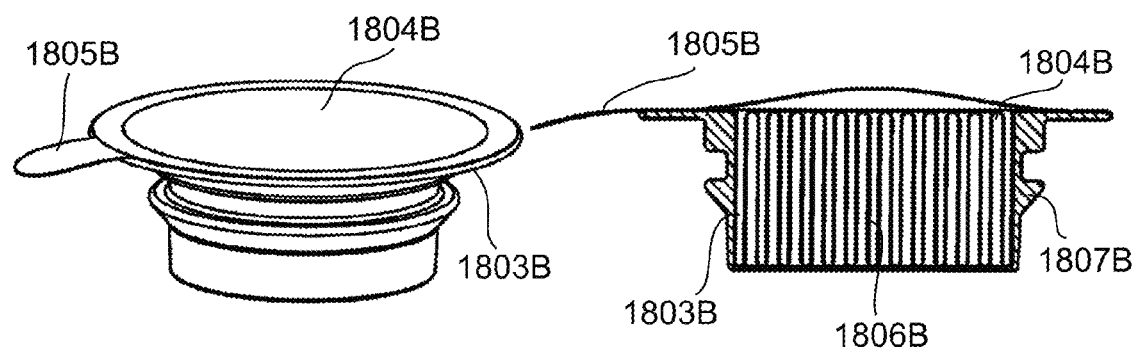

Reference is now made to FIGS. 18A and 18B which schematically illustrate exemplary bag assemblies 1803A and 1803B, respectively, according to some embodiments of the present invention. Optionally, bag assemblies 1803A and 1803B include a furled bag 1806A and 1806B, a bag housing 1807A and 1807B and a cover 1804A and 1804B, respectively. Optionally, bag assemblies 1803A and 1803B are adapted to fit onto a stomal cover (not shown). Optionally, bag assembly 1803A includes a cover 1804A made from a relatively hard material (for example, a hard plastic). Optionally, hard cover 1804A includes an extended rim 1805A for allowing easier removal of cover 1804A from bag assembly 1803A. Optionally, bag assembly 1803B includes a cover 1804B made from a relatively soft material (for example, a soft plastic or film). Optionally, soft cover 1804B includes an extended rim 1805B for allowing easier removal of cover 1804B from bag assembly 1803B. Optionally, bag assemblies 1803A and/or 1803B may be similar to those shown in other embodiments disclosed herein this disclosure, with the variations mentioned.

Reference is now made to FIGS. 19A-19E which schematically illustrate an exemplary mechanism for blocking flow of bowel waste content 1910 out of closure 1900 while a waste content collection bag 1903 is being replaced by a user, according to some embodiments of the present invention. Optionally, the blocking mechanism includes an internal balloon 1905 inside stomal insert 1927 connected through an inflation lumen 1906 to an external inflation port 1904 on an outside of closure 1900. Optionally, external valve is located on stomal cover 1928.

Figures 19A, 19B, 19C:
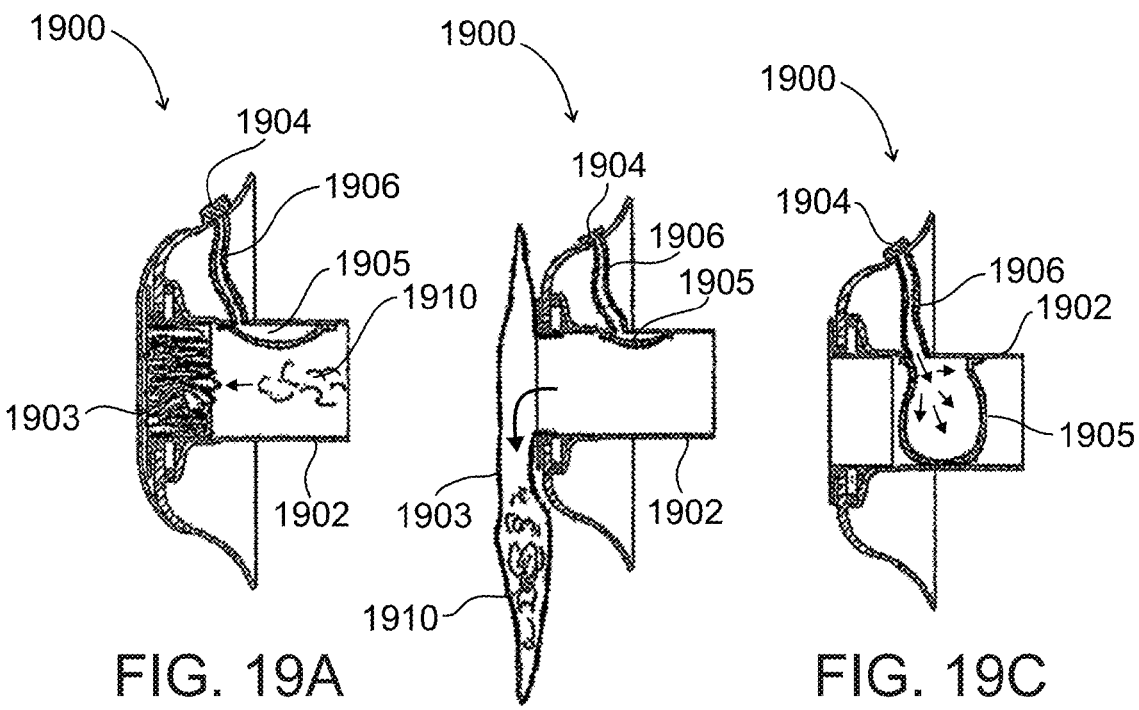
FIGS. 19A-19E schematically illustrate an exemplary mechanism for blocking flow of bowel waste content out of a closure while a waste content collection bag is being replaced by a user, according to some embodiments of the present invention.
Figures 19D, 19E:
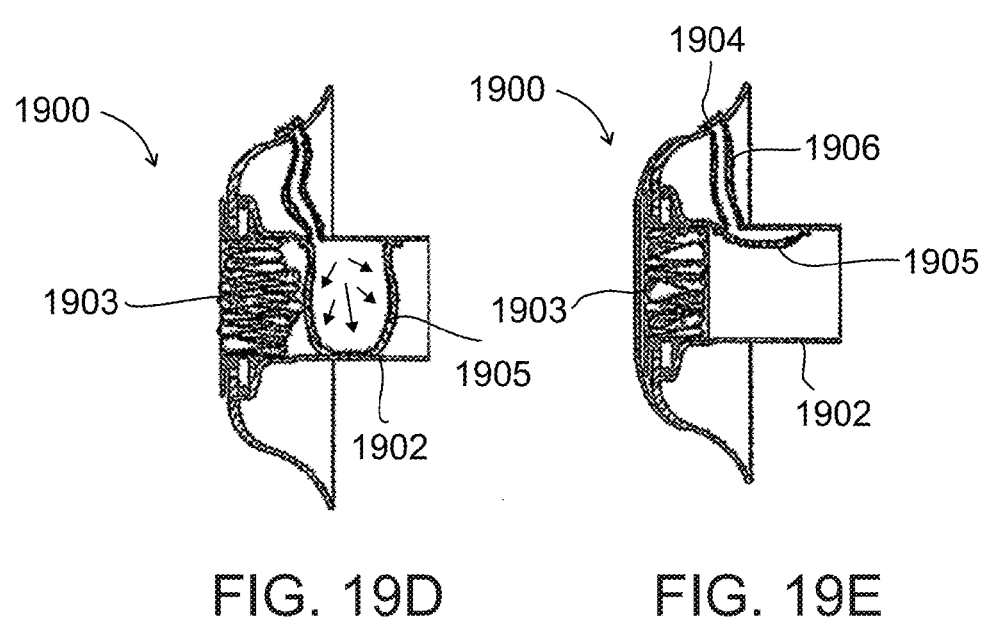

In FIG. 19A, optionally axial pressure from waste content 1910 in stomal insert 1927 pushes out bag 1903. Internal balloon 1905 is deflated so as to not interrupt passage of waste content 1910 through a proximal end of stomal insert 1927 into bag 1903. In FIG. 19B, optionally, bag 1903 is deployed by the axial pressure of waste content 1910 and the content falls into the bag. In FIG. 19C, optionally, following evacuation of waste content 1910, an expansion fluid is inserted through inflation port 1904 and lumen 1906 to inflate balloon 1905. Optionally, internal balloon 1905 is inflated to a size where the passage to the proximal end of stomal insert 1927 is blocked by the balloon. Used bag 1903 is removed. In FIG. 19D, optionally a new bag 1903 is attached to closure 1900. Optionally, bag 1903 is fitted into stomal cover 1928 and the proximal end of stomal insert 1927. In FIG. 19E, optionally, the expansion fluid is removed from balloon 1905 through lumen 1906 and inflation port 1904 for deflating the balloon. Optionally, the passage of waste content 1910 to the proximal end of stomal insert is possible once balloon 1925 is fully deflated. Optionally, passage to the proximal end is possible for balloon 1925 partially deflated. Optionally, closure 1900, stomal insert 1927, stomal cover 1928, and bag 1903 may be similar to those shown in other embodiments disclosed herein this disclosure, with the variations mentioned.

Reference is now made to FIGS. 19F-19G, 19H and 19I which schematically illustrate alternate exemplary mechanisms for blocking flow of bowel waste content out of closure 1930, 1940, and 1950, respectively, while a waste content collection bag is being replaced by a user, according to some embodiments of the present invention.

Figure 19F:
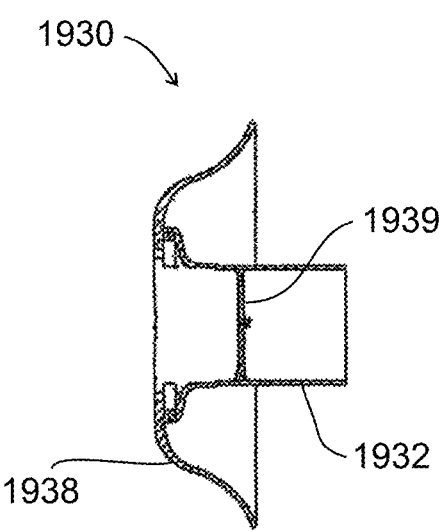
FIGS. 19F-19I schematically illustrate exemplary mechanisms for blocking flow of bowel waste content out of a closure while a waste content collection bag is being replaced by a user, according to some embodiments of the present invention.
Figure 19G:
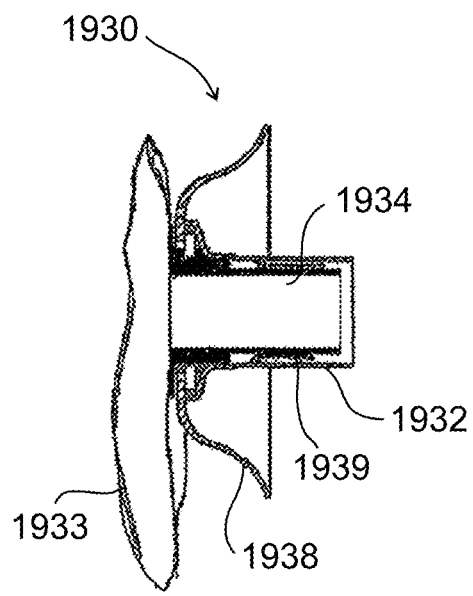

In FIGS. 19F-19G, optionally the blocking mechanism includes a one-way valve 1939 located inside of a stomal insert 1932 in closure 1930. Optionally, one-way valve 1939 is adapted to keep waste content from flowing through a proximal end of stomal insert 1932 and out stomal cover 1938. Optionally, one-way valve 1939 is adapted to be opened by a bag cannula 1934 included in a bag 1933, when the bag cannula is inserted through the stomal cover into the stomal insert and acts on the valve. Optionally, waste content flows through open one-way valve 1939 and bag cannula 1934 into bag 1933.

Figure 19H:
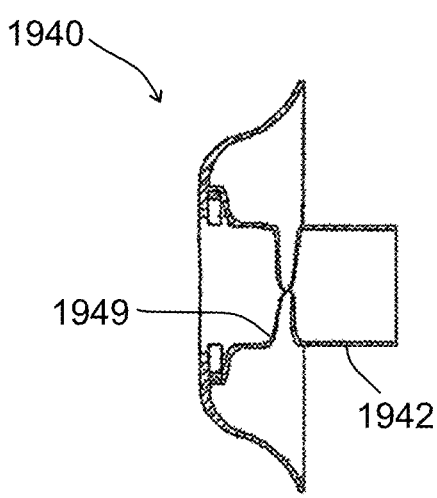

In FIG. 19H, optionally, a wall section 1949 in stomal insert 1942 is collapsible so that a passage of waste content out of closure 1940 is not possible unless the wall section is supported. Optionally, bag cannula 1934 included in bag 1933 and shown in FIG. 19G, is adapted to support wall section 1949 when inserted through stomal cover 1948 into stomal insert 1942. Optionally, waste content flows through bag cannula 1934 into bag 1933.

Figure 19I:
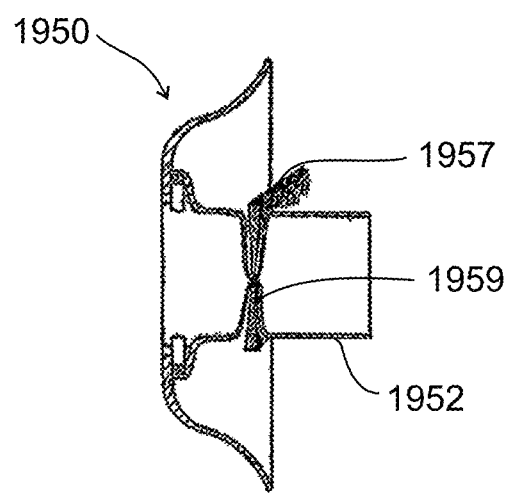

In FIG. 19I, optionally, a wall section 1959 in stomal insert 1952 is clamped together by a clamp 1957, closing the passage of waste content out of closure 1950. Optionally, bag cannula 1934 included in bag 1933 and shown in FIG. 19G, is adapted to open clamp 1957 when inserted through stomal cover 1958 into stomal insert 1952. Alternatively, the clamp is adapted to be manually opened by the user. Optionally, waste content flows through bag cannula 1934 into bag 1933.

In some embodiments, closure 1930-1950, stomal insert 1932-1952, stomal cover 1938-1958, and bag 1933 may be similar to those shown in other embodiments disclosed herein this disclosure, with the variations mentioned.

Reference is now made to FIGS. 20A-20C which schematically illustrate alternate methods of closing an exemplary waste content collection bag when removed from a closure following evacuation, according to some embodiments of the present invention.

In FIG. 20A, optionally a waste collection bag 2003A includes a strand 2004A which is wrapped around a portion of the bag below an opening 2005A to the bag, closing (clamping) the bag. In FIG. 20B, optionally, a waste collection bag 2003B includes an opening 2005B adapted to receive a cap 2004B. In FIG. 20C, optionally a waste collection bag 2003C is clamped on a portion of the bag below an opening 2005C to the bag using a clasp 2004C. Optionally, bag 2003A-2003C and bag opening 2005A-2005C may be similar to those shown in other embodiments disclosed herein this disclosure, with the variations mentioned.

Figure 21A:
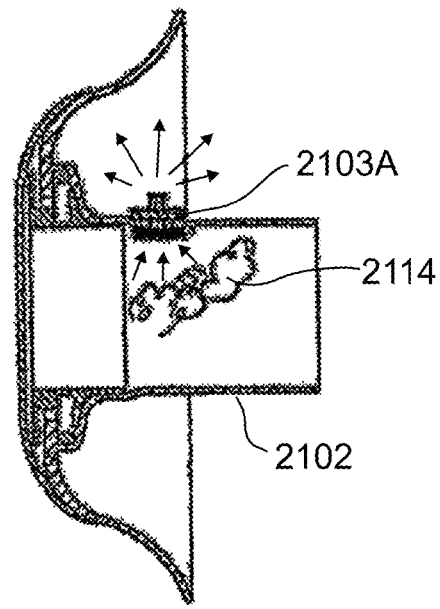
FIGS. 21A-21C schematically illustrate exemplary mechanisms for flatus release, according to some embodiments of the present invention.
Figure 21B:
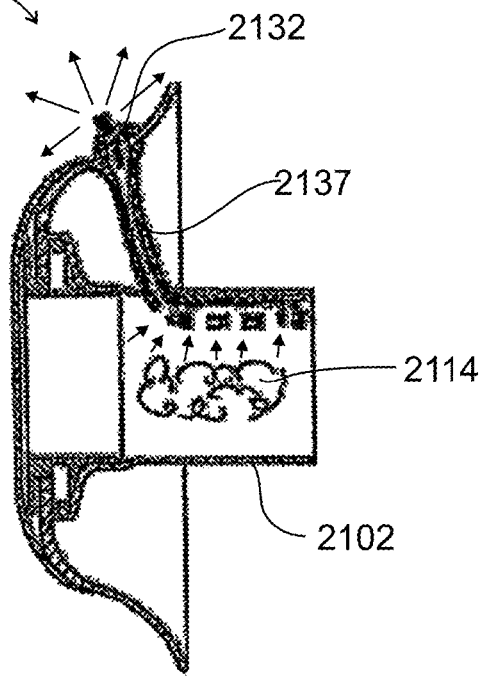
Figure 21C:
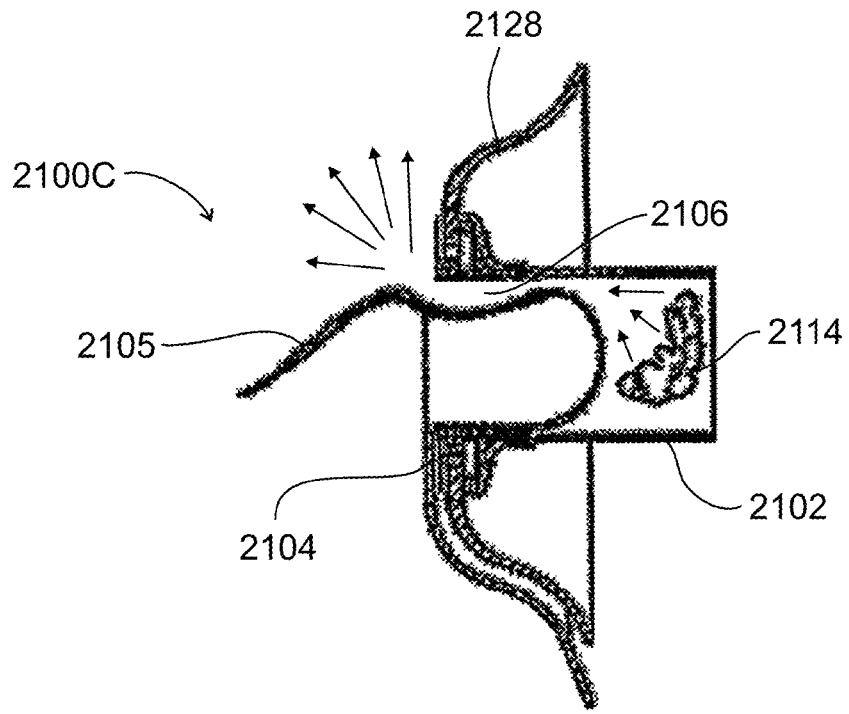

Reference is now made to FIGS. 21A-21C which schematically illustrate alternate exemplary mechanisms for flatus release, according to some embodiments of the present invention.

In FIG. 21A, the flatus release mechanism in closure 2100A optionally includes a flatus release valve 2103A directly connected to an interior of stomal insert 2102A. Optionally, flatus release valve 2103A is controlled by the user. Optionally, the user presses a button on valve 2103A to release flatus 2114 in stomal insert 2102A.

In FIG. 21B, the flatus release mechanism in closure 2100B optionally includes a flatus release valve 2132 connected to a lumen 2137 in stomal insert 2102B. Optionally, lumen 2137 is an irrigation lumen adapted to transport an irrigation fluid from flatus release valve 2132 through stomal insert 2102B for bowel irrigation. Optionally, irrigation lumen is adapted to transport flatus 2114 in stomal insert 2102B to flatus release valve 2132. Optionally, flatus release valve 2132 is adapted to release flatus 2114 from closure 2100B and to receive the irrigation fluid and direct it into irrigation lumen 2137.

In FIG. 21C, the flatus release mechanism in closure 2100C optionally includes a cap 2104 with a cover 2105 adapted to be opened by the user so that an opening 2106 is created at a proximal end of stomal insert 2102C and stomal cover 2128, allowing flatus 2114 to escape through the opening. Optionally, cap 2104 is adapted to be opened by a user in a way such that opening 2106 is sufficiently large to enable flatus passage and sufficiently small to block the passage of liquid and/or solid body waste. Optionally, cap 2104 includes a re-attachable cover 2105 or seal.

In some embodiments, closure 2100A-2100C including stomal insert 2102A-2102C, flatus release valve 2103A and 2132, lumen 2137, cap 2104, and cover 2105, may be similar to that shown in other embodiments disclosed herein this disclosure, with the variations mentioned.

Reference is now made to FIGS. 22A-22E which schematically illustrate alternate exemplary mechanisms for notifying a user of a need to evacuate, according to some embodiments of the present invention.

In FIG. 22A, the notification mechanism in a closure 2200A optionally includes a cap 2204A attached to a stomal cover 2228A with a concave flexible portion 2205A which protrudes through the stomal cover into a proximal end of a stomal insert 2202A. Optionally, flexible portion 2205A in cap 2204A is adapted to protrude (bulge) outwards from stomal cover 2228A, pushed by an axial pressure from waste content 2214 in stomal insert 2202A. Optionally, the user notices bulging flexible portion 2205A.

In FIG. 22B, the notification mechanism in a closure 2200B optionally includes a cap 2204B attached to a stomal cover 2228B including a flexible portion 2205B. Flexible portion 2205B is adapted to protrude (bulge) outwards from cap 2204B when pushed by an axial pressure from waste content 2214 in stomal insert 2202B. Optionally, the user notices bulging flexible portion 2205B.

In FIG. 22C, the notification mechanism in a closure 2200C optionally includes a cap 2204C attached to a stomal cover 2228C including a telescopic portion 2205C. Telescopic portion 2205C is adapted to protrude outwards from cap 2204C when pushed by an axial pressure from waste content 2214 in stomal insert 2202C. Optionally, the user notices protruding telescopic portion 2205C.

In FIG. 22D, the notification mechanism in a closure 2200D optionally includes an inner balloon 2207F inside a stomal insert 2202D interconnected through a lumen 2207E to an external balloon 2207D located externally to the closure. Optionally, external balloon 2207D is located on stomal cover 2228D. In an optional mode of operation, external balloon 2207D is deflated while internal balloon 2207F is inflated. Optionally, pressure from waste content 2214 acts on internal balloon 2207F forcing expansion fluid in the internal balloon to flow through lumen 2207E into external balloon 2207D. Additionally, external balloon 2207D inflates from the expansion fluid flowing into the balloon through lumen 2207E from internal balloon 2207F. Optionally, internal balloon 2207F partially, or wholly, deflates. Optionally, the user notices bulging of inflated external balloon 2207D.

In FIG. 22E, the notification mechanism in a closure 2200E optionally includes a cap 2204E attached to stomal cover 2228E, the cap including a pressure sensor 2205E for detecting a pressure from waste content 2214 inside stomal insert 2202E. Optionally, pressure sensor 2205E is located on a distal end of cap 2204E. Optionally, pressure sensor 2205E is located inside stomal insert 2202E. Additionally or alternatively, pressure sensor 2205E is connected to an alarm 2210 for notifying the user of a need to evacuate when waste content pressure is sensed. Optionally, alarm 2210 is audio, visual, or tactile (for example vibratory), or any combination thereof. Optionally, alarm 2210 is located on cap 2204E. Alternatively, alarm 2210 is located elsewhere on closure 2200E. Optionally, alarm 2210 and/or pressure sensor 2205E are electrically operated.

In some embodiments, closure 2200A-2200E including stomal insert 2102A-2102E, stomal cover 2228A-2228E, 2137, and cap 2204A-2204E, may be similar to that shown in other embodiments disclosed herein this disclosure, with the variations mentioned.

Reference is now made to FIGS. 23A-23E which schematically illustrate alternate exemplary safety mechanisms for controlling a maximum colonic pressure buildup in a closure, according to some embodiments of the present invention.

Figure 23A:
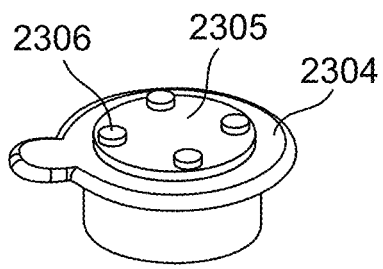
FIGS. 23A-23E schematically illustrate exemplary safety mechanisms for controlling a maximum colonic pressure buildup in a closure, according to some embodiments of the present invention.
Figure 23B:
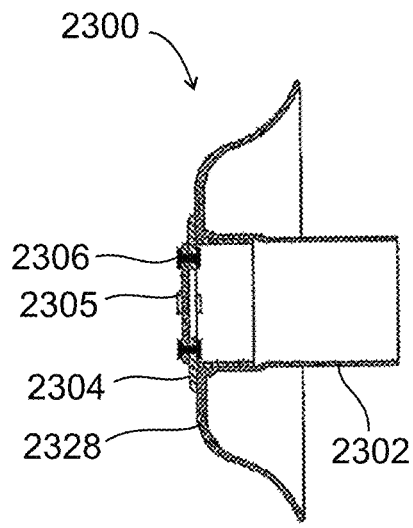
Figure 23C:
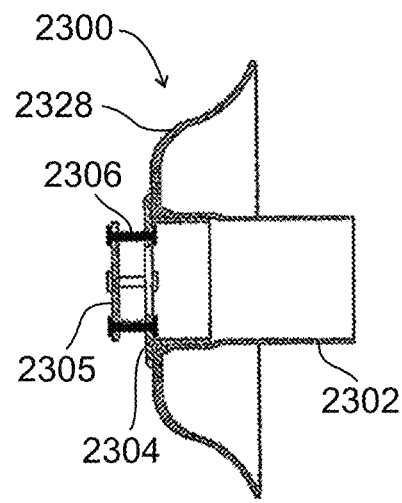

In FIGS. 23A-23C, the safety mechanism in closure 2300 optionally includes a cap 2304 with an opening 2307, the opening covered by a cover 2305 which is released when the colonic pressure reaches (or exceeds) a predetermined value over a predetermined period (length) of time. Cap 2304 is attached to stomal cover 2328 at a proximal end of stomal insert 2302. Optionally, cover 2305 is sealingly affixed to cap 2304 by affixing members 2306, the affixing members adapted to release the cover upon the maximum colonic pressure buildup over a predetermined period of time. Waste content may then flow out from stomal insert 2302 through opening 2307.

Figure 23D:
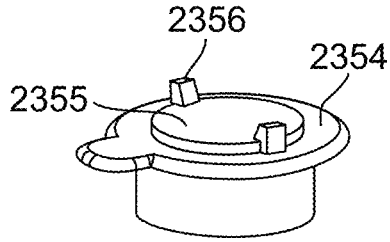
Figure 23E:
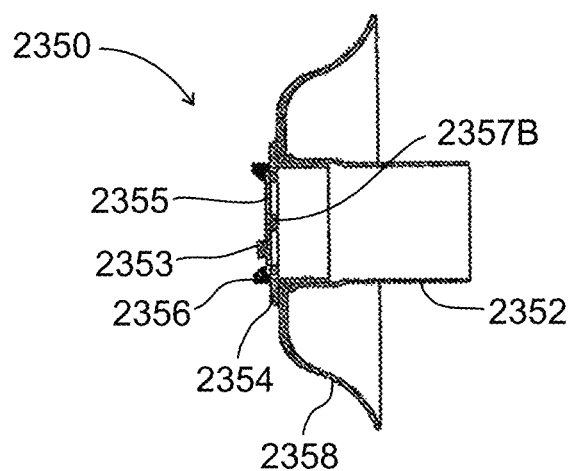

In FIGS. 23D-23E, the safety mechanism in closure 2350 optionally includes a cap 2354 with an opening 2357, the opening covered by a cover 2355 which is released when the colonic pressure reaches (or exceeds) a predetermined value over a predetermined period (length) of time. Cap 2354 is attached to stomal cover 2358 at a proximal end of stomal insert 2352. Optionally, cover 2355 is sealingly affixed to cap 2354 by affixing members 2356. Affixing members 2356 are electrically actuated and are adapted to release cover 2355 responsive to an activation signal received from a processor 2353. Processor 2355 activates affixing members 2356 responsive to measurements received from a pressure sensor 2357 in stomal insert 2353, when the pressure reaches the maximum colonic pressure buildup over a predetermined period of time. Waste content may then flow out from stomal insert 2352 through opening 2357.

In some embodiments, closure 2300 and 2350 including stomal insert 2302 and 2352, stomal cover 2328A and 2358, and cap 2304 and 2354, may be similar to that shown in other embodiments disclosed herein this disclosure, with the variations mentioned.

Figures 24A, 24B:
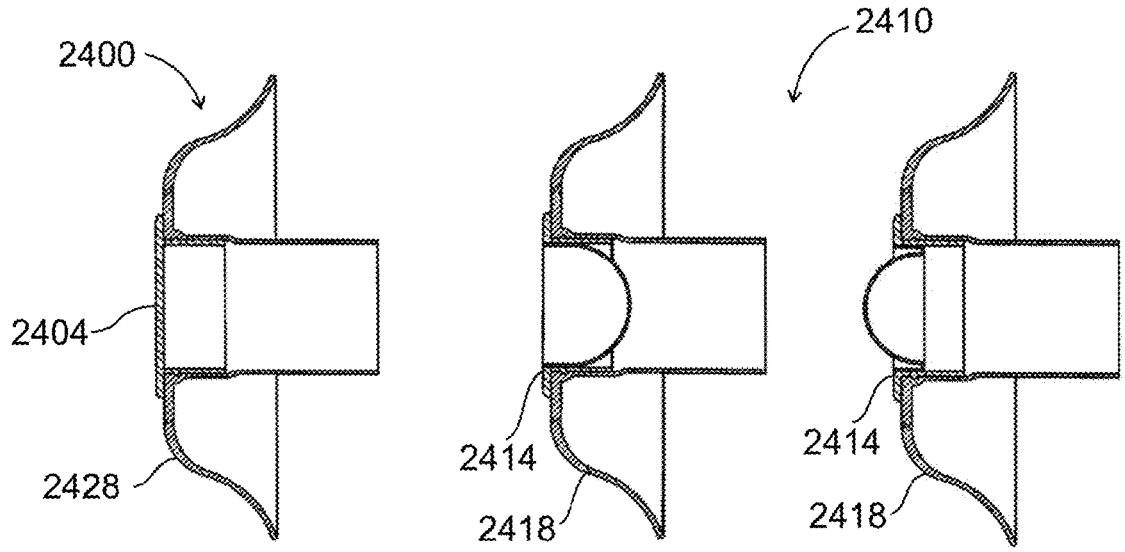
FIGS. 24A-24C schematically illustrate exemplary methods of using a closure with other devices, according to some embodiments of the present invention.
Figure 24C:
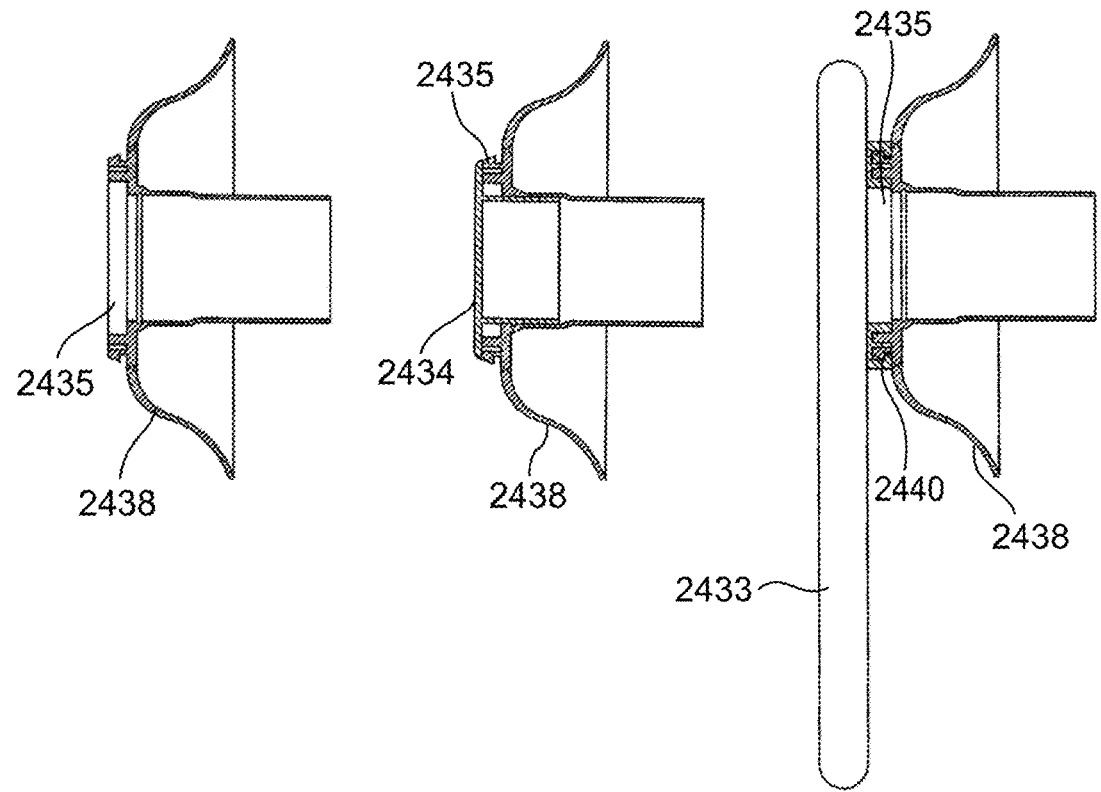

Reference is now made to FIGS. 24A-24C which schematically illustrate alternate exemplary methods of using a closure with other devices, according to some embodiments of the present invention.

In FIG. 24A, a closure 2400 is shown optionally being used without a collection bag, a cap 2404 attached to a stomal cover 2428 for sealing the closure. Optionally, cap 2404 is sealingly attached to stomal cover 2428 through a bulge in cap 2404 that fits into a recess in stomal cover 2428, or through any other method known in the art to sealingly attach two members.

In FIG. 24B, a closure 2410 is shown optionally being used without a collection bag. Optionally, closure 2400 is sealed by a cap 2414 attached to a stomal cover 2418, the cap adapted to provide a user with an indication of a need to evacuate. Optionally, cap 2414 includes a portion which is flexible and concave shaped. Optionally, cap 2414 is sealingly attached to stomal cover 2418 through a bulge in cap 2414 that fits into a recess in stomal cover 2418, or through any other method known in the art to sealingly attach two members.

In FIG. 24C, a closure 2420 includes a connector 2435 optionally attached to a stomal cover 2438, the connector suitable for attaching waste content collection bags known in the art. Optionally, a cap 2434 is attached to connector 2435 for sealing closure 2420. When evacuation is required, a user removes cap 2434 and attaches a waste content collection bag 2433 to connector 2435.

In some embodiments, closure 2400-2430 including stomal cover 2428-2438, and cap 2404-2434, may be similar to that shown in other embodiments disclosed herein this disclosure, with the variations mentioned.

Figure 25:
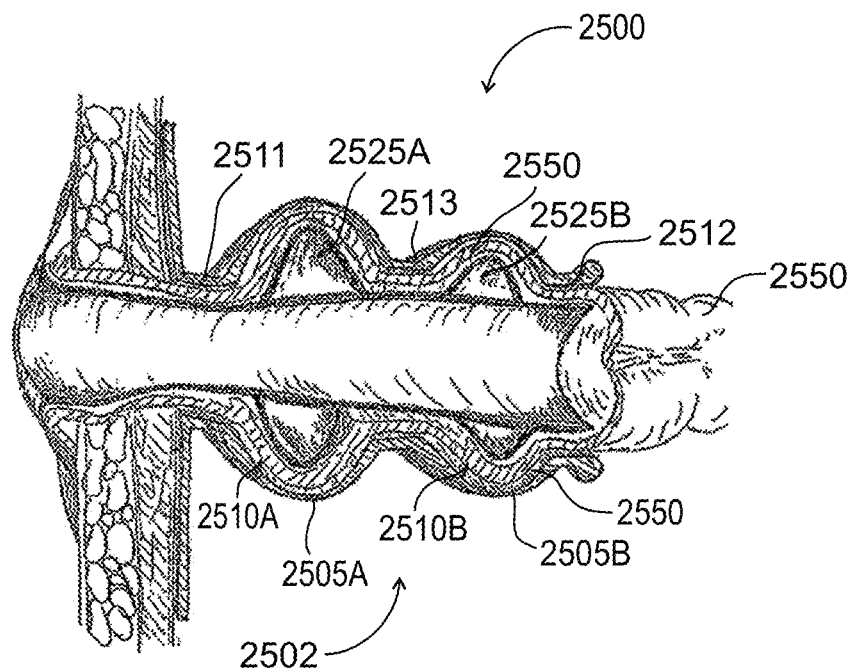
FIG. 25 schematically illustrates an exemplary Ostomy containment device including multiple fixation elements and multiple sleeve cavities, according to some embodiments of the present invention.

Reference is now made to FIG. 25 which schematically illustrates an exemplary Ostomy containment device 2500 including multiple fixation elements and multiple sleeve cavities, according to some embodiments of the present invention. Optionally, device 2500 includes a closure 2502 with a proximal fixation element 2525A and a distal fixation element 2525B. Optionally, sleeve 2501 includes a proximal sleeve cavity 2505A for accommodating proximal fixation element 2525A, and a distal sleeve cavity 2505B for accommodating distal fixation element 2525B. Additionally or alternatively, closure 2502 is inserted in intestine 2550 such that the intestinal tissue passes between the closure and sleeve 2501 through a stoma 2570 and is attached to a skin 2571 of the abdominal wall.

In some embodiments, a substantially hermetic sealing is created between intestine 2550 and closure 2502 along a proximal section 2511, an intermediate section 2513, and a distal section 2512 of the closure. Additionally or alternatively, hermetic sealing is created along the contact surface between proximal fixation element 2525A and portion of intestine 2550 within proximal sleeve cavity 2505A, and/or along the contact surface between distal fixation element 2525B and portion of intestine 2550 within distal sleeve cavity 2505B. Optionally, a force exerted on closure 2502 by waste content is counteracted by a proximal portion 2510A in proximal cavity 2525A, and by a proximal portion 2510B in distal cavity 2525B. Additionally or alternatively, the force is distributed over a larger area, reducing mechanical stress on intestine 2550.

In some embodiments, balloon 2525A and balloon 2525B are alternately inflated and deflated. Optionally, alternating between inflating a first balloon while deflating a second balloon results in pressure reduction in the intestinal section in the area of the deflated balloon. Optionally, the pressure reduction in the intestinal section provides for a recovery time in the section from potential pressure injury such as, for example, ischemia, necrosis, among others. Optionally, anchoring of the closure to the sleeve is performed by the inflated balloon.

In some embodiments, device 2500, including sleeve 2501 and closure 2502 may be similar to that shown in other embodiments disclosed herein this disclosure, with the variations mentioned.

Figure 26:
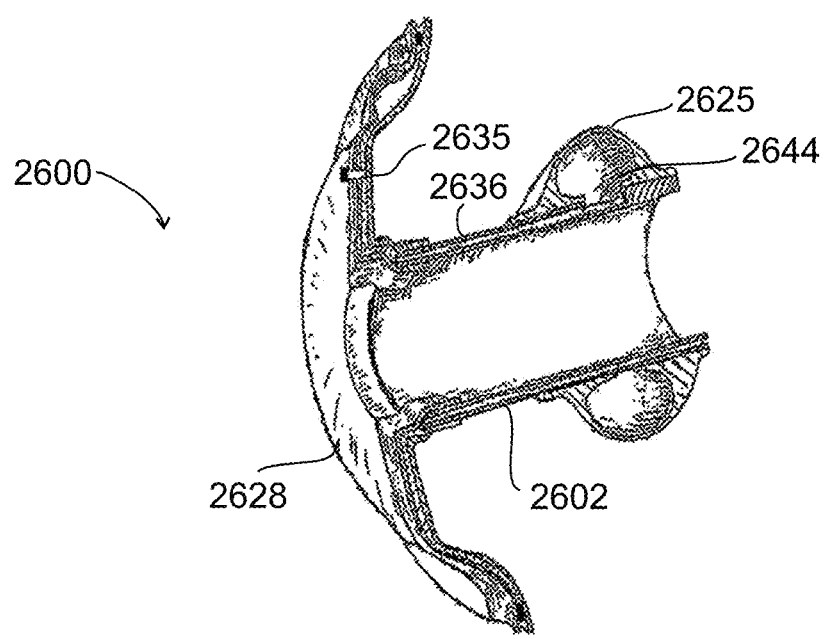
FIG. 26 schematically illustrates an exemplary mechanism for substantially preventing balloon over-inflation in an exemplary closure, according to some embodiments of the present invention.

Reference is now made to FIG. 26 which schematically illustrates an exemplary mechanism for substantially preventing balloon 2625 over-inflation in an exemplary closure 2600, according to some embodiments of the present invention. Optionally, a relief valve 2635 is included in closure 2600 and connected to inflation lumen 2636. Optionally, an attempt to introduce excessive expansion fluid through lumen 2636 and inflation hole 2644 in stomal insert 2602, and into balloon 2625 will result in a pressure buildup in the lumen causing relief valve 2635 to open. The excessive expansion fluid may then flow out relief valve 2635, preventing over-inflation of balloon 2625. Optionally, relief valve 2635 is located on stomal cover 2628 or elsewhere on closure 2600 outside a user's body. Optionally, relief valve 2635 is located on stomal insert 2602. Optionally, closure 2600 including stomal cover 2628, stomal insert 2602, inflation lumen 2636, and balloon 2625, may be similar to that shown in other embodiments disclosed herein this disclosure, with the variations mentioned.

Figure 27:
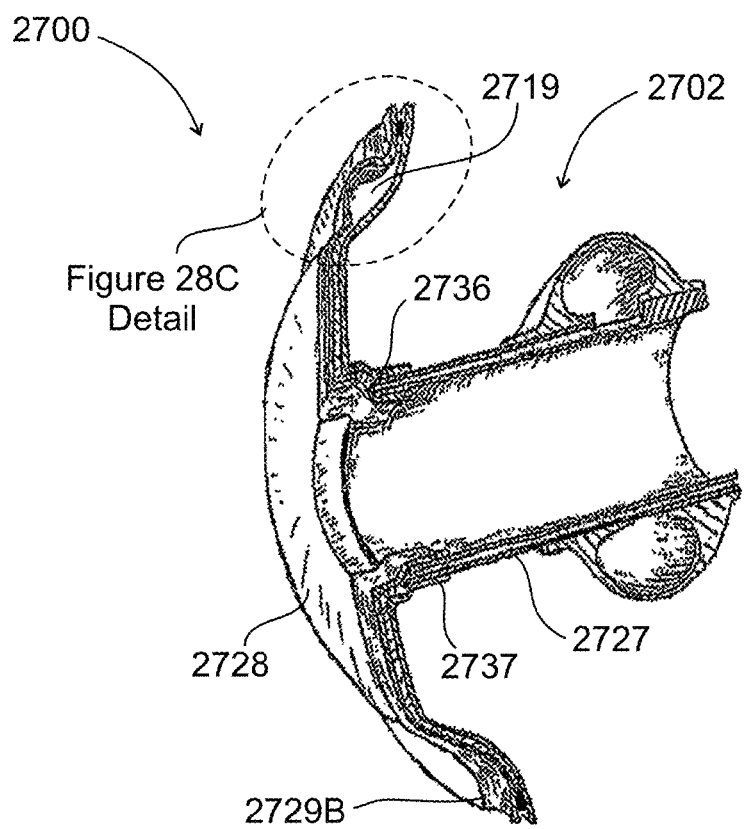
FIG. 27 schematically illustrates a sectional view of an exemplary closure, according to some embodiments of the present invention.
Figure 28:
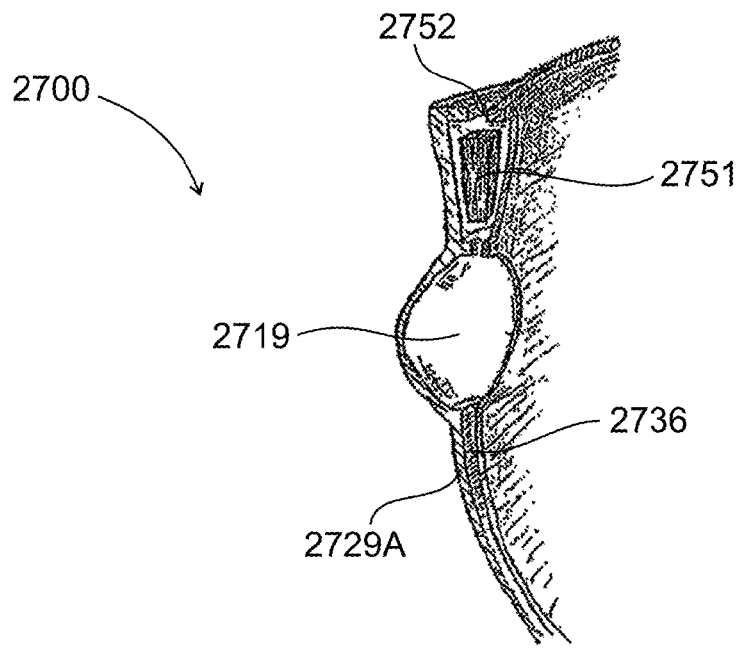
FIG. 28 schematically illustrates a detailed view of a section of the closure of FIG. 27, according to some embodiments of the present invention.

Reference is now made to FIG. 27 which schematically illustrates a sectional view of an exemplary closure 2700, and to FIG. 28 which schematically illustrates a detailed view of a section of the closure, according to some embodiments of the present invention.

In some embodiments, stomal cover 2728 and stomal insert 2727 are fabricated separately, and attached during assembly. Optionally, stomal insert 2727 includes a constant cross-sectional shape. Optionally, stomal insert 2727 is fabricated using extrusion. Additionally or alternatively, stomal cover 2728 is attached (via bonding, welding etc.) to an outer surface of stomal insert 2727. Optionally, a capping film 2729A is attached to stomal cover 2728 and to a proximal end of an inflation lumen 2736 leaving a space between them to form a lumen 2736A for inflation fluid to flow in. Optionally, a second capping film 2729B is attached at an alternative location on stomal cover 2728, forming a lumen 2737A for the irrigation fluid to flow through into an irrigation lumen 2737 in stomal insert 2727. Optionally, a cavity (bulge) 2719 is formed between capping film 2729A and stomal cover 2728. Optionally, cavity 2719 is adapted to serve as a control balloon which expands upon an over-pressure buildup in inflation lumen 2736 and/or 2736A. Additionally or alternatively, a one-way valve 2751 is included, the valve adapted to allow balloon 2725 to retain its inflation pressure despite opening the proximal end of inflation lumen 2736. Optionally, a one-way valve is included in irrigation lumen 2737A.

Reference is now made to FIGS. 29A-29G which schematically illustrate exemplary methods of inserting a closure into a sleeve and an intestinal portion, including tools optionally used for carrying out the methods, according to some embodiments of the present invention. Optionally, the insertion is performed by a user of the introducer which may be, for example a physician. Optionally, the user may be the user of the containment device.

Figure 29A:
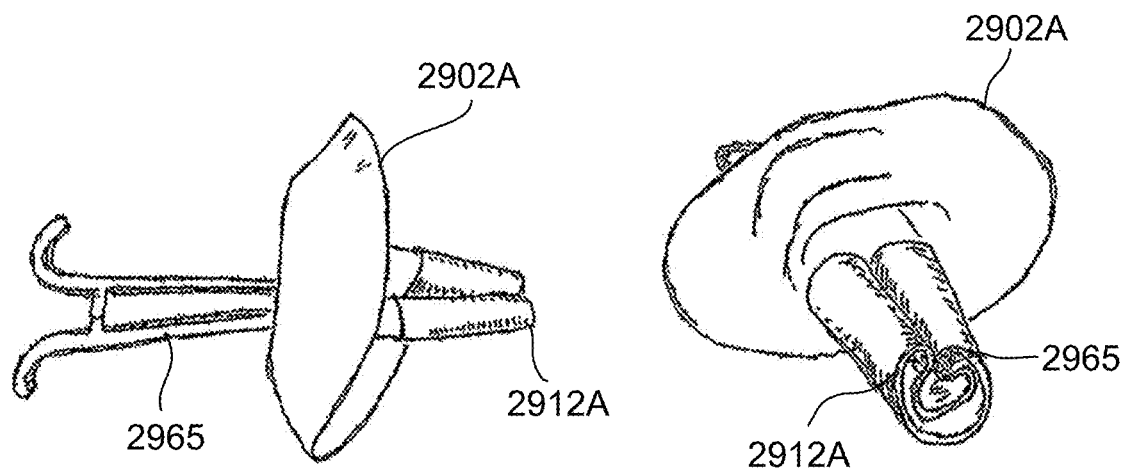

In FIG. 29A, a tweezers 2965 is optionally inserted through a stomal cover and moved along a closure 2902A until the tweezers reach a distal end 2912A of the closure. Optionally, distal end 2912A is folded and held in place by tweezers 2965. Optionally, a cross-section of distal end 2912A is smaller, allowing for easier insertion of closure 2902A. Optionally, once closure 2902A is in place inside the sleeve, tweezers 2965 may be removed. Optionally, any other means known in the art for clamping, as for example any kind of clamp or clasp, may be used instead of tweezers 2965 for holding distal end 2912A in folded state.

Figure 29B:
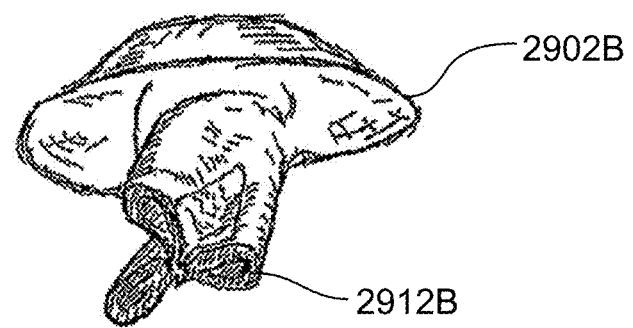

In FIG. 29B, an introducer 2975 shown in FIG. 29C is adapted to manipulate closure 2902B for temporarily folding a distal end 2912B and reducing its cross-section. Once temporarily reduced, introducer 2975 together with closure 2902B may be inserted, the introducer removed once the closure is in place inside the sleeve. Optionally, a lubricant, for example a gel, is applied to the exterior of the closure for reducing friction during insertion.

In some embodiments, introducer 2975 includes a main rod 2977 with three legs 2978 including three extensions 2979 at a distal end, and a sleeve 2976. Main rod 2977 is adapted to slide inside sleeve 2976, legs 2978 adapted to close towards one another as the main rod slides in a proximal direction relative to the sleeve. Extensions 2979 are adapted to be attached (inserted) to fixation points 47 in support 26 shown in FIG. 6C, folding the support as legs 2978 approach one another.

Figure 29D:
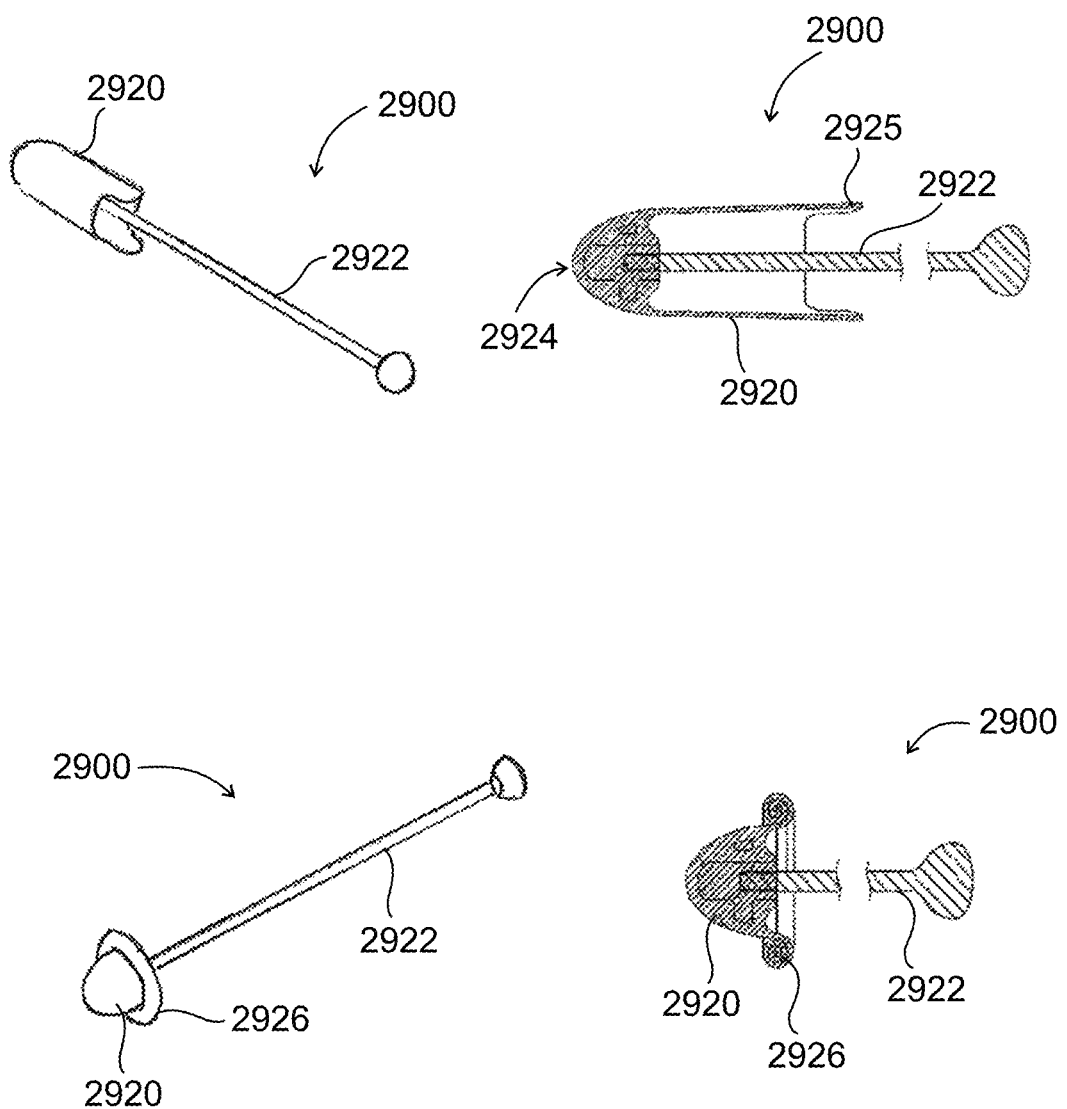

In FIG. 29D, an introducer 2900 is adapted to manipulate closure 2902C for temporarily folding a distal end 2912C and reducing its cross-section. Once temporarily reduced, introducer 2900 together with closure 2902B may be inserted, the introducer removed once the closure is in place inside the sleeve. Optionally, a lubricant, for example a gel, is applied to the exterior of the closure and/or of the introducer for reducing friction during insertion.

In some embodiments, introducer 2900 includes a flexible envelope 2920 with a convex-shaped distal end 2924, the envelope attached to a handle 2922. Optionally, flexible envelope 2920 includes is cylindrically shaped resembling a bullet (bullet shaped). Distal end 2924 is adapted to be inserted through the stomal opening, optionally by pushing on handle 2922, so that envelope 2920 and portions of the handle pass into the intestine. Optionally, flexible envelope 2924 is further adapted to be manually rolled onto itself by the user so that a rolled border 2926 is formed by rolling distal edges 2925 in a distal direction. Alternatively, envelope 2924 is inverted by pulling distal edges 2925 is a distal direction passed distal end 2924. Optionally, a mechanical tool is used to pull on the envelope. Optionally, flexible envelope 2920 is made from a biocompatible material such as, for example, silicone.

Figure 29E:
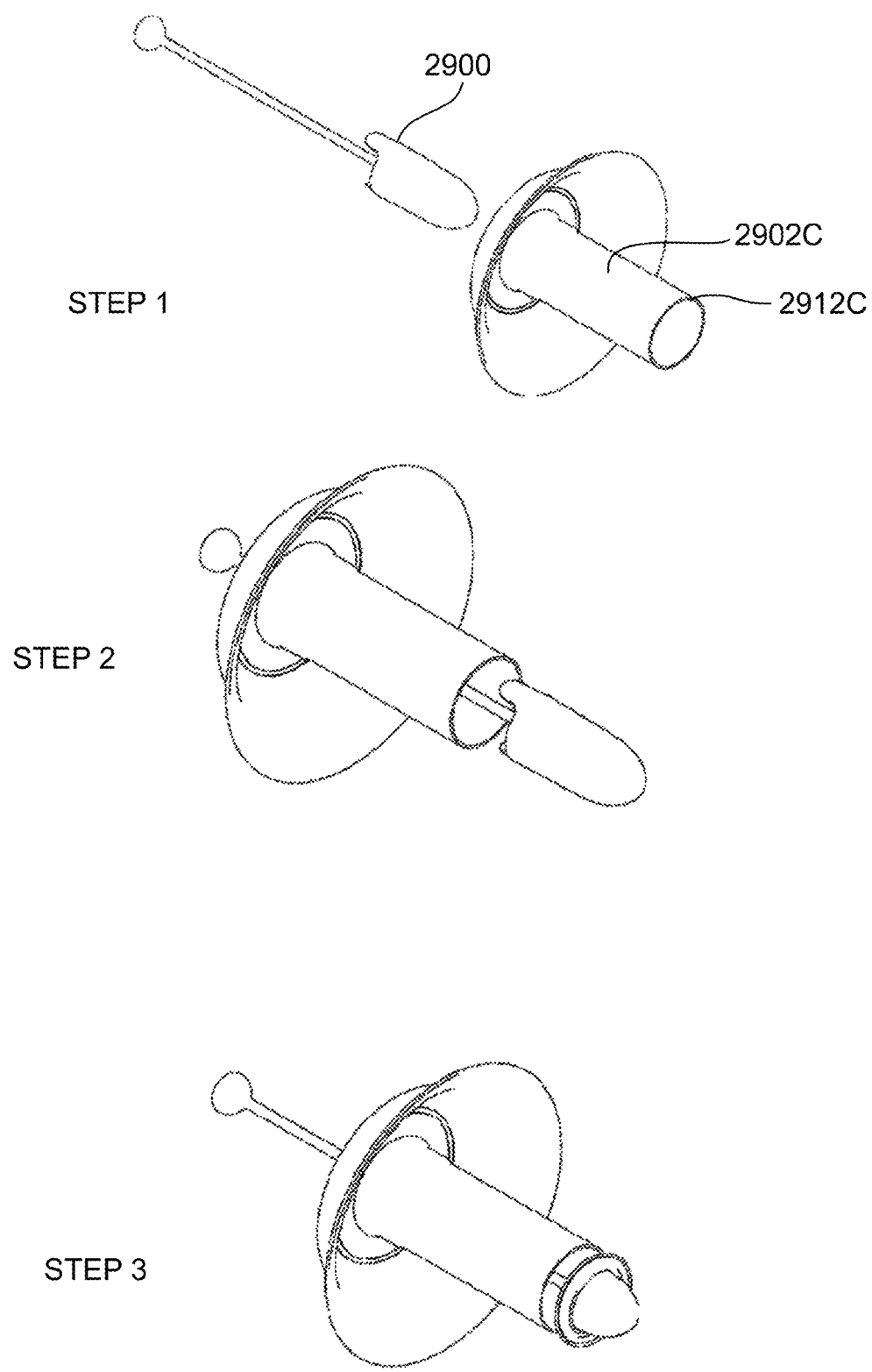

Referring also to FIGS. 29E-29G, an exemplary description is provided of a method for inserting a closure 2902C using introducer 2900, according to some embodiments.

[Step 1] Align the introducer with an axis of closure such that the convex-shaped distal end of the envelope is pointing into the opening at the proximal end of the closure.

[Step 2] Insert the introducer through the opening at the proximal end and push in a distal direction through the closure until the envelope exits distal end 2912C of the closure.

[Step 3] Roll the envelope in the distal direction. Pull the handle of the introducer in the proximal direction causing rolled border 2926 to come in contact with the distal opening (at distal end 2912C) of the closure.

[Step 4] Fold the distal end of the closure. Optionally, folding of the distal end is manually done by the user. Alternatively, a mechanical tool is used to fold the distal end.

[Step 5] "Unroll" the envelope back, optionally to its fully extended length, covering the folded distal end of the closure. Optionally, the bullet shape of the extended envelope while covering the folded distal end allows easy for insertion of the combined closure/introducer into the stomal opening.

[Step 6] Push the introducer in the distal direction together with the closure into the stomal opening until the closure's distal end is appropriately located in the intestine. Lubricant gel or other similar means may be used during this step. Once the closure is in place, push the introducer in the distal direction separating the envelope from the closure's distal end (uncovering the folded distal end). Optionally, the closure's distal end resumes its substantially rounded cross-sectional shape due to its elasticity. Alternatively, the closure's distal end resumes a cross-sectional shape which allows for the envelope to be pulled through in a proximal direction.

[Step 7] Pull the introducer in the proximal direction so that the envelope passes through the opening of the distal end into the closure.

[Step 8] Continue to pull the introducer in the proximal direction until the introducer exits the closure's proximal opening.

In some embodiments, closures 2902A, 2902B and/or 2902C may be similar to that shown in other embodiments disclosed herein this disclosure, with the variations mentioned.

Reference is now made to FIGS. 30A-30F which schematically illustrate exemplary steps in implantation of an exemplary sleeve during the performance of a new end-ostomy using open surgery, according to some embodiments of the present invention. Optionally, the new end-ostomy may include use of sleeve 1, sleeve 1300, or sleeve 1310 shown in FIG. 1, 13A, or 13B, respectively. Optionally, sleeve 1A, 1B, 1320, or 1330 shown in FIG. 3A, 3B, 13C or 13D, respectively, may be used.

In FIG. 30A, optionally, the surgeon sections the abdomen and creates an opening (stoma) in the abdominal wall.

In FIG. 30B, optionally, the surgeon sections the intestine, optionally along with a removal of a portion of the intestine, leaving a functional and a non-functional ends of the intestine.

In FIG. 30C, optionally, the surgeon inserts the functional intestine via the distal opening of the sleeve and pulls it from the proximal opening of the sleeve (the intestine is surrounded by the sleeve).

In FIG. 30D, optionally, the surgeon brings the functional intestine through the abdominal wall to the skin and attaches it to the skin using any accepted method for surgical attachment, for example, sutures or staples.

In FIG. 30E, optionally, the surgeon attaches a flange of a sleeve to a surface of the abdominal wall using any accepted method for surgical attachment, for example, sutures or staples. Optionally, the surgeon attaches a distal portion of the sleeve to the functional intestine using any accepted method for surgical attachment, for example, sutures or staples.

In FIG. 30F, optionally, the surgeon inserts a finger into the stomal opening and validates a free pathway for body waste.

Reference is now made to FIGS. 31A-31F which schematically illustrate exemplary steps in implantation of an exemplary sleeve on an existing end-ostomy using open surgery, according to some embodiments of the present invention. Optionally, the procedure may include use of sleeve 1A or 1B, shown in FIG. 3A or 3B, respectively.

Figure 31A:
FIGS. 31A-31F schematically illustrate exemplary steps in implantation of an exemplary sleeve on an existing end-ostomy using open surgery, according to some embodiments of the present invention.

In FIG. 31A, optionally, the surgeon sections the abdomen. Optionally, the end-ostomy is existing.

Figure 31B:
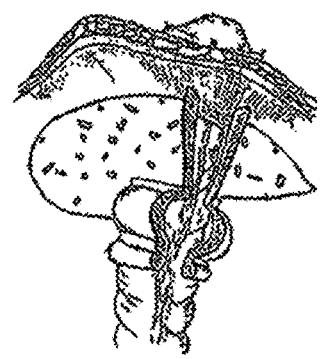

In FIG. 31B, optionally, the surgeon places the sleeve around the functional intestine using the slit along the sleeve.

Figure 31C:
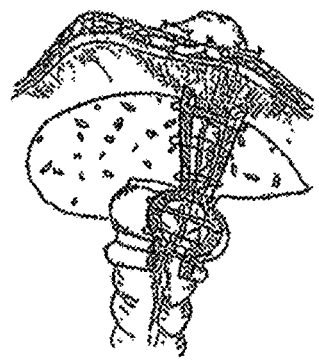

In FIG. 31C, optionally, the surgeon attaches both edges of the slit to one another using the dedicated pins, to close the gap created by the slit along the sleeve. Alternatively, attachment is performed using any other accepted method for surgical attachment, for example, sutures or staples.

Figure 31D:
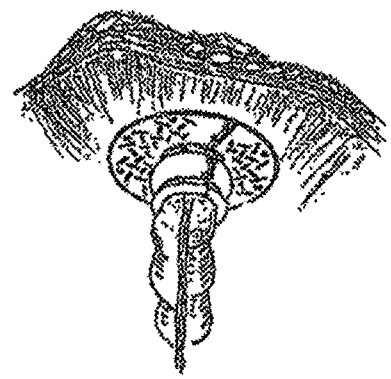

In FIG. 31D, optionally, the surgeon attaches the flange of the sleeve to a surface of the abdominal wall using any accepted method for surgical attachment, for example, sutures or staples.

Figure 31E:
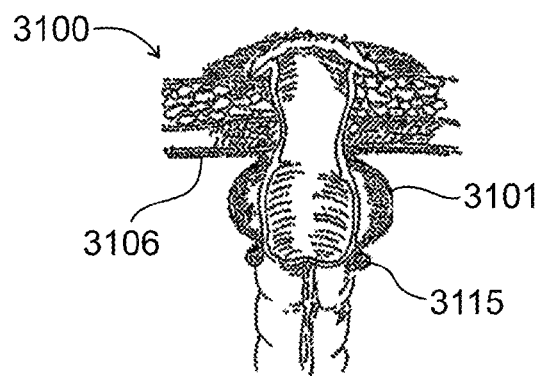

In FIG. 31E, optionally, the surgeon attaches the distal portion of the sleeve to the functional intestine, using any accepted method for surgical attachment, for example, sutures or staples.

Figure 31F:
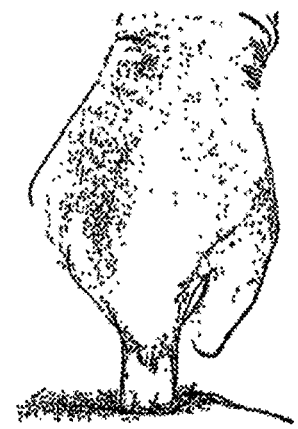

In FIG. 31F, optionally, the surgeon inserts a finger into the stomal opening and validates a free pathway for body waste.

Reference is now made to FIGS. 32A-32H which schematically illustrate exemplary steps in implantation of an exemplary sleeve during the performance of a new end-ostomy using laparoscopic surgery, according to some embodiments of the present invention. Optionally, the new end-ostomy may include use of sleeve 1, sleeve 1300, or sleeve 1310 shown in FIG. 1, 13A, or 13B, respectively. Optionally, sleeve 1A, 1B, 1320, or 1330 shown in FIG. 3A, 3B, 13C or 13D, respectively, may be used.

Figure 32A:
FIGS. 32A-32H schematically illustrate exemplary steps in implantation of an exemplary sleeve during the performance of a new end-ostomy using laparoscopic surgery, according to some embodiments of the present invention.

In FIG. 32A, optionally, the surgeon creates holes in the abdominal wall for imaging and working tools. Optionally the surgeon sections the intestine, optionally along with a removal of a portion of the intestine, leaving a functional and a non-functional ends of the intestine.

Figure 32B:

In FIG. 32B, optionally, the surgeon creates a stoma in the abdominal wall.

Figure 32C:

In FIG. 32C, optionally, the surgeon furls the sleeve into a dense cylindrical shape.

Figure 32D:
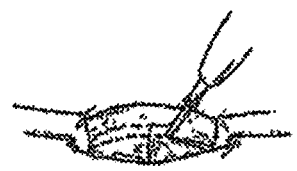

In FIG. 32D, optionally, the surgeon inserts the sleeve through the stoma into the abdominal cavity.

Figure 32E:
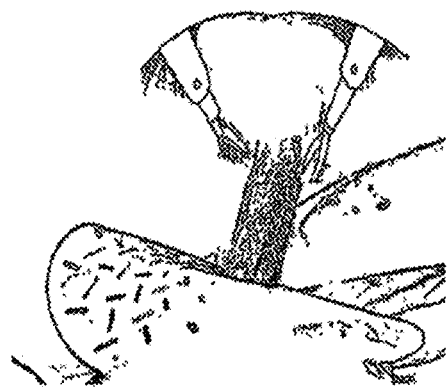

In FIG. 32E, optionally, the surgeon passes the functional intestine through the distal opening of the sleeve and pulls it from the proximal opening of the sleeve (the intestine is surrounded by the sleeve).

Figure 32F:
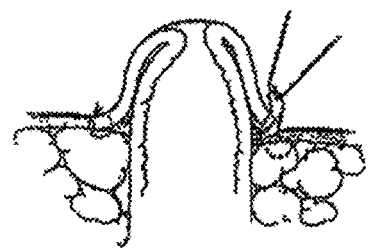

In FIG. 32F, optionally, the surgeon brings the functional intestine through the stoma to the skin and attaches it to the skin using any accepted method for surgical attachment, for example, sutures or staples.

Figure 32G:
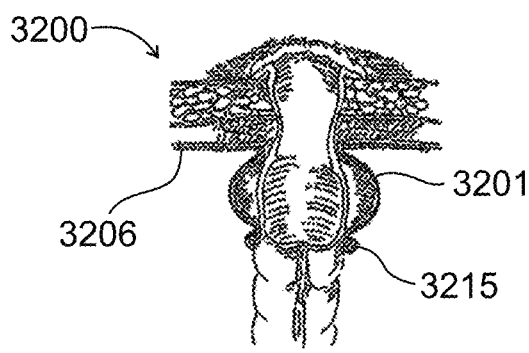

In FIG. 32G, optionally, the surgeon attaches the flange of the sleeve to a surface of the abdominal wall using any accepted method for surgical attachment, for example, sutures or staples. Optionally, the surgeon attaches the distal portion of the sleeve to the functional intestine using any accepted method for surgical attachment, for example, sutures or staples.

Figure 32H:
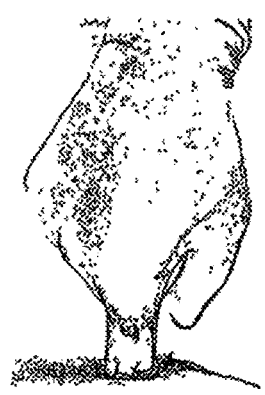

In FIG. 32H, optionally, the surgeon inserts a finger into the stomal opening and validates a free pathway for body waste.

Reference is now made to FIGS. 33A-33F which schematically illustrate exemplary steps in implantation of an exemplary sleeve on an existing end-ostomy using laparoscopic surgery, according to some embodiments of the present invention. Optionally, the procedure may include use of sleeve 1A or 1B, shown in FIG. 3A or 3B, respectively.

Figure 33A:
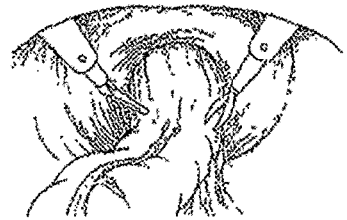
FIGS. 33A-33F schematically illustrate exemplary steps in implantation of an exemplary sleeve on an existing end-ostomy using laparoscopic surgery, according to some embodiments of the present invention.

In FIG. 33A, optionally, the surgeon creates holes in the abdominal wall for imaging and working tools. Optionally, the end-ostomy is existing. Optionally, the surgeon furls the sleeve into a dense cylindrical shape and inserts it through one of the openings in the abdominal wall. Optionally, the opening may be slightly enlarged to accommodate the passage of the sleeve.

Figure 33B:
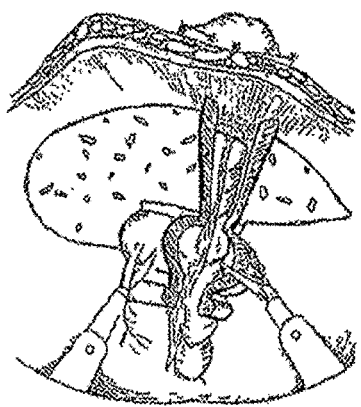

In FIG. 33B, optionally, the surgeon places a sleeve around the functional intestine using the slit along the sleeve. Optionally, the surgeon closes the gap created by the slit along the sleeve.

Figure 33C:
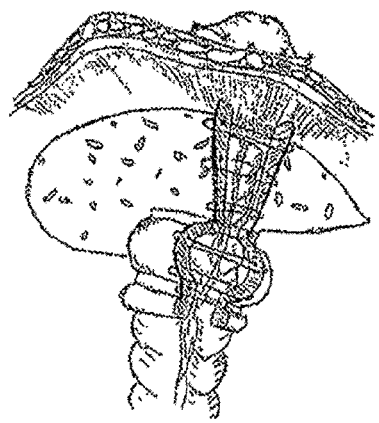

In FIG. 33C, optionally, the surgeon attaches both edges of the slit to one another using the dedicated pins, to close the gap created by the slit along the sleeve. Alternatively, attachment is performed using any accepted method for surgical attachment, for example, sutures or staples.

Figure 33D:
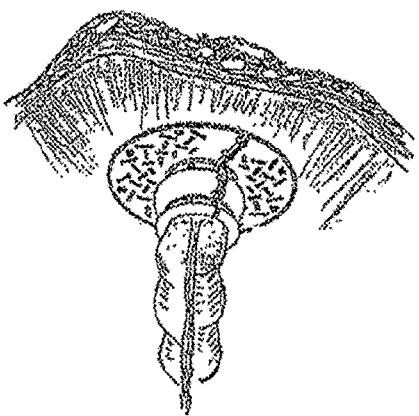

In FIG. 33D, optionally, the surgeon attaches the flange of the sleeve to a surface of the abdominal wall using any accepted method for surgical attachment, for example, sutures or staples.

Figure 33E:
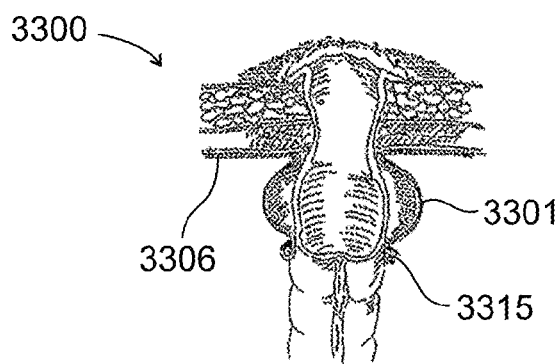

In FIG. 33E, optionally, the surgeon attaches the distal portion of the sleeve to the functional intestine using any accepted method for surgical attachment, for example, sutures or staples.

Figure 33F:

In FIG. 33F, optionally, the surgeon inserts a finger into the stomal opening and validates a free pathway for bowel content.

Reference is now made to FIGS. 34A-34G which schematically illustrate exemplary steps in implantation of an exemplary sleeve during the performance of a new loop or "double barrel" ostomy using open surgery, according to some embodiments of the present invention. Optionally, the new loop or "double barrel" ostomy may include use of sleeve 1320 or 1330, shown in FIG. 13C or 13D, respectively.

Figure 34A:
FIGS. 34A-34G schematically illustrate exemplary steps in implantation of an exemplary sleeve during the performance of a new loop or "double barrel" ostomy using open surgery, according to some embodiments of the present invention.

In FIG. 34A, optionally, the surgeon sections the abdomen and creates a stoma in the abdominal wall. Optionally, the surgeon sections the intestine, optionally along with a removal of a portion of the intestine, leaving a functional and a non-functional ends of the intestine.

Figure 34B:
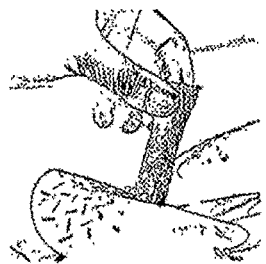

In FIG. 34B, optionally, the surgeon inserts the intestine through the distal opening of the sleeve and pulls it from the proximal opening of the sleeve (the intestine is surrounded by the sleeve).

Figure 34C:
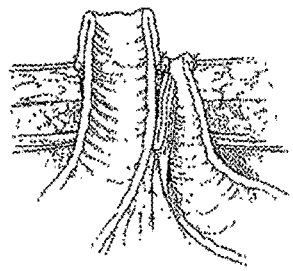

In FIG. 34C, optionally, the surgeon brings the intestine through the stoma to the skin.

Figure 34D:

In FIG. 34D, optionally, the surgeon attaches the functional intestine to the skin using any accepted method for surgical attachment, for example, sutures or staples, creating a loop or "double barrel" ostomy.

Figure 34E:
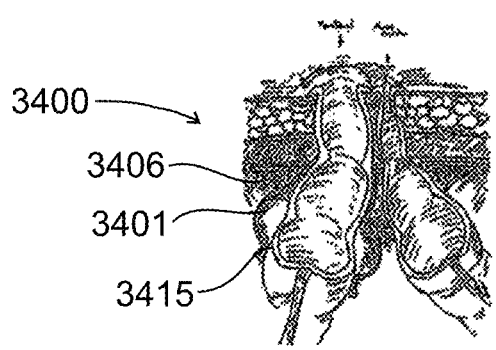

In FIG. 34E, optionally, the surgeon attaches the flange of the sleeve to a surface of the abdominal wall using any accepted method for surgical attachment, for example, sutures or staples.

Figure 34F:
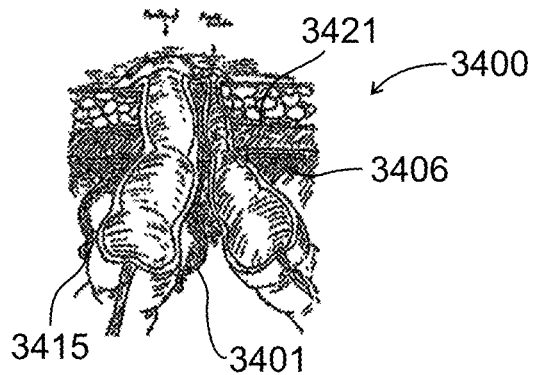

In FIG. 34F, optionally, the surgeon attaches the distal portion of the sleeve to the functional intestine, using any accepted method for surgical attachment, for example, sutures or staples.

Figure 34G:
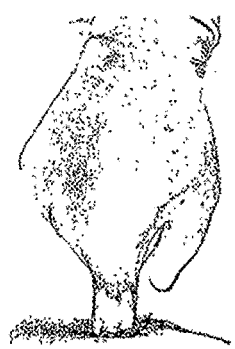

In FIG. 34G, optionally, the surgeon inserts a finger into the stomal opening and validates a free pathway for bowel content. Optionally, if the ostomy is a temporary ostomy (use sleeve 1330), following the required healing period, the sleeve is removed by creating a circular section in the abdominal wall around the stoma. Optionally, the sleeve and the intestine are pulled out from the body together through the opening. Optionally, the sleeve is removed from the intestine.

Reference is made to FIGS. 35A-35E which schematically illustrate various exemplary ostomy containment devices 1000-1003 excluding sleeves, according to some embodiments of the present invention. Optionally, use of containment devices 1000-1003 is advantageous as surgery is not required for inserting the sleeve. Optionally, devices 1000-1003 are suitable for use where an internal pouch is created, for example, as may be in the case of continent ostomy.

Figure 35A:
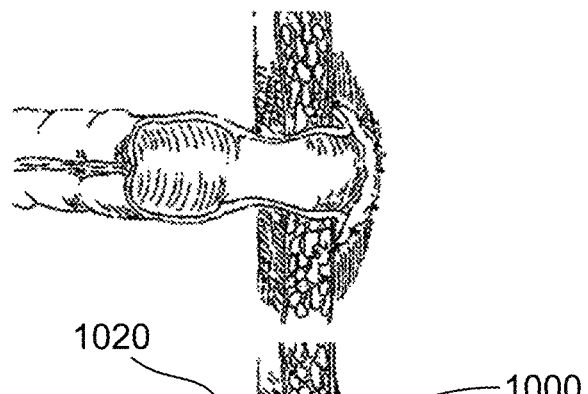
FIGS. 35A-35E schematically illustrate various exemplary ostomy containment devices excluding sleeves, according to some embodiments of the present invention.

Shown in FIG. 35A is the intestine inserted through the stomal opening and attached to the abdomen (outside the body).

Figure 35B:
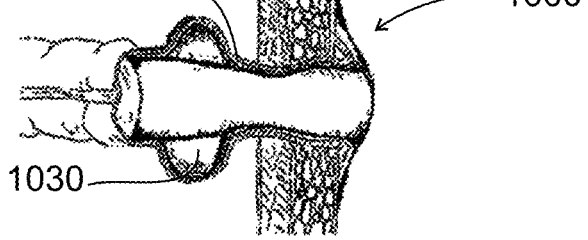

Shown in FIG. 35B is device 1000 which includes a closure 1020 which is inserted into the intestine. Closure 1020 is held in position by a fixation device 1030 which may be, for example, an inflatable balloon. Optionally, closure 1020 and balloon 1030 are similar to that shown in FIG. 1 at 2 and 25, respectively.

Figure 35C:
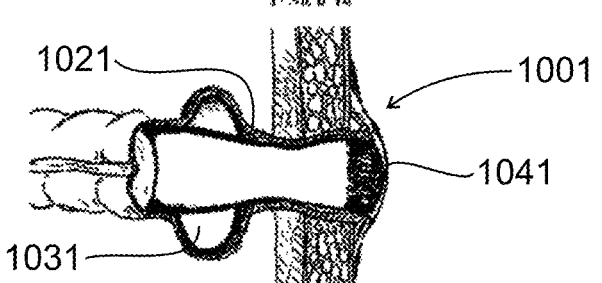

Shown in FIG. 35C is device 1001 which includes a closure 1021 which is inserted into the intestine. Closure 1021 is held in position by a fixation device 1031 which may be, for example, an inflatable balloon. Closure 1021 is adapted to hold a waste content bag 1041 inside the proximal end of the closure. Optionally, closure 1020, balloon 1030, and waste content bag 1041 are similar to that shown in FIG. 1 at 2, 25 and 3, respectively.

Figure 35D:
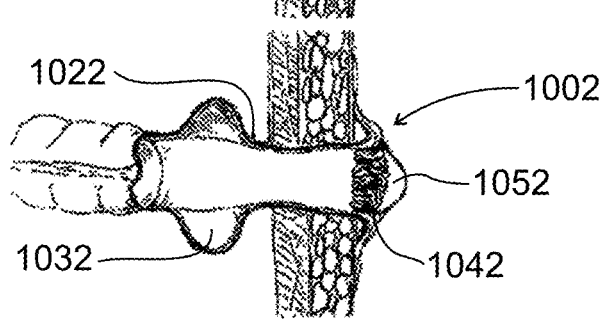

Shown in FIG. 35D is device 1002 which includes a closure 1022 which is inserted into the intestine. Closure 1022 is held in position by a fixation device 1032 which may be, for example, an inflatable balloon. Closure 1022 is adapted to hold a waste content bag 1042 inside the proximal end of the closure, and is further adapted to accommodate a cap 1052 for sealing the proximal end of the closure. Optionally, cap 1052 substantially prevents bag 1052 from being deployed accidentally. Optionally, closure 1022, balloon 1032, waste content bag 1042, and cap 1052 are similar to that shown in FIG. 1 at 2, 25, 3, and 4 respectively.

Figure 35E:
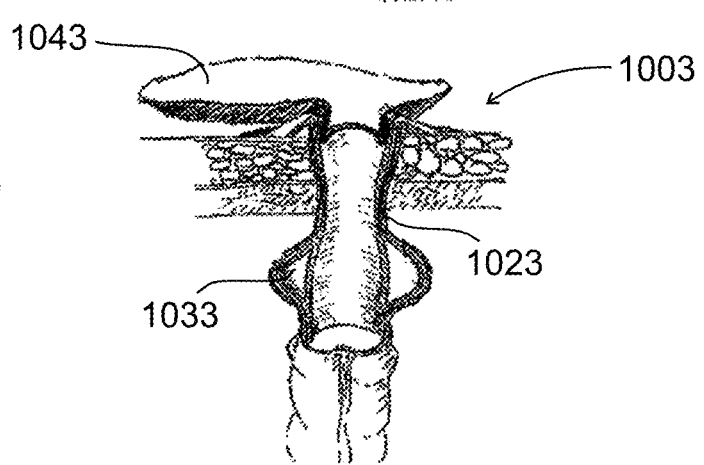

Shown in FIG. 35E is device 1003 which includes a closure 1023 which is inserted into the intestine. Closure 1023 is held in position by a fixation device 1033 which may be, for example, an inflatable balloon. Closure 1023 is adapted to hold an open (deployed) waste content bag 1043 attached to the proximal end of the closure into which waste content may flow at any time. Optionally, waste content bag 1043 is replaceable. Alternatively, waste content bag 1043 is a furled (folded) bag similar to that shown in FIG. 1 at 3, in a deployed state. Optionally, closure 1023 and balloon 1033 are similar to that shown in FIG. 1 at 2 and 25, respectively.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An artificial ostomy containment device comprising:
    a closure assembly adapted to conduct waste content from an intestinal portion in an abdominal cavity and out of a stoma;
    a fixation element sized and positioned to interfere with movement of said closure assembly;
    a stomal cover sized and shaped to cover the stoma from outside the abdominal cavity; and
    a pressure indicator which acts as a pressure sensing mechanism, the pressure indicator having a portion externally positioned on the device outside the abdominal cavity, the portion being configured to bulge from an equilibrium state as a buildup of axial pressure conveyed from within the abdominal cavity to said pressure indicator occurs, and according to said conveyed pressure.

2. The containment device according to claim 1 wherein the fixation element is an inflatable balloon.

3. The containment device according to claim 1 wherein the closure assembly comprises an inflation valve for introducing the expansion fluid into a lumen.

4. The containment device according to claim 1 wherein the fixation element is a pre-shaped elastically deformable element configured to be inserted into said intestinal portion.

5. The containment device according to claim 1 wherein said stomal cover includes a flatus release mechanism for controlling a pressure buildup in said closure assembly.

6. The containment device according to claim 1 comprising a safety mechanism for releasing bowel waste content when a colonic pressure reaches a predetermined value.

7. The containment device according to claim 1 wherein the closure assembly comprises a material of durometer ranging from 20-80 Shore A for allowing peristaltic propelling of the waste content.

8. The containment device according to claim 1 wherein the fixation element comprises a non-collapsible balloon.

9. The containment device according to claim 1 wherein a shape of said stomal cover is invertible to allow access to the stoma.

10. The containment device according to claim 1 comprising a disposable bag assembly for collecting waste content from the device, said assembly comprising:
    a bag housing attachable to a proximal end of said closure assembly; and
    a waste content collection bag folded in said bag housing.

11. The containment device according to claim 10 wherein the bag housing is replaceable.

12. The containment device according to claim 10 wherein the bag housing is permanently affixed to the closure assembly.

13. The containment device according to claim 1 wherein said pressure sensing mechanism is configured to sense a pressure from said waste content.

14. The containment device of claim 5 wherein said flatus release mechanism is controllable by a user of the device.

15. The containment device of claim 5 wherein said flatus release mechanism includes a sealable opening in said stomal cover configured for allowing passage of flatus.

16. The containment device of claim 1 comprising a waste blocking mechanism for preventing waste content from flowing out of the device when a waste content collection bag is unattached to the device.

17. The containment device of claim 16 wherein said waste blocking mechanism includes a one-way valve.

18. The containment device of claim 1 wherein said fixation element is coupled to a stomal insert in said closure assembly.

19. The containment device of claim 1 wherein said stomal cover is coupled to a stomal insert in said closure assembly.

20. The containment device according to claim 1, wherein said closure assembly further comprises a stomal insert passing into the stoma.

21. The containment device according to claim 20, wherein the stomal insert comprises a lumen for conveying an expansion fluid to an inflatable balloon.

22. The containment device according to claim 20, comprising an inflatable balloon inside the stomal insert for blocking a flow of the waste content.

23. The containment device according to claim 20, wherein the fixation element comprises a broadening of the stomal insert.

24. The containment device according to claim 1, wherein said stomal cover blocks said conducting of waste content, and comprises an external surface adapted to change shape due to pressure from within the abdominal cavity.

25. The containment device according to claim 24, wherein said change of shape communicates to a user an indication of said pressure.

26. The containment device according to claim 24, wherein said change of shape comprises protruding.

27. The containment device according to claim 24, wherein said change of shape comprises holding a protruding conformation.

* * * * *